US012251679B2

(12) United States Patent
Uribe-Romo et al.

(10) Patent No.: US 12,251,679 B2
(45) Date of Patent: Mar. 18, 2025

(54) MULTIVARIATE METAL-ORGANIC FRAMEWORKS FOR FINE-TUNING LIGHT EMISSION

(71) Applicant: UNIVERSITY OF CENTRAL FLORIDA RESEARCH FOUNDATION, INC., Orlando, FL (US)

(72) Inventors: Fernando J. Uribe-Romo, Orlando, FL (US); Jesus Cordova-Guerrero, Orlando, FL (US); Gavin S. Mohammad-Pour, Orlando, FL (US); Wesley Newsome, Orlando, FL (US)

(73) Assignee: UNIVERSITY OF CENTRAL FLORIDA RESEARCH FOUNDATION, INC., Orlando, FL (US)

( * ) Notice: Subject to any disclaimer, the term of this patent is extended or adjusted under 35 U.S.C. 154(b) by 0 days.

(21) Appl. No.: 18/143,781

(22) Filed: May 5, 2023

(65) Prior Publication Data
US 2023/0381740 A1    Nov. 30, 2023

Related U.S. Application Data

(62) Division of application No. 16/956,781, filed as application No. PCT/US2018/067035 on Dec. 21, 2018, now Pat. No. 11,679,372.

(60) Provisional application No. 62/608,942, filed on Dec. 21, 2017.

(51) Int. Cl.
| | |
|---|---|
| C07F 19/00 | (2006.01) |
| B01J 20/22 | (2006.01) |
| C07C 63/331 | (2006.01) |
| C07F 7/00 | (2006.01) |
| C09K 11/06 | (2006.01) |
| H10K 50/125 | (2023.01) |
| C07D 235/02 | (2006.01) |

(52) U.S. Cl.
CPC ............ *B01J 20/226* (2013.01); *C07C 63/331* (2013.01); *C07F 7/003* (2013.01); *C09K 11/06* (2013.01); *H10K 50/125* (2023.02); *C09K 2211/183* (2013.01)

(58) Field of Classification Search
CPC .............................. C07D 235/02; C07F 19/00
USPC ................................................ 548/301.7, 108
See application file for complete search history.

(56) References Cited

U.S. PATENT DOCUMENTS

| 9,741,945 B1 | 8/2017 | Nenoff et al. |
| 2010/0187505 A1 | 7/2010 | Stoessel et al. |
| 2017/0231903 A1 | 8/2017 | Lin et al. |

FOREIGN PATENT DOCUMENTS

WO    2014033481 A2    3/2014

OTHER PUBLICATIONS

Butova, V V et al., "Metal-organic frameworks: structure, properties, methods of synthesis and characterization", Russian Chemical Reviews, 2016, vol. 85, issue 3, pp. 280-307.
Cornella, Josep et al., "Ni-catalyzed Reductive Cleavage of Methyl 3-Methoxy-2-Naphthoate", Org. Synth., 2014, vol. 91, pp. 260-272.
http://www.crystallography.net/cod/4512072.html, accessed on Nov. 2, 2017, 3 pages.
Davidenko, N.A. et al., "Photophysical Properties of Film Composites of Organic Polymers With Heterometallic Complexes of Transition Metals: A Review", Theoretical and Experimental Chemistry, May 2017, vol. 53, No. 2, (Russian Original vol. 53, No. 2, Mar.-Apr. 2017).
Deng, Hexiang et al., "Multiple Functional Groups of Varying Ratios in Metal-Organic Frameworks", Science, Feb. 12, 2010, vol. 327, pp. 846-850.
Kuss-Petermann, Martin et al., "Electron Transfer Rate Maxima at Large Donor-Acceptor Distances", J. Am. Chem. Soc., 2016, vol. 138, pp. 1349-1358.
Lippke, Jann et al., "Expanding the Group of Porous Interpenetrated Zr-Organic Frameworks (PIZOFs) with Linkers of Different Lengths", Inorg. Chem., 2017, vol. 56, pp. 748-761.
Park, Sanghyuk et al., "Strategic emission color tuning of highly fluorescent imidazole-based excited-state Intramolecular proton transfer molecules", Phys. Chem. Chem. Phys., 2012, vol. 14, pp. 8878-8884.
Qin, Jun-Sheng et al., "Mixed-linker strategy for the construction of multifunctional metal-organic frameworks", J. Mater. Chem. A, 2017, vol. 5, pp. 4280-4291.
Sun, Chun-Yi et al., "Efficient and tunable white-light emission of metal-organic frameworks by iridium-complex encapsulation", Nature Communications, 2013, vol. 4, No. 2717, pp. 1-8.
Wang et al., "Warm-White-Light-Emitting Diode Based on a Dye-Loaded Metal-Organic Framework for Fast White-Light Communication", 2017, vol. 9, No. 40, pp. 35253-35259.
Wu, Kun-Chan et al., "Design and synthesis of intramolecular hydrogen bonding systems. Their application in metal cation sensing based on excited-state proton transfer reaction", Tetrahedron, 2004, vol. 60, pp. 11861-11868.
Yang, Xuejin et al., "Heptagon-Embedded Pentacene: Synthesis, Structures, and Thin-Film Transistors of Dibenzo[d, d']benzo[1,2-a:4,5-a']dicycloheptenes", Angew. Chem. Int. Ed., 2014, vol. 53, pp. 6786-6790.

(Continued)

*Primary Examiner* — Charanjit Aulakh
(74) *Attorney, Agent, or Firm* — Timothy H. Van Dyke; Wolter Van Dyke Davis, PLLC

(57) ABSTRACT

Multivariate metal-organic framework compositions and methods of producing multivariate metal-organic frameworks. The metal-organic framework including at least one light-emitting linker in an amount sufficient for the composition to produce broadband emission spectra in high efficiencies.

5 Claims, 60 Drawing Sheets

(56) References Cited

OTHER PUBLICATIONS

PCT/US18/67035; PCT Search Report & Written Opinion, May 7, 2019, 9 pages.
Newsome, Wesley J. et al., "Solid State Multicolor Emission in Substitutional Solid Solutions of Metal-Organic Frameworks", J. Am. Chem. Soc., 2019, vol. 141, pp. 11298-11303.

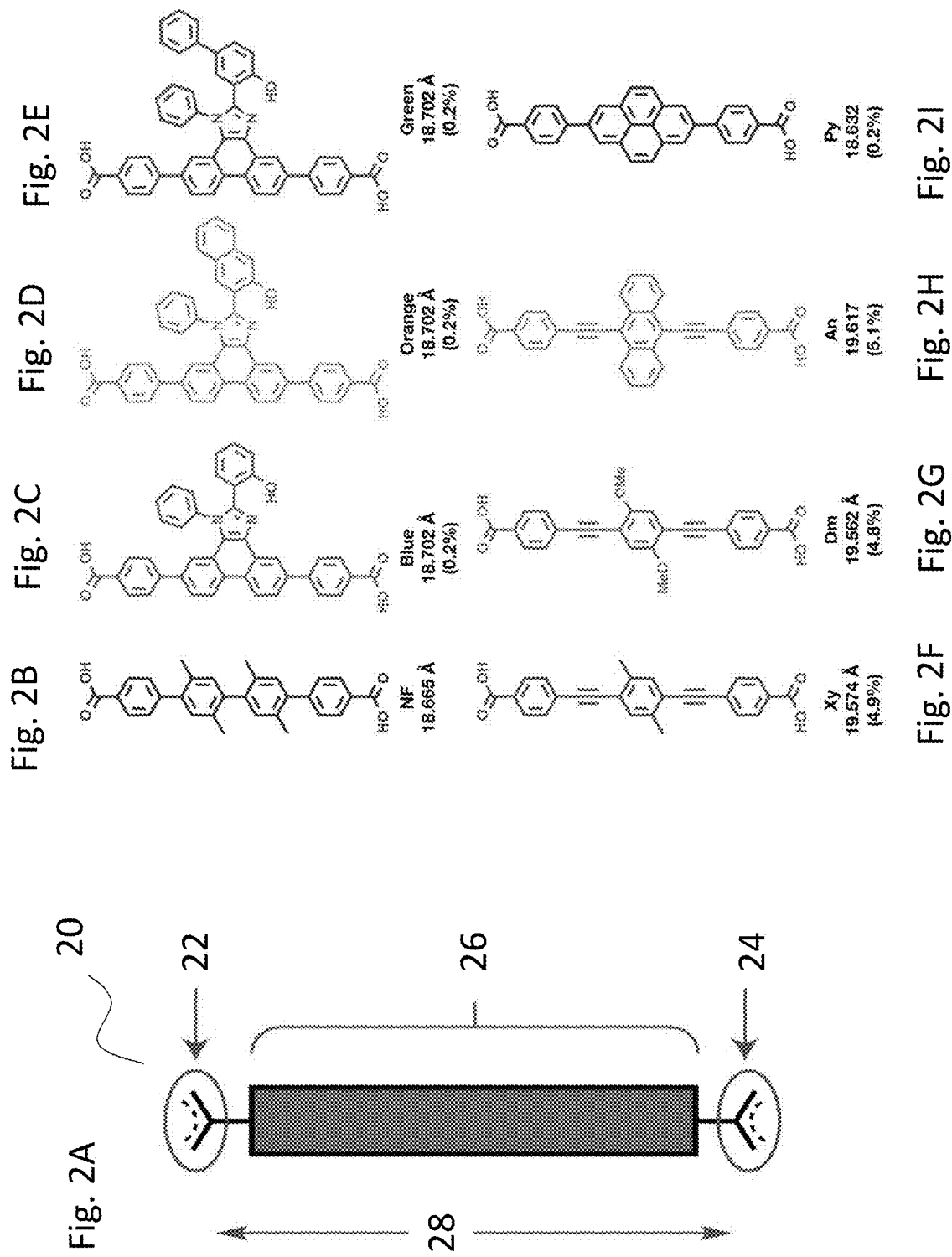

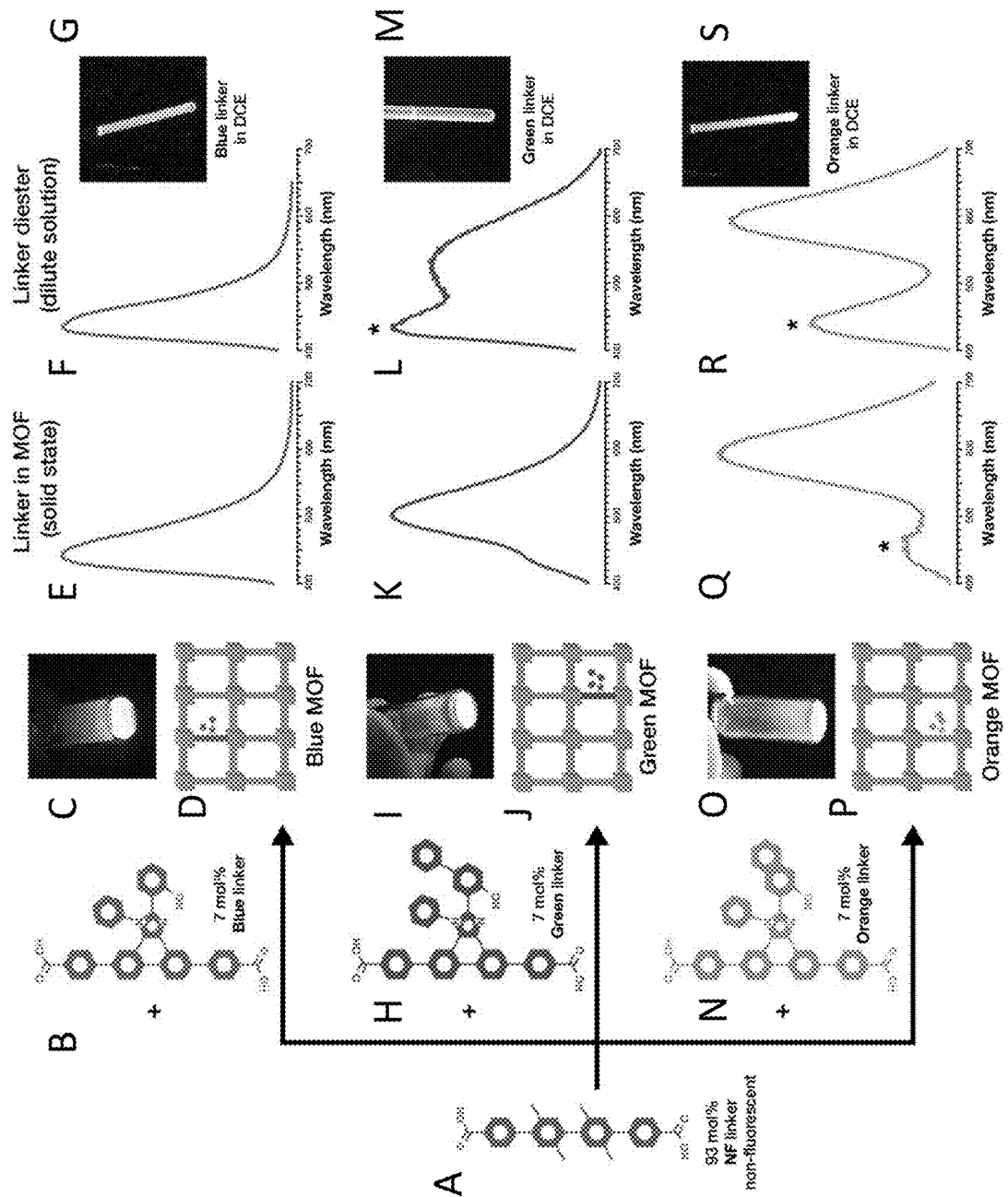
FIGs. 3A-S

MULTIVARIATE METAL-ORGANIC FRAMEWORKS FOR FINE-TUNING LIGHT EMISSION

BACKGROUND

In the USA, lighting in residential and commercial sectors consume almost 280 billion kWh or energy yearly, which is around 10% of the total energy consumption in these sectors. The majorly of this lighting consumption is in the form of white light which is obtained from a variety of devices-types such as incandescent bulbs, compact fluorescent lamps (CFL), and light-emitting diodes (LED). Each of these devices-types has a unique lighting producing mechanism, which is characterized by sets of advantages and disadvantages. For example, while LEDs exhibit the highest energy consumption efficiencies observed so far, obtaining white light from such devices requires the use of expensive and rare elements such as iridium, gallium, and lanthanides. Furthermore, the production and use of these materials are not environmentally friendly.

While incandescent lighting devices are energy inefficient, they deliver comfortable color and warmth. On the other hand, LED lighting has traditionally been associated with monotone light. However, it is possible to adjust or tune the LED light color to deliver the perfect color temperature for any application. Fine-tuning of the color (or black body temperature) of the white light is especially difficult, because white light is comprised of multiple wavelengths of different intensities that range from "warm" (1900 K) to "cool" (10 000 K) and each of these wavelengths must be tuned independently. Moreover, each of the different types of light produces different psychological effects in people. Given the economic, environmental, and psychological importance of light tuning, it is an important scientific challenge to create materials that are able to produce white light at targeted temperatures and hues, and that require sustainable materials.

BRIEF SUMMARY

Various embodiments relate to a composition comprising a metal-organic framework, the metal-organic framework may include at least one light-emitting linker in an amount sufficient for the composition to produce broadband emission spectra in high quantum yields. The metal-organic Framework may comprise clusters of $Zr_6O_4(OH)_4$ clusters connected through the organic linkers.

Various embodiments relate to a method of producing a light-emitting metal-organic framework. The method may include combining at least one light-emitting linker precursor, having a formula selected from the group consisting of:

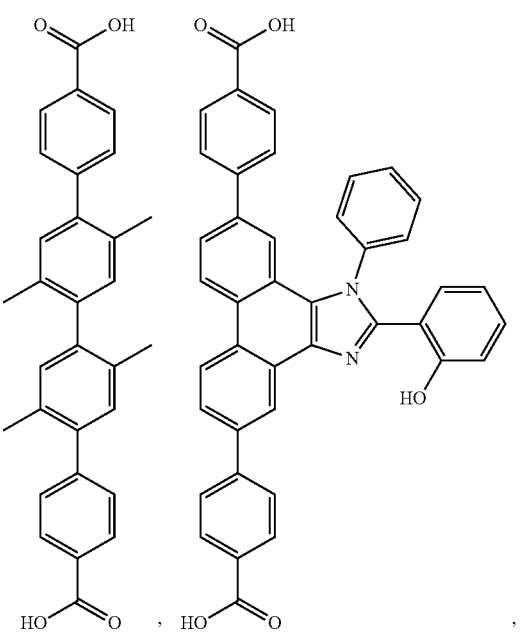

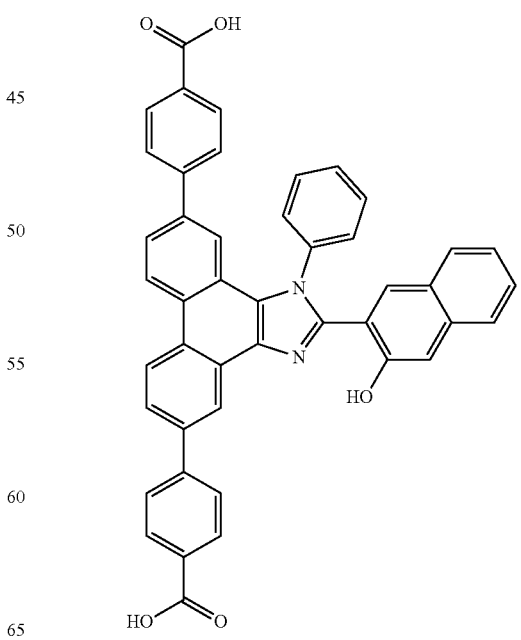

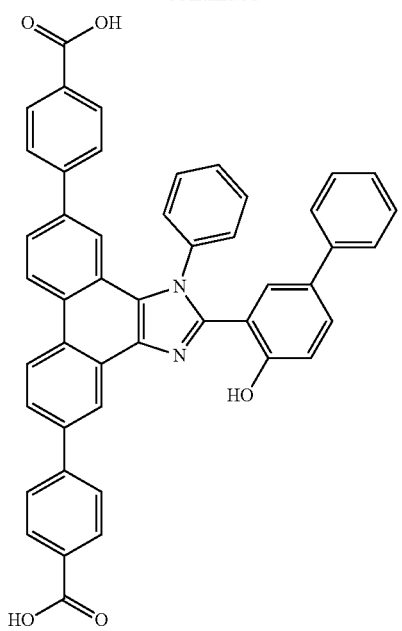

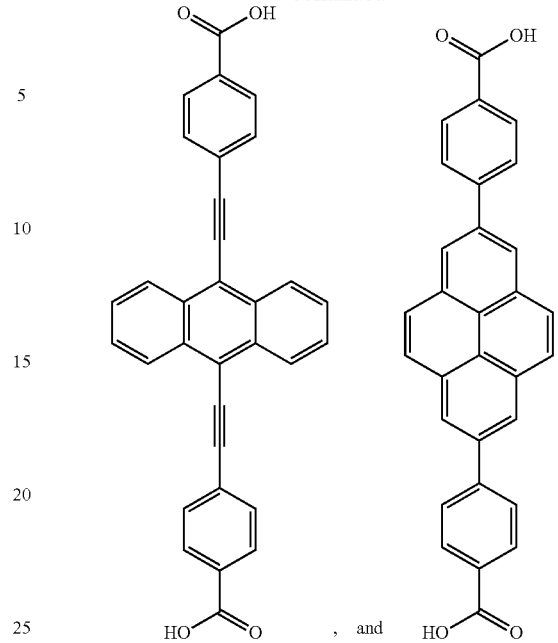

with a non-fluorescent linker, having a formula:

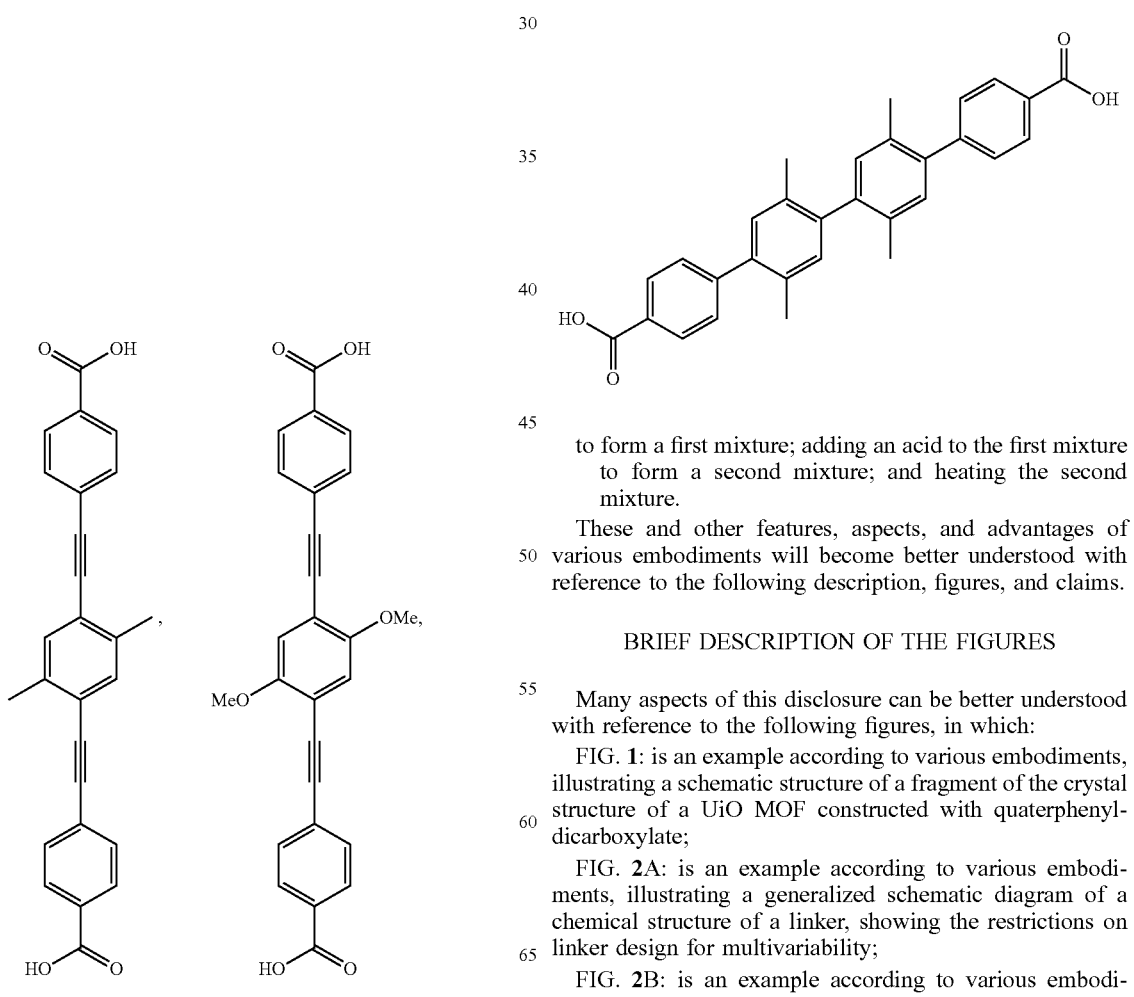

to form a first mixture; adding an acid to the first mixture to form a second mixture; and heating the second mixture.

These and other features, aspects, and advantages of various embodiments will become better understood with reference to the following description, figures, and claims.

BRIEF DESCRIPTION OF THE FIGURES

Many aspects of this disclosure can be better understood with reference to the following figures, in which:

FIG. 2A: is an example according to various embodiments, illustrating a generalized schematic diagram of a chemical structure of a linker, showing the restrictions on linker design for multivariability;

FIG. 2B: is an example according to various embodiments, illustrating a chemical structure of an organic linker utilized for UiO-type MOFs in the illustrative embodiments and displaying its abbreviation "NF", used for reference in this disclosure;

FIG. 2C: is an example according to various embodiments, illustrating a chemical structure of an organic linker utilized for UiO-type MOFs in the illustrative embodiments and displaying its abbreviation "Blue", used for reference in this disclosure;

FIG. 2D: is an example according to various embodiments, illustrating a chemical structure of an organic linker utilized for UiO-type MOFs in the illustrative embodiments and displaying its abbreviation "Orange", used for reference in this disclosure;

FIG. 2E: is an example according to various embodiments, illustrating a chemical structure of an organic linker utilized for UiO-type MOFs in the illustrative embodiments and displaying its abbreviation "Green", used for reference in this disclosure;

FIG. 2F: is an example according to various embodiments, illustrating a chemical structure of an organic linker utilized for UiO-type MOFs in the illustrative embodiments and displaying its abbreviation "Xy", used for reference in this disclosure;

FIG. 2G: is an example according to various embodiments, illustrating a chemical structure of an organic linker utilized for UiO-type MOFs in the illustrative embodiments and displaying its abbreviation "Dm", used for reference in this disclosure;

FIG. 2H: is an example according to various embodiments, illustrating a chemical structure of an organic linker utilized for UiO-type MOFs in the illustrative embodiments and displaying its abbreviation "An", used for reference in this disclosure;

FIG. 2I: is an example according to various embodiments, illustrating a chemical structure of an organic linker utilized for UiO-type MOFs in the illustrative embodiments and displaying its abbreviation "Py", used for reference in this disclosure;

FIG. 3A: is an example according to various embodiments, illustrating a step of providing 93 mol % of the non-fluorescent NF linker from FIG. 2B;

FIG. 3B: is an example according to various embodiments, illustrating a step of adding 7 mol % of the blue linker from FIG. 2C to the non-fluorescent NF linker provided in the step illustrated in FIG. 3A;

FIG. 3C: is an example according to various embodiments, showing a photograph of the blue linker from FIG. 3B in a metal-organic framework (MOF) under UV light;

FIG. 3D: is an example according to various embodiments, illustrating the blue linker from FIG. 3B in a metal-organic framework;

FIG. 3E: is an example according to various embodiments, illustrating a fluorescence spectra that was obtained with $\lambda_{ex}$=385 nm of the blue linker from FIG. 3B in a metal-organic framework in a solid state;

FIG. 3F: is an example according to various embodiments, illustrating a fluorescence spectra that was obtained with $\lambda_{ex}$=385 nm of the blue linker from FIG. 3B in a dilute solution;

FIG. 3G: is an example according to various embodiments, showing a photograph of the blue linker from FIG. 3B in a dilute solution under UV light;

FIG. 3H: is an example according to various embodiments, illustrating a step of adding 7 mol % of the green linker from FIG. 2E to the non-fluorescent NF linker provided in the step illustrated in FIG. 3A;

FIG. 3I: is an example according to various embodiments, showing a photograph of the green linker from FIG. 3H in a metal-organic framework under UV light;

FIG. 3J: is an example according to various embodiments, illustrating the green linker from FIG. 3H in a metal-organic framework;

FIG. 3K: is an example according to various embodiments, illustrating a fluorescence spectra that was obtained with $\lambda_{ex}$=385 nm of the green linker from FIG. 3H in a metal-organic framework in a solid state;

FIG. 3L: is an example according to various embodiments, illustrating a fluorescence spectra that was obtained with $\lambda_{ex}$=385 nm of the green linker from FIG. 3H in a dilute solution;

FIG. 3M: is an example according to various embodiments, showing a photograph of the green linker from FIG. 3H in a dilute solution under UV light;

FIG. 3N: is an example according to various embodiments, illustrating a step of adding 7 mol % of the orange linker from FIG. 2D to the non-fluorescent NF linker provided in the step illustrated in FIG. 3A;

FIG. 3O: is an example according to various embodiments, showing a photograph of the orange linker from FIG. 3N in a metal-organic framework under UV light;

FIG. 3P: is an example according to various embodiments, illustrating the orange linker from FIG. 3N in a metal-organic framework;

FIG. 3Q: is an example according to various embodiments, illustrating a fluorescence spectra that was obtained with $\lambda_{ex}$=385 nm of the orange linker from FIG. 3N in a metal-organic framework in a solid state;

FIG. 3R: is an example according to various embodiments, illustrating a fluorescence spectra that was obtained with $\lambda_{ex}$=385 nm of the orange linker from FIG. 3N in a dilute solution;

FIG. 3S: is an example according to various embodiments, showing a photograph of the orange linker from FIG. 3n in a dilute solution under UV light;

Figure 1:
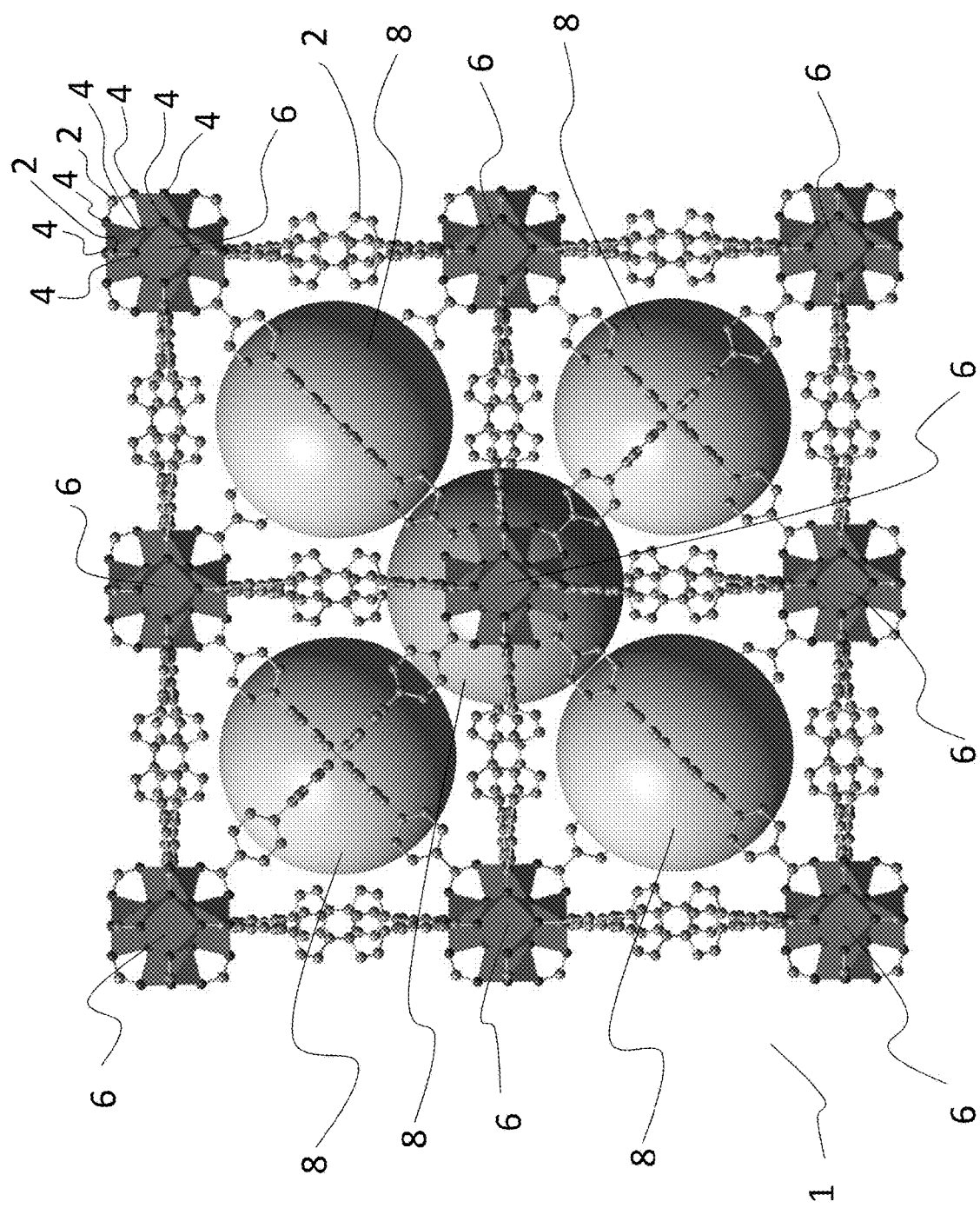
FIG. 1: is an example according to various embodiments, illustrating a schematic structure of a fragment of the crystal structure of a UiO MOF constructed with quaterphenyl-dicarboxylate.

It should be understood that the various embodiments are not limited to the examples illustrated in the figures.

DETAILED DESCRIPTION

Introduction and Definitions

Various embodiments may be understood more readily by reference to the following detailed description. Unless defined otherwise, all technical and scientific terms used herein have the same meaning as commonly understood by one of ordinary skill in the art to which this disclosure belongs.

As used herein, the term "standard temperature and pressure" generally refers to 20° C. and 1 atmosphere. Standard temperature and pressure may also be referred to as "ambient conditions." Unless indicated otherwise, parts are by weight, temperature is in ° C., and pressure is at or near atmospheric. The terms "elevated temperatures" or "high-temperatures" generally refer to temperatures of at least 100° C.

The term "mol percent", "mol %" or "mole percent" generally refers to the percentage that the moles of a particular component are of the total moles that are in a mixture. The sum of the mole fractions for each component in a solution is equal to 1.

References in the specification and concluding claims to parts by weight of a particular element or component in a composition denotes the weight relationship between the element or component and any other elements or components in the composition or article for which a part by weight is expressed. Thus, in a mixture containing 2 parts by weight of component X and 5 parts by weight component Y, X and Y are present at a weight ratio of 2:5, and are present in such ratio regardless of whether additional components are contained in the mixture.

A weight percent (wt. %) of a component, unless specifically stated to the contrary, is based on the total weight of the formulation or composition in which the component is included.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Throughout the description and claims of this specification the word "comprise" and other forms of the word, such as "comprising" and "comprises," means including but not limited to, and is not intended to exclude, for example, other additives, components, integers, or steps.

"Optional" or "optionally" means that the subsequently described event or circumstance can or cannot occur, and that the description includes instances where the event or circumstance occurs and instances where it does not.

It is understood that throughout this specification the identifiers "first" and "second" are used solely to aid in distinguishing the various components and steps of the disclosed subject matter. The identifiers "first" and "second" are not intended to imply any particular order, amount, preference, or importance to the components or steps modified by these terms.

As used herein, the term "composition" or "material" is intended to encompass a product comprising the specified ingredients in the specified amounts, as well as any product which results, directly or indirectly, from combination of the specified ingredients in the specified amounts.

As used herein, color names such as orange, red, green, and blue, are used as convenient references. The orange fluorophores according to various embodiments may emit at a wavelength of about 630 nm, which may, therefore, also have been termed a "red" fluorophore. The color names are representative, in other words, of ranges which may overlap. "Red" may be used to refer to a composition emitting at a wavelength interval of about 700 to about 635 nm and a frequency interval of about 430 to about 480 THz. "Orange" may be used to refer to a composition emitting at a wavelength interval of about 635 to about 590 nm and a frequency interval of about 480 to about 510 THz. Green" may be used to refer to a composition emitting at a wavelength interval of about 560 to about 520 nm and a frequency interval of about 540 to about 580 THz. Blue" may be used to refer to a composition emitting at a wavelength interval of about 490 to about 450 nm and a frequency interval of about 610 to about 670 THz.

It is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

All numeric values are herein assumed to be modified by the term "about," whether or not explicitly indicated. The term "about" generally refers to a range of numbers that one of skill in the art would consider equivalent to the recited value (i.e., having the same function or result). In many instances, the term "about" may include numbers that are rounded to the nearest significant figure.

Where a range of values is provided, it is understood that each intervening value, to the tenth of the unit of the lower limit (unless the context clearly dictates otherwise), between the upper and lower limit of that range, and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by prior disclosure. Further, the dates of publication provided could be different from the actual publication dates that may need to be independently confirmed.

Unless otherwise indicated, the present disclosure is not limited to particular materials, reagents, reaction materials, manufacturing processes, or the like, as such can vary. It is also to be understood that the terminology used herein is for purposes of describing particular embodiments only and is not intended to be limiting. It is also possible in the present disclosure that steps can be executed in different sequence where this is logically possible.

All the features disclosed in this specification (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

The examples and embodiments described herein are for illustrative purposes only and that various modifications or changes in light thereof will be suggested to persons skilled in the art and are to be included within the spirit and purview of this application. Many variations and modifications may be made to the above-described embodiment(s) of the disclosure without departing substantially from the spirit and principles of the disclosure. All such modifications and variations are intended to be included herein within the scope of this disclosure.

Reference will now be made in detail to specific aspects of the disclosed materials, compounds, compositions, articles, and methods, examples of which are illustrated in the accompanying Examples and Figures. The examples below are intended to further illustrate certain aspects of the methods and compounds described herein, and are not intended to limit the scope of the claims.

General Discussion

This invention discloses techniques for designing, and the synthesis, of materials that, among other functions, emit light and allow for fine-tuning of the light emission profile. This disclosure employs a class of materials commonly known as multivariate metal-organic frameworks (MTV MOF) whose primary building units are a mix of organic linkers with varied functional groups with a mix of metal ions. Multivariate MOFs are materials analogous to what is known in solid-state chemistry as "substitutional solid solutions," where ratios of atoms may vary in materials with the same parent structure [See: Wes, A. R. Basic Solid-State Chemistry. $2^{nd}$ Ed. 1999, John Wiley & Sons Ltd, The Atrium Souithern Gate, Chichester, West Sussex, P019 8SQ, England].

Multivariability in MOFs is possible because they contain large fractions of empty space in their crystal structure, as shown illustratively in FIG. 1, discussed in greater detail hereinafter. With the large fraction of empty space in the crystal structure, the steric constraint that would normally limit the size and number of substituents on the diverse building blocks can be alleviated without inducing polymorphism or undesired packing motifs. The only restriction required to prepare MTV MOFs is that the different linkers must be in similar size with respect to the connection points to the framework, to avoid distorting framework and keep the parent structure constant (See: FIG. 2).

By varying the ratios of light-emitting linkers in a MTV MOF the photophysical properties of the materials can be easily adjusted, resulting in behavior that can be customized to intended applications. For example, the linker type allows for the assembly of porous crystalline MOF materials, several kinds of mixed-linker MOFs, including but not limited to, pillared-layer mixed-linker MOFs, cage-directed mixed-linker MOFs, cluster-based mixed-linker MOFs, and structure templated mixed-linker MOFs.[1-3]

Although numerous MOFs are luminescent, said luminescence is the result of the fluorescence of a single linker, and thus, very few emit white light and their tunability for white light emission is challenging. According to certain embodiments, disclosed is a special class of metal-organic frameworks MTV MOF materials that emit white light with high degree of tunability, where the color of the emitted light depends exclusively on the ratio of linkers. Illustratively, a family of multivariate MOFs are disclosed where the linkers contain moieties that are fluorescent, and by appropriately varying the functionality and electronic structure in the fluorescent links different emission profiles can be observed. The combined emission properties of the combined emitters can be schematically adjusted solely by the ratio of red, green, blue, yellow, and orange emitting linkers in the framework. The combined emission from these materials mimics the fluorescent behavior that is usually observed only in solutions of mixed fluorophores.

The advantage of including the fluorescent links as part of the MVT-MOF framework is that such emitters behave as if dissolved in dilute solutions, because the color emitting centers are isolated, occupying well-defined crystallographic positions in the MOF unit cell thus minimizing electronic and physical interactions with other centers. An additional benefit of the wide open crystal structure is that the materials are unable to aggregate and phase separate, producing a homogeneous solid that will emit with similar spectral profile as observed in solution. The tailor-made frameworks produce broadband emission spectra in high efficiencies with emission mechanisms similar to those observed in dilute solutions.

Accordingly, certain embodiments disclosed herein pertain to the design and synthesis of multivariate metal-organic frameworks that produce white light with emission temperatures that range from cool to warm and can be systematically adjusted solely by the ratio of red, green, blue, yellow, and orange emitting linkers of the framework. The prepared frameworks produce broadband emission spectra in high efficiencies with emission mechanisms similar to those observed in dilute solutions.

Metal-organic frameworks (MOFs) are three dimensional crystalline materials built up from an organic part, the linker, and an inorganic part, the metal-oxide cluster. These hybrid materials are prepared by linking transition-metal centers through the coordination bonds and multidentate organic linkers which produce more structural variation leading to design new and unique materials. The structure of MOFs is characterized by an open framework that can be porous. Among their properties, metal-organic frameworks (MOFs) can facilitate storage, separation, transport and chemical transformation of chemical guests by accommodating the guest molecules, such as gases, ions, water and cognizable organic molecules, in well-defined pores. An illustrative MOF, called UiO-66 was synthesized from terephthalic acid and a zirconium-containing cluster has exceptional high surface area, thermal and chemical stability, which make the material an excellent candidate for many industrial applications.

Disclosed herein are MOFs capable of emitting light with high efficiency. By virtue of varying the functionality and electronic structure in the fluorescent links, different emission profiles are obtained, resulting in frameworks that combine the emission properties of the combined emitters. The combined emission mimics fluorescent behavior that is observed in liquid solutions of mixed fluorophores. The advantage of including the fluorescent links as part of the framework is that such emitters can behave as if dissolved in a dilute solution. The color emitting moieties are isolated, occupying well-defined crystallographic positions in the MOF unit cell, thus, they are unable to aggregate and phase separate, producing a homogeneous solid that will emit with similar spectral profile as observed in solution. The prepared frameworks can be specifically tailored to produce broadband emission spectra in high efficiencies with emission mechanisms similar to those observed in dilute solutions.

Embodiments described herein overcome the two main challenges for the systematic study of complex phenomena in molecular solids viz: the inability to extrapolate behavior of isolated molecules to the solid state, and the lack of predictability of their crystalline packing in the solid state, through the use of MOFs. The challenges arise because as the molecules pack, the structural electronic traits of an isolated molecule are modified by supramolecular interactions that dominate, and result in uncontrollable, unpredictable, or undesired behavior. MOFs offer the possibility of overcoming the current challenges and enabling a higher level of hierarchical complexity. This is possible because building blocks with varied chemical functionalization can be mixed and incorporated in a uniform framework in a multivariate (MTV) fashion [4]. Multivariability is a unique feature of MOFs and is possible because MOFs contain large fractions of empty space in their crystal structure, so the steric constraint from the diverse building blocks can be alleviated without inducing polymorphism or undesired packing motifs. The only restriction required to prepare MTV MOFs is that the different linkers must be in similar metric with respect to the connection points to the framework. Thus, by varying the ratios of linkers in a MTV MOF the photophysical properties can be easily adjusted, resulting in behavior that can be extrapolated from solution. Specific examples illustrated herein involve three MTV-MOFs that only differ in the inclusion of only 10 mol % of their linkers with fluorescent traots, resulting in bulk uniform materials that fluoresce with completely different colors.

Using a MOF isoreticular to UiO-66 with the organic linker tetramethyl-quaterphenyl-dicarboxylate (FIG. 2), which is non-fluorescent in the visible range (hereafter termed NF linker) and provides a structural backbone to allow multivariability, The central rings of the tetramethyl-quaterphenyl-dicarboxylate linker were modified orthogonally to its length to include fluorescent moieties that when incorporated in the MTV MOF, their chemical environment will resemble an isolated fluorescent molecule. A library of fluorophores have been deliberately crafted so each molecule exhibits customized properties, for example, to emit with a desired fluorescence profile, with specific lifetimes, quantum yields and absorption, that can be incorporated into the modified UiO-66-like long double interpenetrated or interweaved organic linkers frameworks, to create fluorophore centers surrounded by large pores. This arrangement preserves the fluorophores' unique properties even in the solid state.

The fluorescent linkers that include the highly emissive N,N'-diaryl-phenanthroimidazole moiety, which provide different emission profiles through proper functionalization have also been synthesized as disclosed herein. This system was chosen to allow the emissive traits to be easily adjusted without interference from potential energy transfer, as different fluorophores display absorption bands outside of the fluorescent region and the emission is enhanced by excited state proton transfer (ESPT). With this system no interference between the absorption and fluorescence of the linkers is expected.

In an illustrative embodiment, in Example 1, the fluorescent linkers Blue, Orange, and Green, as shown in FIG. 2, which in solution emits blue, orange, and green, respectively, have been prepared. Preparation of multivariate MOFs consisting of an input ratio of 90 mol % of NF linker with 10 mol % of either Blue, Orange, or Green linker, results in three highly crystalline MTV-MOFs (FIG. 3) with output ratios of 93 mol % NF and 7 mol % of either linkers that exhibit high fluorescence and emission profiles similar to those in solution.

A library of MTV MOFs in which the multivariability included two or the three fluorescent linkers (90 mol % input of NF linker) have been prepared (FIG. 3). The prepared MTV MOFs exhibit the fluorescence profiles that result from the linear combination of the linker compositions. In some embodiments, only small amount (less than 10 mol %) of the fluorescent linkers was incorporated into the MTV MOFs to ensure the isolation of the fluorescent moieties. This strategy resembles a dilute solution with no to minimal interactions between color centers and thus avoiding fluorescence quenching and crystallographic phase separation. This approach allowed fluorescence colors such as yellow (BG linkers), cyan (OG linkers) and even achieving white light (OB linkers).

In many embodiments, the temperature of the emitted white light is adjusted simply by adjusting the Orange:Blue linker ratio. For example, while 70:30 Orange:Blue ratio produced warm white light, a 30:70 Orange:Blue ratio produced to cool white light. By including all three OGB linkers, even more variability in the temperature of the white light was observed (FIG. 3). The expected photophysical properties can result from linear combination of the linker ratio, and thus a priori prediction of an expected emission profile can be easily performed. In yet another embodiment, the double interweaved framework ensures pairwise combinations of linkers to form dimer-like configurations which may exhibit excimer emission. These embodiments are first time that a homogeneous solid material has been shown to display tunable broadband emission.

Various embodiments relate to a composition comprising a metal-organic framework, the metal-organic framework may include at least one light-emitting linker in an amount sufficient for the composition to produce broadband emission spectra in high quantum yields. The metal-organic Framework may comprise clusters of $Zr_6O_4(OH)_4$ clusters connected through the organic linkers. An illustration of such a metal-organic framework is provided in FIG. 1, which will be discussed in greater detail hereinafter. The at least one light-emitting linker in an amount sufficient for the composition to produce broadband emission spectra in high quantum yields. As used herein, "quantum yield" is the ratio of photons absorbed to photons emitted through fluorescence. As used herein, the term "high quantum yield" refers to a quantum yield in a range of from about 4 to about 35%. For example, a high quantum yield may be within a range having a lower limit and/or an upper limit. The range may include or exclude the lower limit and/or the upper limit. The lower limit and/or upper limit can be selected from about 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, and 35. For example, according to certain embodiments, the high quantum yield me be in a range of from about 4 to about 35%, from about 10 to about 20%, or any combination of lower limits and upper limits described.

This amount may be as low as 0.1 mol % of a fluorescent link and fluorescence may still be observed. As used herein, broadband or white light is defined in the range between 400-800 nm wavelength.

According to various embodiments, the at least one light-emitting linker may be derived from a precursor, having a formula selected from:

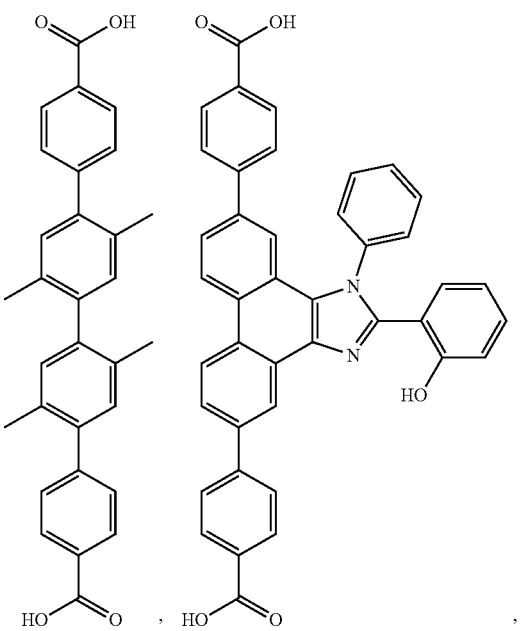

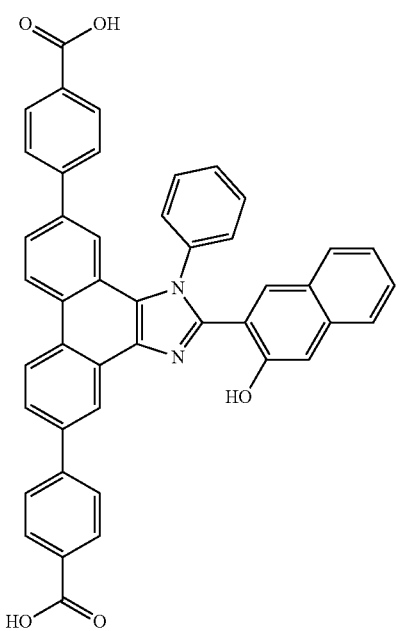

-continued

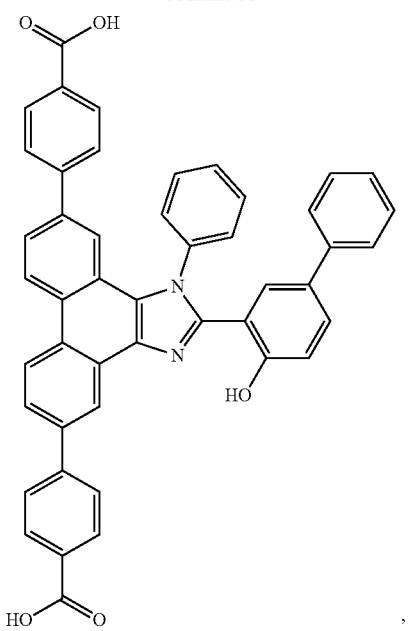

,

-continued

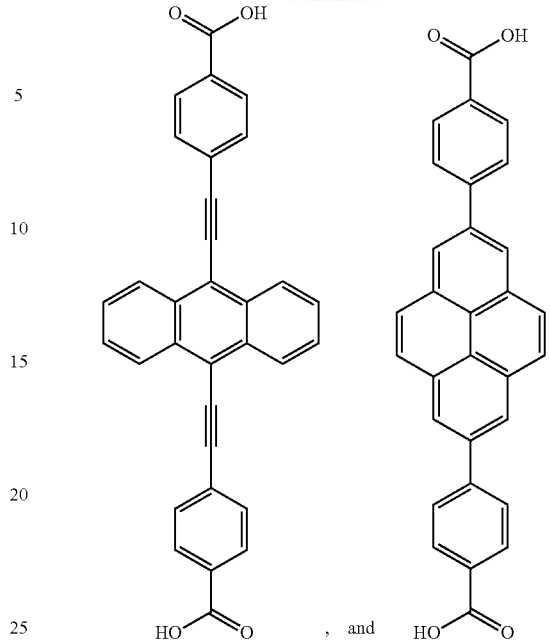

, and

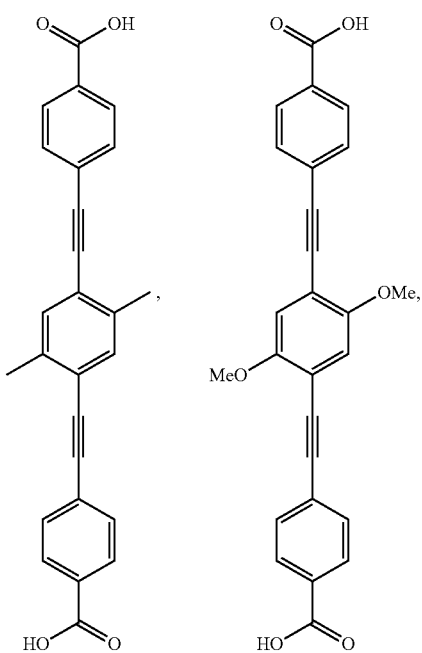

,

The composition may be a solid-state material. The composition may include a plurality of light-emitting linkers. The composition may exhibits a fluorescence spectrum based on a linear combination of the plurality of light emitting linkers. As used herein, the term "linear combination" means that the fluorescence of the material is the combined emission of each fluorophore link, if there is more orange link than blue link, the fluorescence will be more orange, according to the ratio of orange:blue.

According to various embodiments, the plurality of light-emitting linkers comprises one of the following combinations: a blue light-emitting linker and a green light-emitting linker to produce a yellow fluorescent color; an orange light-emitting linker and a green light-emitting linker to produce a cyan fluorescent color; and an orange light-emitting linker and a blue light-emitting linker to produce a white fluorescent color.

Various embodiments may provide a composition having an orange light-emitting linker, and a blue light-emitting linker in a ratio suitable to cause the synthetic, solid-state material to emit white light. White light being the combination of light between 400-800 nm. Any detectable light is considered white light, as long as it emits with broadband (400-800 nm). According to various embodiments, the ratio of orange light-emitting linker to blue light-emitting linker may be in a range of from 70:30 to 30:70 by mol %. The composition may achieve a spectra emission representative of light emitting linkers present in solution, meaning that the fluorophore links in solution have the same fluorescence spectrum than when incorporated in a MOF. According to various embodiments, the composition may have an architecture such that fluorescence quenching and crystallographic phase separation between light emitting linkers is reduced with respect to the same links when present in the solid state form (no MOF).

According to various embodiments, the composition may also include one or more non-fluorescent linkers. Central rings of the non-fluorescent linker may be modified orthogonally to its length to comprise the at least one light emitting linker such that when incorporated in the composition, the chemical environment of the light emitting linker comprises light emission properties of an isolated fluorescent molecule. A suitable non-fluorescent linker may have the formula:

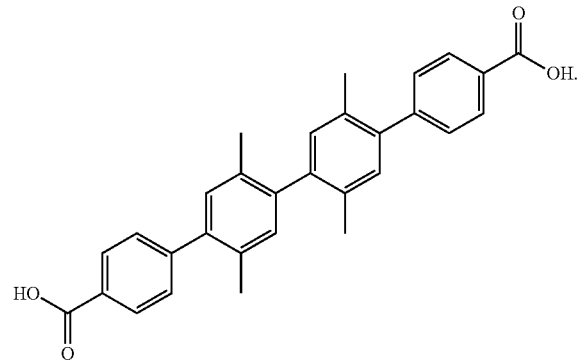 [SMILES: Cc1cc(-c2cc(C)c(-c3ccc(C(=O)O)cc3)cc2C)c(C)cc1-c1ccc(C(=O)O)cc1]

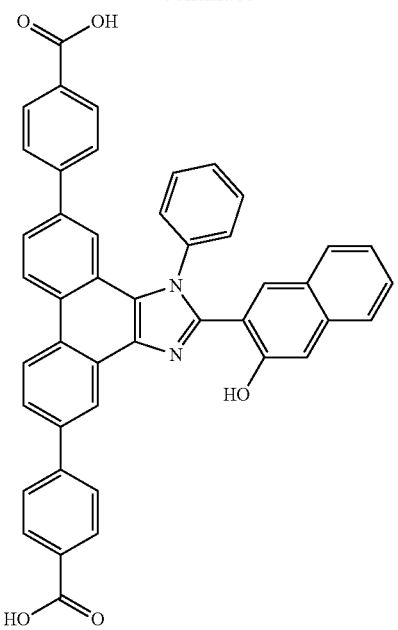

The non-fluorescent linker may comprise 90 mol percent or more of all linkers, wherein all linkers comprise the non-fluorescent linker and the at least one light-emitting linker. For example, the non-fluorescent linker may be present in an amount of 90-99 mol percent of all linkers.

Various embodiments relate to a method of producing a light-emitting metal-organic framework. The method may include combining at least one light-emitting linker precursor, having a formula selected from the group consisting of:

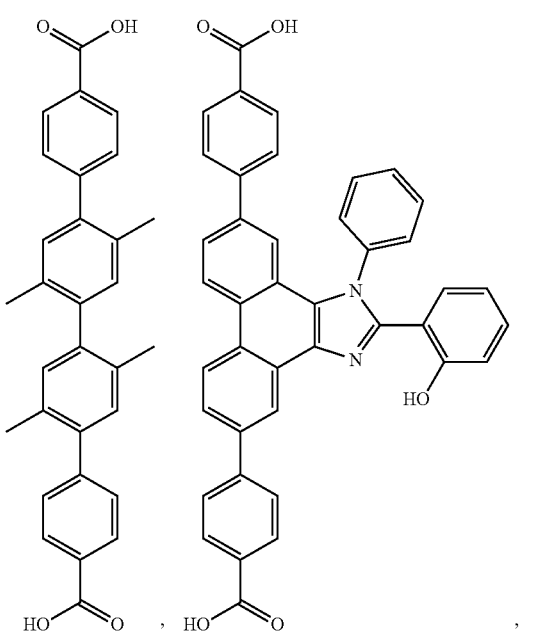

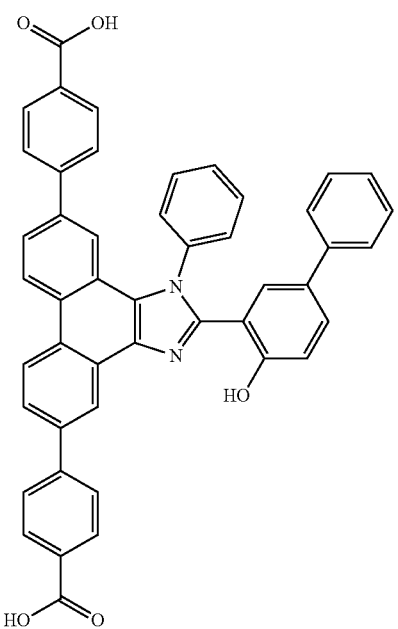

-continued

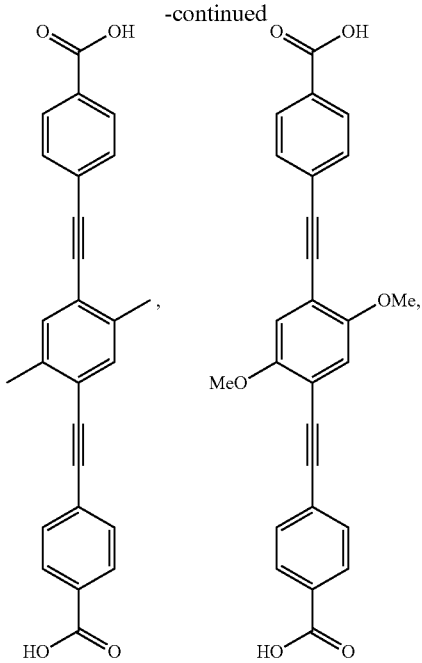

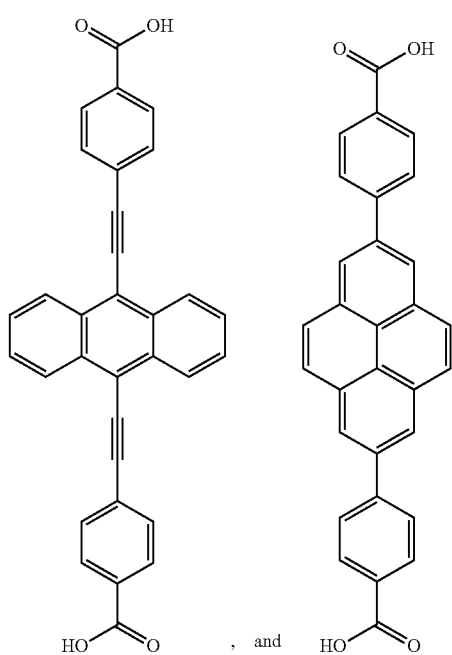 [SMILES: O=C(O)c1ccc(C#Cc2c3ccccc3c(C#Cc3ccc(C(=O)O)cc3)c3ccccc23)cc1 ; O=C(O)c1ccc(-c2cc3ccc4cc(-c5ccc(C(=O)O)cc5)cc5ccc(c2)c3c45)cc1]

with a non-fluorescent linker, having a formula:

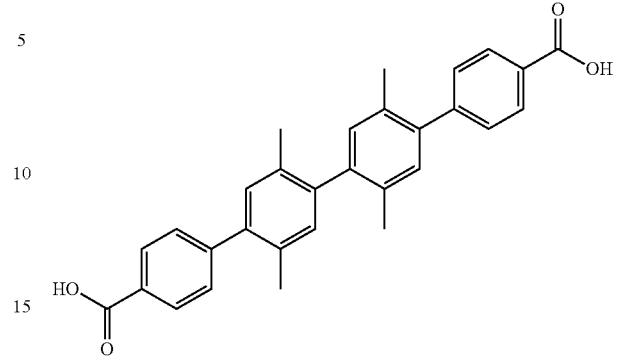

to form a first mixture; adding an acid to the first mixture to form a second mixture; and heating the second mixture. The step of heating the second mixture may include raising a temperature of the second mixture above 100 degrees Celsius, or to a temperature above 120 degrees Celsius. The heating of the second mixture may be conducted for a period of at least 4 hours, of at least 5 hours, of at least 6 hours or more. The step of adding the acid may be conducted under a stream of argon. The acid may be any suitable acid, such as acetic acid.

Discussion of FIG. 1

FIG. 1 is an example according to various embodiments, illustrating a schematic structure of a fragment 1 of the crystal structure of a UiO MOF constructed with quaterphenyl-dicarboxylate. In FIG. 1, the gray spheres 2 represent carbon atoms, the red spheres 4 represent oxygen atoms, the pink polyhedral structures 6 represent zirconium, and the yellow and orange spheres 8 represent empty spaces or pores within the crystal. The crystal structure illustrated in FIG. 1 was simulated in Materials Studio Modeling Software (v7.0) using the Forcite Module. Hydrogen atoms not shown for clarity. In lieu of labeling every atom in fragment 1, the carbon atoms 2 and the oxygen atoms 4 in the top, right-hand quadrant of the pink polyhedral structure 6 in the top, right-hand corner of the fragment 1 are labeled; as will be readily appreciated by persons having ordinary skill in the art, the structure of the remainder of the pink polyhedral structure 6 follows a similar pattern, as do the other pink polyhedral structures 6 that make up the fragment 1. The atoms connecting the pink polyhedral structures 6 are carbon atoms 2.

Discussion of FIGS. 2A-2I

FIG. 2A is an example according to various embodiments, illustrating a generalized schematic diagram 20 of a chemical structure of a linker, showing the restrictions on linker design for multivariability. Each linker structure may have a first connection point 22 and a second connection point 24 by which the linker structure may be connected to an overall chemical framework (not shown). It will be understood by persons having ordinary skill in the art that the first connection point 22 and the second connection point may be chemical moieties, such as a carboxylic acid group. Between the first connection point 22 and the second connection point 24 may be a further chemical structure 26, which may provide structural variability and/or fluorescent variability. It will be understood by persons having ordinary skill in the art that the further chemical structure 26 may be a variety of chemical structures, for example, such as the structures illustrated in FIGS. 2B-2I. Various embodiments of the further chemical structure 26 may exhibit differing fluorescent properties and may also have different structural features, such as length 28. Length 28 is a representation of the distance between the first connection point 22 and the second connection point 24. A variety of examples of length 28 (in Å) are provided for the various structures shown in FIGS. 2B-2I. In FIGS. 2C-2I, a percent deviation in distance with respect to the NF linker, shown in FIG. 2B is also given.

FIG. 2B is an example according to various embodiments, illustrating a chemical structure of an organic linker utilized for UiO-type MOFs in the illustrative embodiments and displaying its abbreviation "NF", used for reference in this disclosure. The length 28 shown for this particular linker is 18.665 Å.

FIG. 2C is an example according to various embodiments, illustrating a chemical structure of an organic linker utilized for UiO-type MOFs in the illustrative embodiments and displaying its abbreviation "Blue", used for reference in this disclosure. The length 28 shown for this particular linker is 18.702 Å, which represents an increase of 0.2% relative to the NF linker shown in FIG. 2B.

FIG. 2D is an example according to various embodiments, illustrating a chemical structure of an organic linker utilized for UiO-type MOFs in the illustrative embodiments and displaying its abbreviation "Orange", used for reference in this disclosure. The length 28 shown for this particular linker is 18.702 Å, which represents a variation of 0.2% relative to the NF linker shown in FIG. 2B.

FIG. 2E is an example according to various embodiments, illustrating a chemical structure of an organic linker utilized for UiO-type MOFs in the illustrative embodiments and displaying its abbreviation "Green", used for reference in this disclosure. The length 28 shown for this particular linker is 18.702 Å, which represents a variation of 0.2% relative to the NF linker shown in FIG. 2B.

FIG. 2F is an example according to various embodiments, illustrating a chemical structure of an organic linker utilized for UiO-type MOFs in the illustrative embodiments and displaying its abbreviation "Xy", used for reference in this disclosure. The length 28 shown for this particular linker is 19.574 Å, which represents a variation of 4.9% relative to the NF linker shown in FIG. 2B.

FIG. 2G is an example according to various embodiments, illustrating a chemical structure of an organic linker utilized for UiO-type MOFs in the illustrative embodiments and displaying its abbreviation "Dm", used for reference in this disclosure. The length 28 shown for this particular linker is 19.562 Å, which represents a variation of 4.8% relative to the NF linker shown in FIG. 2B.

FIG. 2H is an example according to various embodiments, illustrating a chemical structure of an organic linker utilized for UiO-type MOFs in the illustrative embodiments and displaying its abbreviation "An", used for reference in this disclosure. The length 28 shown for this particular linker is 19.617 Å, which represents a variation of 5.1% relative to the NF linker shown in FIG. 2B.

FIG. 2I is an example according to various embodiments, illustrating a chemical structure of an organic linker utilized for UiO-type MOFs in the illustrative embodiments and displaying its abbreviation "Py", used for reference in this disclosure. The length 28 shown for this particular linker is 18.632 Å, which represents a variation of 0.2% relative to the NF linker shown in FIG. 2B.

Discussion of FIGS. 3A-S

FIG. 3 illustrates various embodiments of multivariate MOFs that contain NF linker and either Blue (See FIG. 2C), Green (See FIG. 2E) or Orange (See FIG. 2D) linkers resulting in solid materials with emissive properties of the corresponding diester linkers in solution, as well as, respective optical images under UV light and fluorescence spectra that were obtained with $\lambda_{ex}$=385 nm (star indicate emission signal from the non-hydrogen bonded conformer).

Taken together FIGS. 3A, 3B, 3C, 3D, 3E, 3F, and 3G illustrate a method of producing a multivariate blue MOF and the results obtained. FIG. 3A is an example according to various embodiments, illustrating a step of providing 93 mol % of the non-fluorescent NF linker from FIG. 2B. FIG. 3B is an example according to various embodiments, illustrating a step of adding 7 mol % of the blue linker from FIG. 2C to the non-fluorescent NF linker provided in the step illustrated in FIG. 3A. FIG. 3C is an example according to various embodiments, showing a photograph of the blue linker from FIG. 3B in a metal-organic framework (MOF) under UV light. FIG. 3D is an example according to various embodiments, illustrating the blue linker from FIG. 3B in a metal-organic framework. FIG. 3E is an example according to various embodiments, illustrating a fluorescence spectra that was obtained with $\lambda_{ex}$=385 nm of the blue linker from FIG. 3B in a metal-organic framework in a solid state. FIG. 3F is an example according to various embodiments, illustrating a fluorescence spectra that was obtained with $\lambda_{ex}$=385 nm of the blue linker from FIG. 3B in a dilute solution. FIG. 3G is an example according to various embodiments, showing a photograph of the blue linker from FIG. 3B in a dilute solution under UV light.

Taken together FIGS. 3A, 3H, 3I, 3J, 3K, 3L, and 3M illustrate a method of producing a multivariate green MOF and the results obtained. FIG. 3A is an example according to various embodiments, illustrating a step of providing 93 mol % of the non-fluorescent NF linker from FIG. 2B. FIG. 3H is an example according to various embodiments, illustrating a step of adding 7 mol % of the green linker from FIG. 2E to the non-fluorescent NF linker provided in the step illustrated in FIG. 3A. FIG. 3I is an example according to various embodiments, showing a photograph of the green linker from FIG. 3H in a metal-organic framework under UV light. FIG. 3J is an example according to various embodiments, illustrating the green linker from FIG. 3H in a metal-organic framework. FIG. 3K is an example according to various embodiments, illustrating a fluorescence spectra that was obtained with $\lambda_{ex}$=385 nm of the green linker from FIG. 3H in a metal-organic framework in a solid state. FIG. 3L is an example according to various embodiments, illustrating a fluorescence spectra that was obtained with $\lambda_{ex}$=385 nm of the green linker from FIG. 3H in a dilute solution. FIG. 3M is an example according to various embodiments, showing a photograph of the green linker from FIG. 3H in a dilute solution under UV light.

Taken together FIGS. 3A, 3N, 3O, 3P, 3QE, 3R, and 3S illustrate a method of producing a multivariate orange MOF and the results obtained. FIG. 3A is an example according to various embodiments, illustrating a step of providing 93 mol % of the non-fluorescent NF linker from FIG. 2B. FIG. 3N is an example according to various embodiments, illustrating a step of adding 7 mol % of the orange linker from FIG. 2D to the non-fluorescent NF linker provided in the step illustrated in FIG. 3A. FIG. 3O is an example according to various embodiments, showing a photograph of the orange linker from FIG. 3N in a metal-organic framework under UV light. FIG. 3P is an example according to various embodiments, illustrating the orange linker from FIG. 3N in a metal-organic framework. FIG. 3Q is an example according to various embodiments, illustrating a fluorescence spectra that was obtained with $\lambda_{ex}$=385 nm of the orange linker from FIG. 3N in a metal-organic framework in a solid state. FIG. 3R is an example according to various embodiments, illustrating a fluorescence spectra that was obtained with $\lambda_{ex}$=385 nm of the orange linker from FIG. 3N in a dilute solution. FIG. 3S is an example according to various embodiments, showing a photograph of the orange linker from FIG. 3n in a dilute solution under UV light.

Discussion of FIGS. 4A-E

Figure 4A:
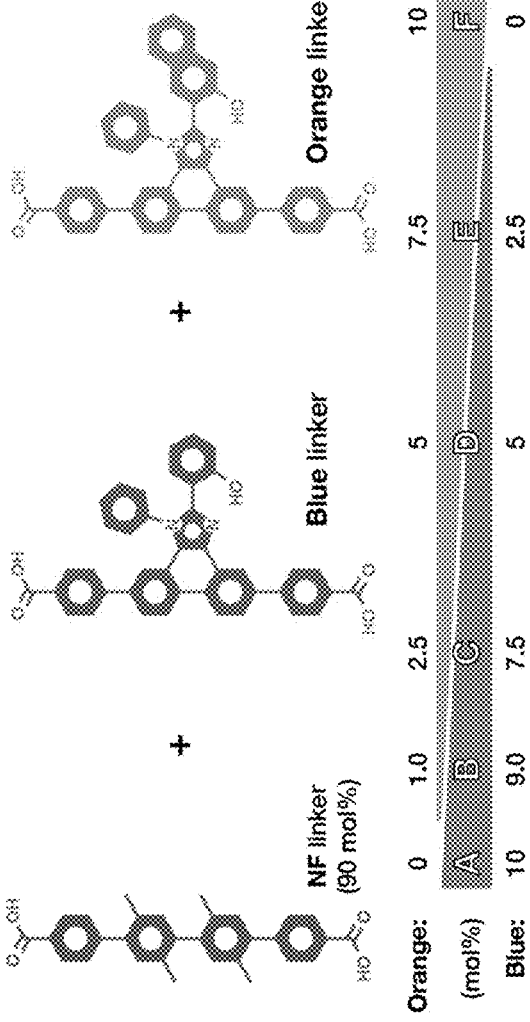
FIG. 4A: is an example according to various embodiments, illustrating a combination of 90 mol % NF linker, with varying amounts of blue linker and/or orange linker.
Figure 4B:
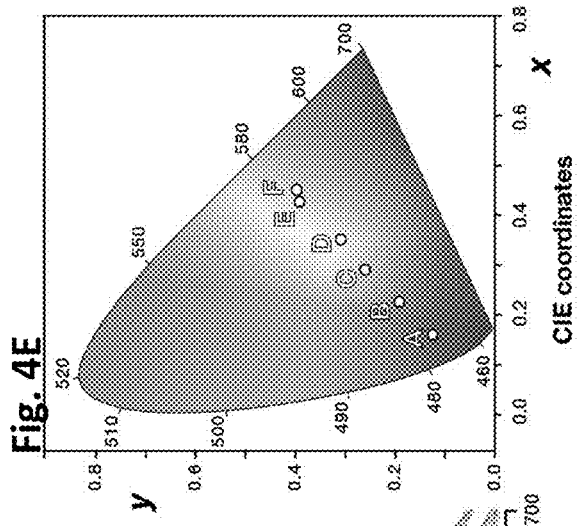
FIG. 4B: is an example according to various embodiments, illustrating a scale showing a scale of ratios of orange linker and blue linker in the combination shown in FIG. 4A, with six specific ratios identified as points A, B, C, D, E, and F on the scale.
Figure 4C:
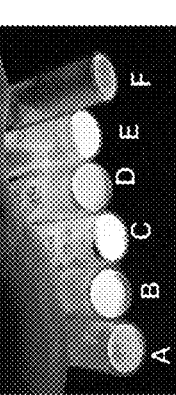
FIG. 4C: is an example according to various embodiments, showing a photograph under UV light of combinations at the ratios identified as points A, B, C, D, E, and F in FIG. 4B.
Figure 4D:
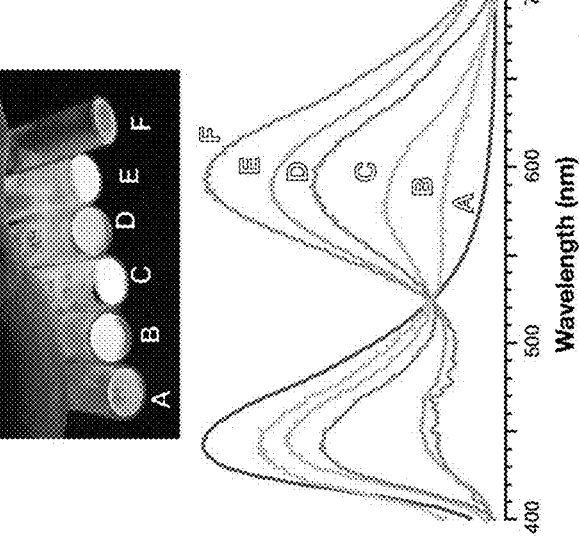
FIG. 4D: is an example according to various embodiments, illustrating fluorescence spectra for each of the combinations at the ratios identified as points A, B, C, D, E, and F in FIG. 4B.
Figure 4E:
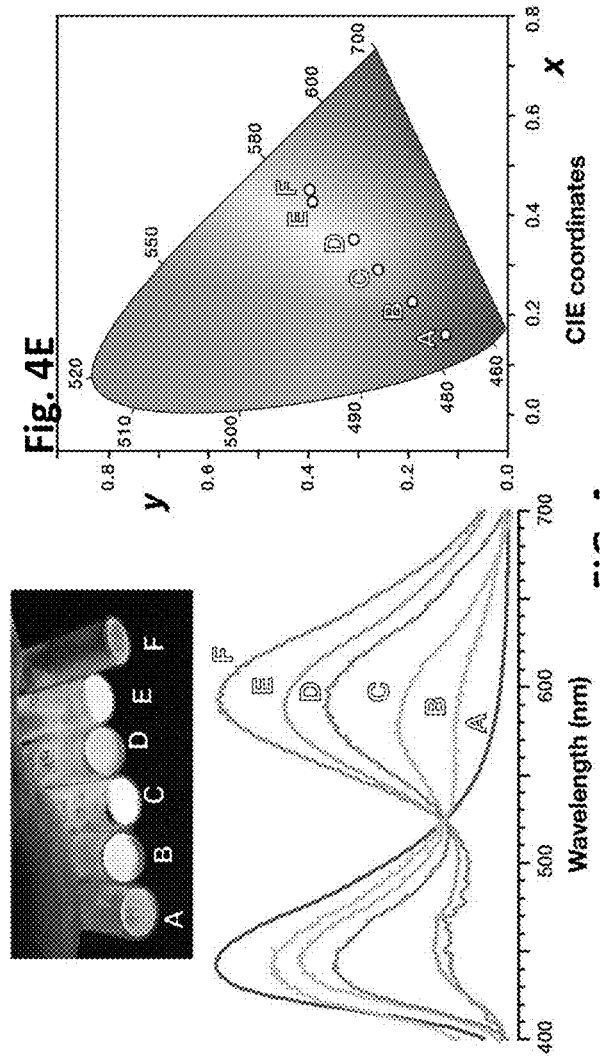
FIG. 4E: is an example according to various embodiments, illustrating a chart showing the CIE chromaticity coordinates for each of the combinations at the ratios identified as points A, B, C, D, E, and F in FIG. 4B.

FIG. 4A is an example according to various embodiments, illustrating a combination of 90 mol % NF linker, with varying amounts of blue linker and/or orange linker. FIG. 4B is an example according to various embodiments, illustrating a scale showing a scale of ratios of orange linker and blue linker in the combination shown in FIG. 4A, with six specific ratios identified as points A, B, C, D, E, and F on the scale. Point A represents a ratio of 0 mol % orange linker and 10 mol % blue linker in combination with the previously mentioned 90 mol % NF linker. Point B represents a ratio of 1.0 mol % orange linker and 9.0 mol % blue linker in combination with 90 mol % NF linker. Point C represents a ratio of 2.5 mol % orange linker and 7.5 mol % blue linker in combination with 90 mol % NF linker. Point D represents a ratio of 5 mol % orange linker and 5 mol % blue linker in combination with 90 mol % NF linker. Point E represents a ratio of 7.5 mol % orange linker and 2.5 mol % blue linker in combination with 90 mol % NF linker. Point F represents a ratio of 10 mol % orange linker and 0 mol % blue linker in combination with 90 mol % NF linker. It should be understood that the present disclosure is not limited to the specific ratios listed, but includes all combinations and subranges. FIG. 4C is an example according to various embodiments, showing a photograph under UV light of combinations at the ratios identified as points A, B, C, D, E, and F in FIG. 4B. FIG. 4D is an example according to various embodiments, illustrating fluorescence spectra for each of the combinations at the ratios identified as points A, B, C, D, E, and F in FIG. 4B. FIG. 4E is an example according to various embodiments, illustrating a chart showing the CIE chromaticity coordinates for each of the combinations at the ratios identified as points A, B, C, D, E, and F in FIG. 4B.

Figure 5:
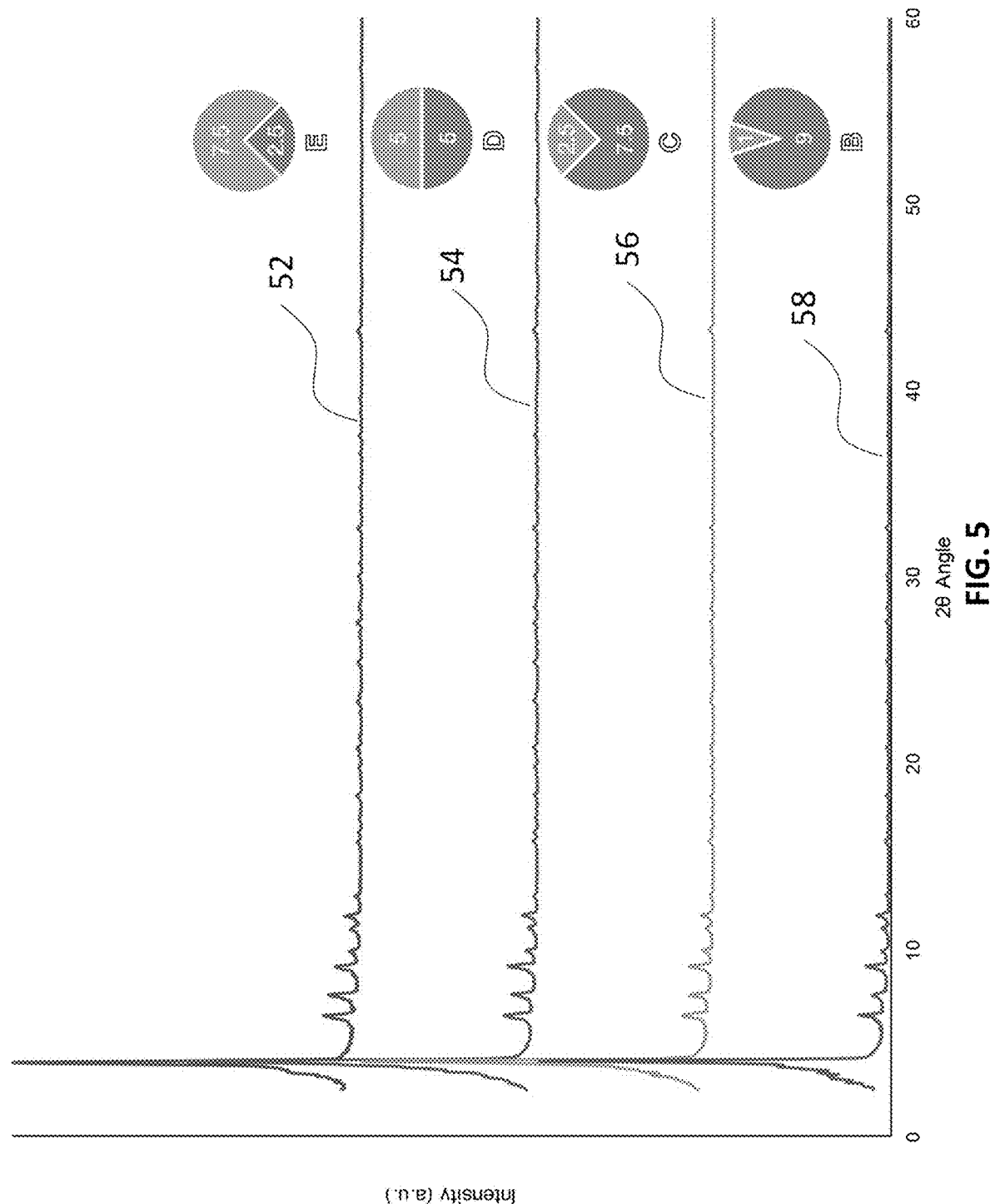
FIG. 5: is an example, illustrating powder X-Ray patterns for various embodiments.

Discussion of FIG. 5

X-ray powder diffraction (XRD) is a rapid analytical technique primarily used for phase identification of a crystalline material and can provide information on unit cell dimensions. The analyzed material may be finely ground, homogenized, and average bulk composition may be determined. FIG. 5 is an example according to various embodiments, illustrating: characteristic powder X-Ray (XRD) spectra of various embodiments. FIG. 5 includes a powder X-Ray pattern 52 of a 90% NF (based on a linker structurally illustrated in FIG. 2B), 2.5% blue (based on a linker structurally illustrated in FIG. 2C), 7.5% orange MOF (based on a linker structurally illustrated in FIG. 2D); a powder X-Ray spectrum 54 of a combination of a 90% NF (based on a linker structurally illustrated in FIG. 2B), 5% blue (based on a linker structurally illustrated in FIG. 2C), 5% orange (based on a linker structurally illustrated in FIG. 2D) MOF; a powder X-Ray spectrum 56 of a 90% NF (based on a linker structurally illustrated in FIG. 2B), 7.5% blue (based on a linker structurally illustrated in FIG. 2C), 2.5% orange (based on a linker structurally illustrated in FIG. 2D) MOF; and a powder X-Ray spectrum 58 of a 90% NF (based on a linker structurally illustrated in FIG. 2B), 9% blue (based on a linker structurally illustrated in FIG. 2C), 1% orange (based on a linker structurally illustrated in FIG. 2D) MOF.

Figure 6:
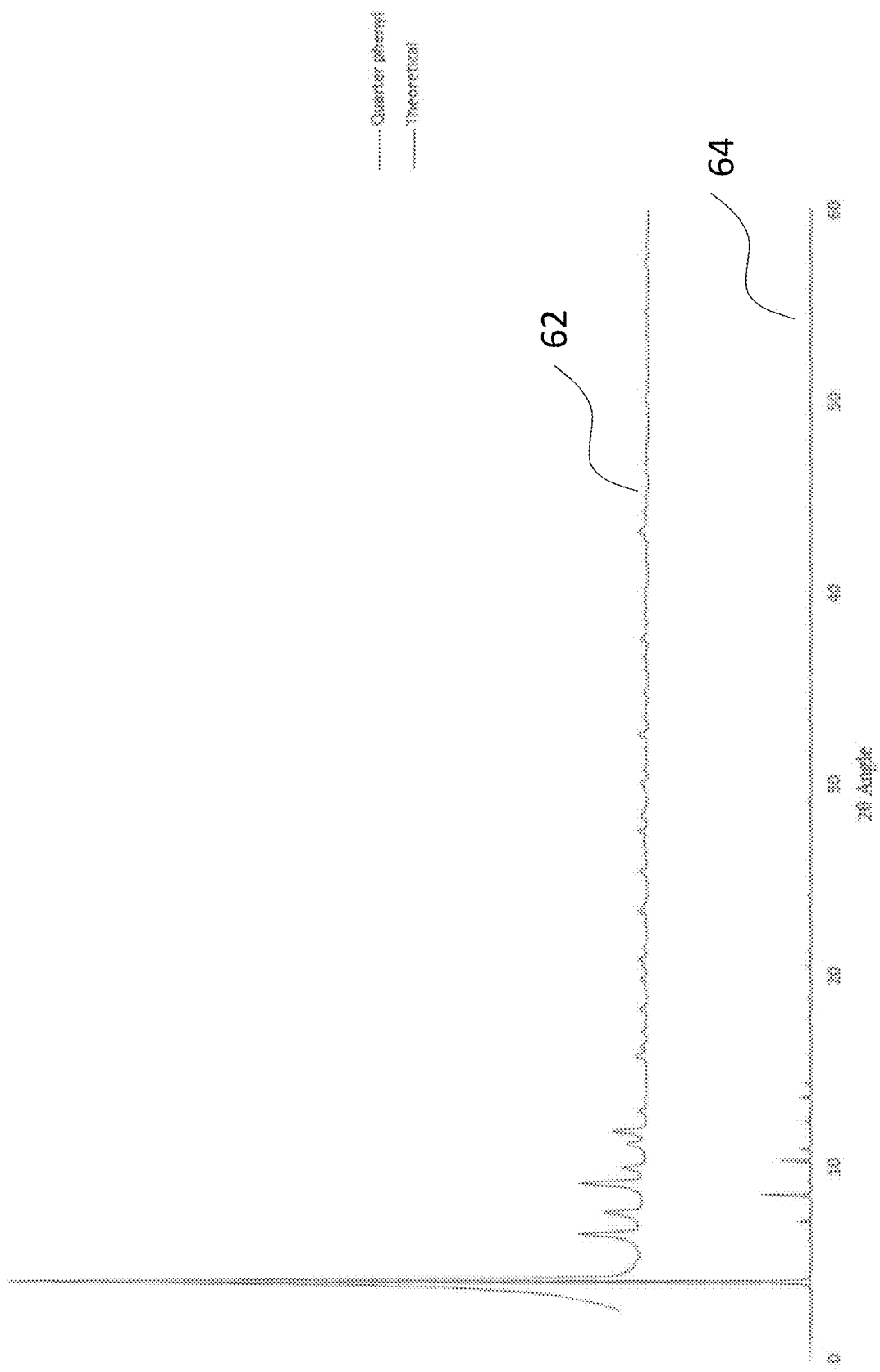
FIG. 6: is an example, illustrating powder X-Ray patterns for various embodiments.

Discussion of FIG. 6

FIG. 6 is an example according to various embodiments, illustrating characteristic powder X-Ray (XRD) patterns of various embodiments. FIG. 6 includes a powder X-Ray pattern 62 of an NF MOF (based on a linker structurally illustrated in FIG. 2B); and a theoretical powder X-Ray pattern 64 for the compound, demonstrating a close match.

Figure 7:
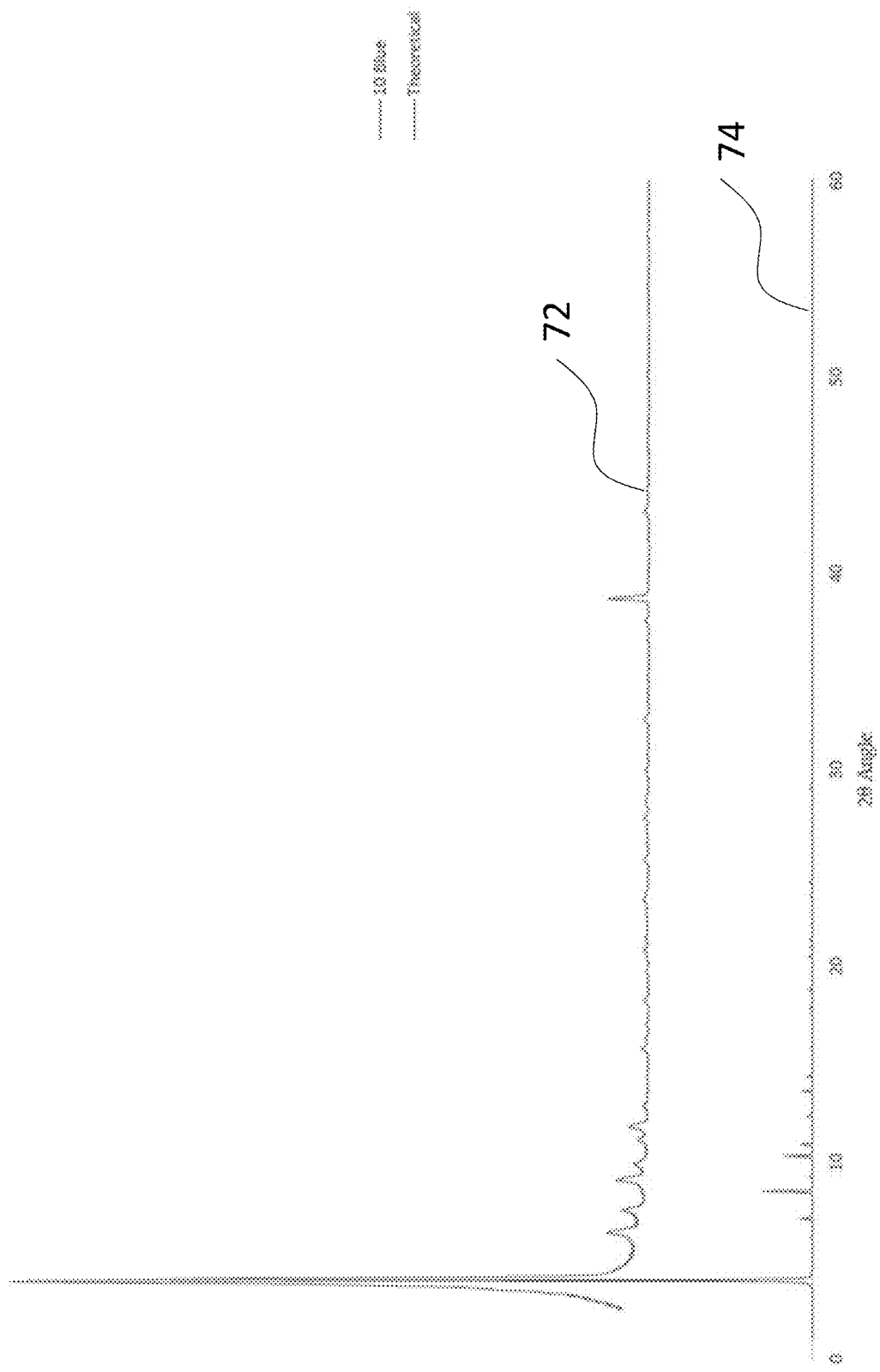
FIG. 7: is an example, illustrating powder X-Ray patterns for various embodiments.

Discussion of FIG. 7

FIG. 7 is an example according to various embodiments, illustrating characteristic powder X-Ray (XRD) patterns of various embodiments. FIG. 7 includes a powder X-Ray pattern 72 of a combination of 10 mol % blue MOF (based on a linker structurally illustrated in FIG. 2C) with 90 mol % NF MOF (based on a linker structurally illustrated in FIG. 2B); and a theoretical powder X-Ray pattern 74 for the compound, demonstrating a close match.

Figure 8:
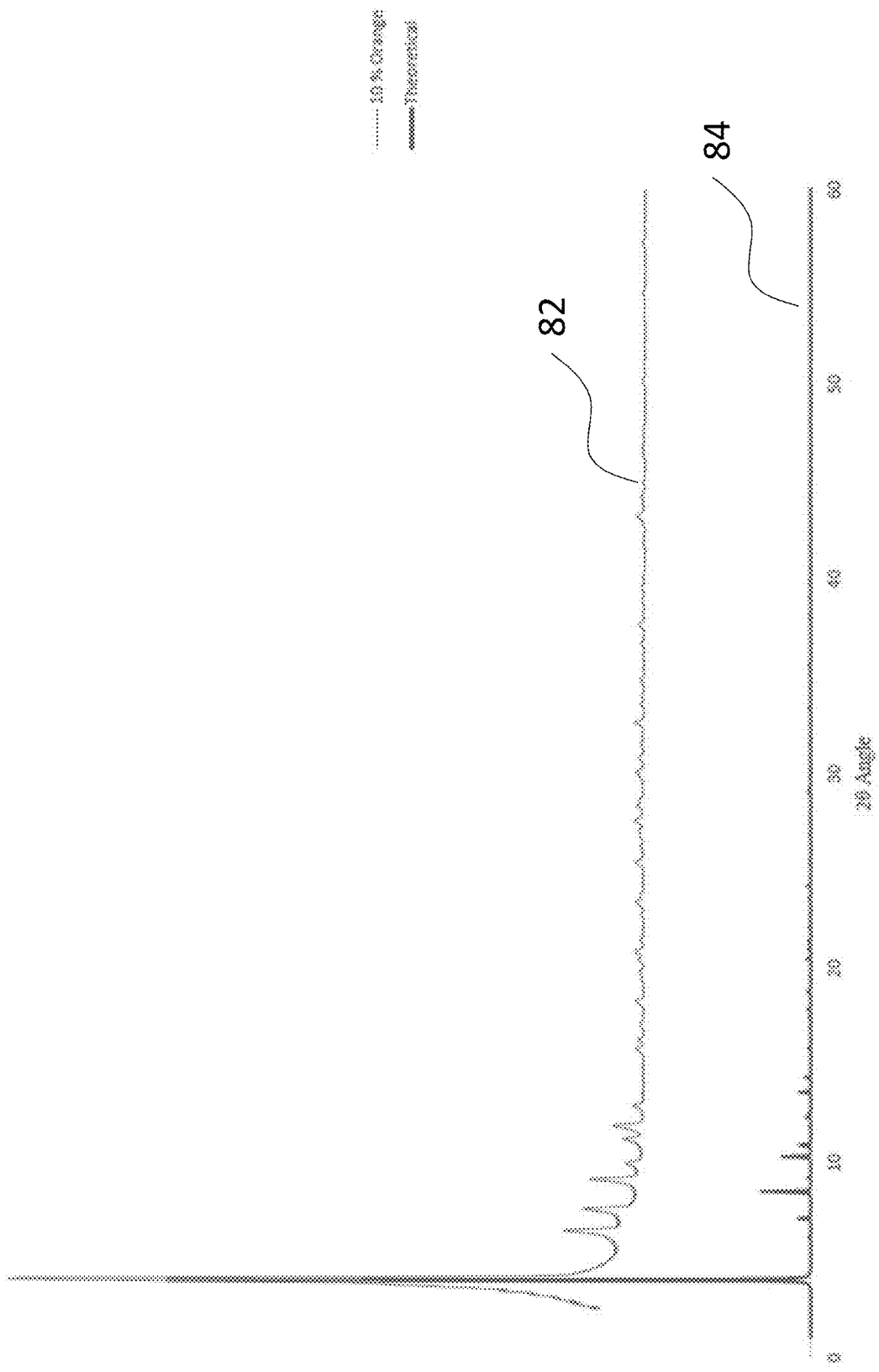
FIG. 8: is an example, illustrating powder X-Ray patterns for various embodiments.

Discussion of FIG. 8

FIG. 8 is an example according to various embodiments, illustrating characteristic powder X-Ray (XRD) patterns of various embodiments. FIG. 8 includes a powder X-Ray pattern 82 of a combination of 10 mol % orange MOF (based on a linker structurally illustrated in FIG. 2D) with 90 mol % NF MOF (based on a linker structurally illustrated in FIG. 2B); and a theoretical powder X-Ray pattern 84 for the compound, demonstrating a close match.

Figure 9:
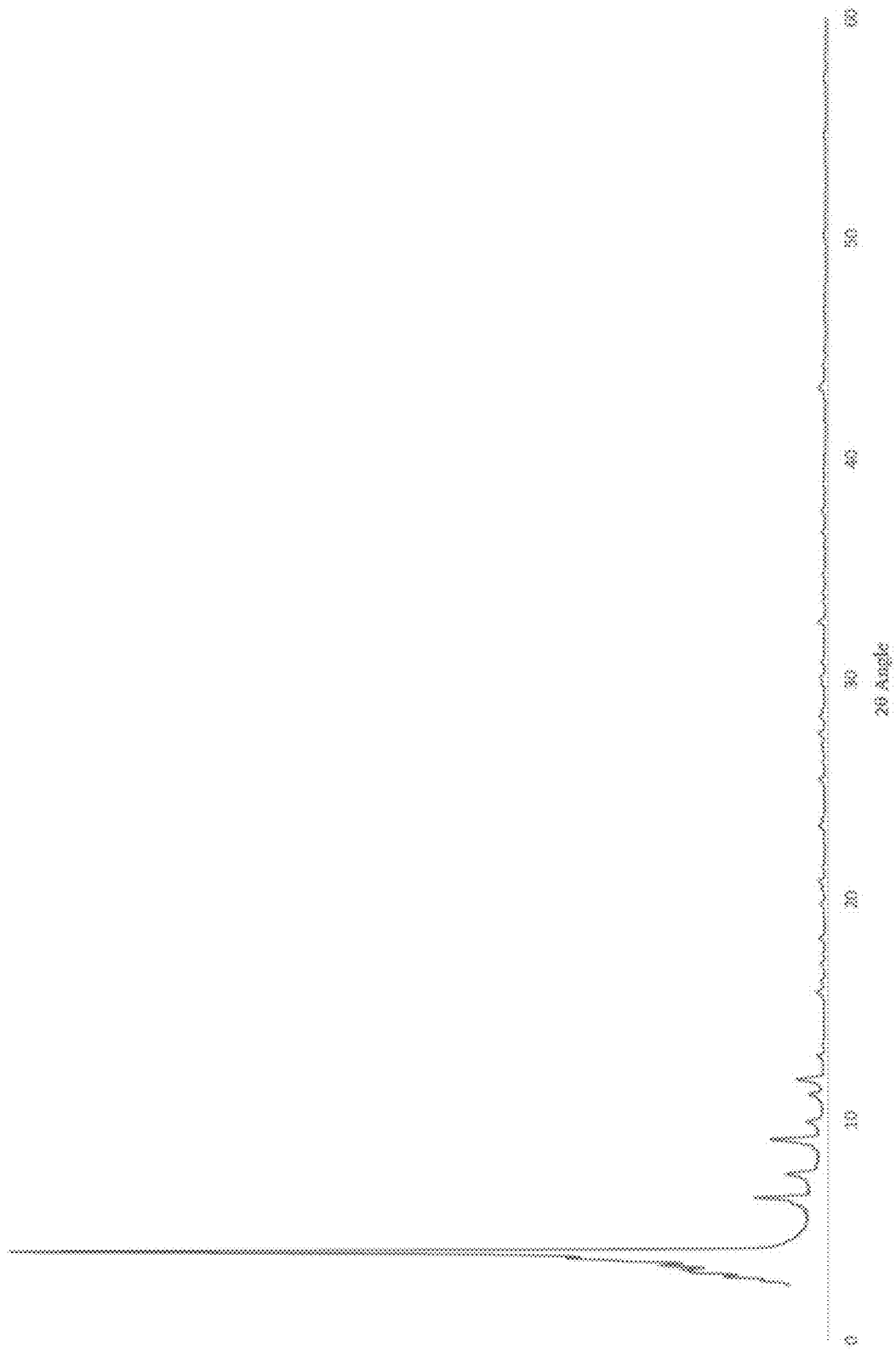
FIG. 9: is an example, illustrating a powder X-Ray pattern for various embodiments.

Discussion of FIG. 9

FIG. 9 is an example according to various embodiments, illustrating a characteristic powder X-Ray (XRD) pattern of a combination of 9 mol % blue MOF (based on a linker structurally illustrated in FIG. 2C); 1 mol % orange MOF (based on a linker structurally illustrated in FIG. 2D); and 90 mol % NF MOF (based on a linker structurally illustrated in FIG. 2B).

Figure 10:
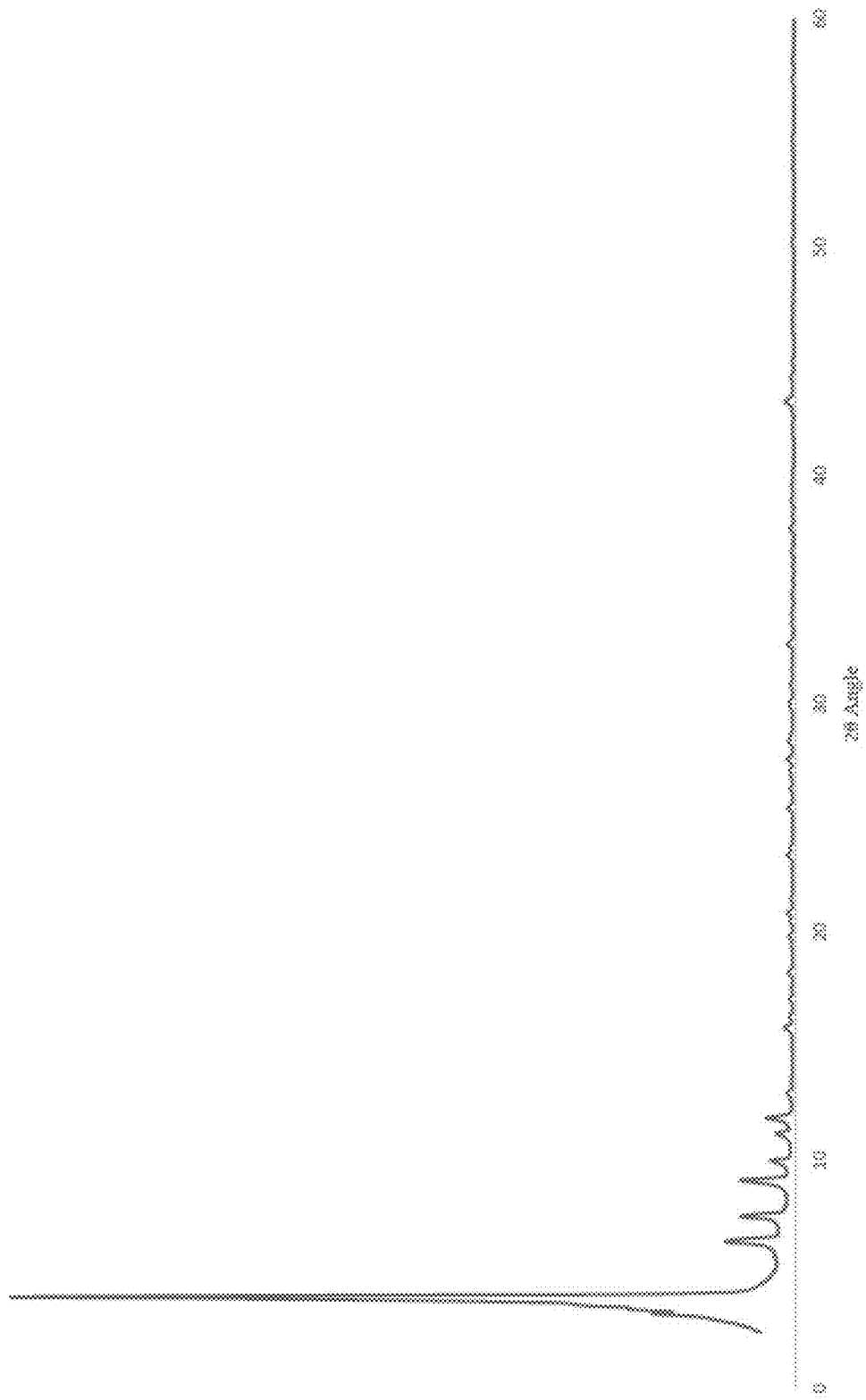
FIG. 10: is an example, illustrating a powder X-Ray pattern for various embodiments.

Discussion of FIG. 10

FIG. 10 is an example according to various embodiments, illustrating a characteristic powder X-Ray (XRD) pattern of a combination of 7.5 mol % blue MOF (based on a linker structurally illustrated in FIG. 2C); 2.5 mol % orange MOF (based on a linker structurally illustrated in FIG. 2D); and 90 mol % NF MOF (based on a linker structurally illustrated in FIG. 2B).

Figure 11:
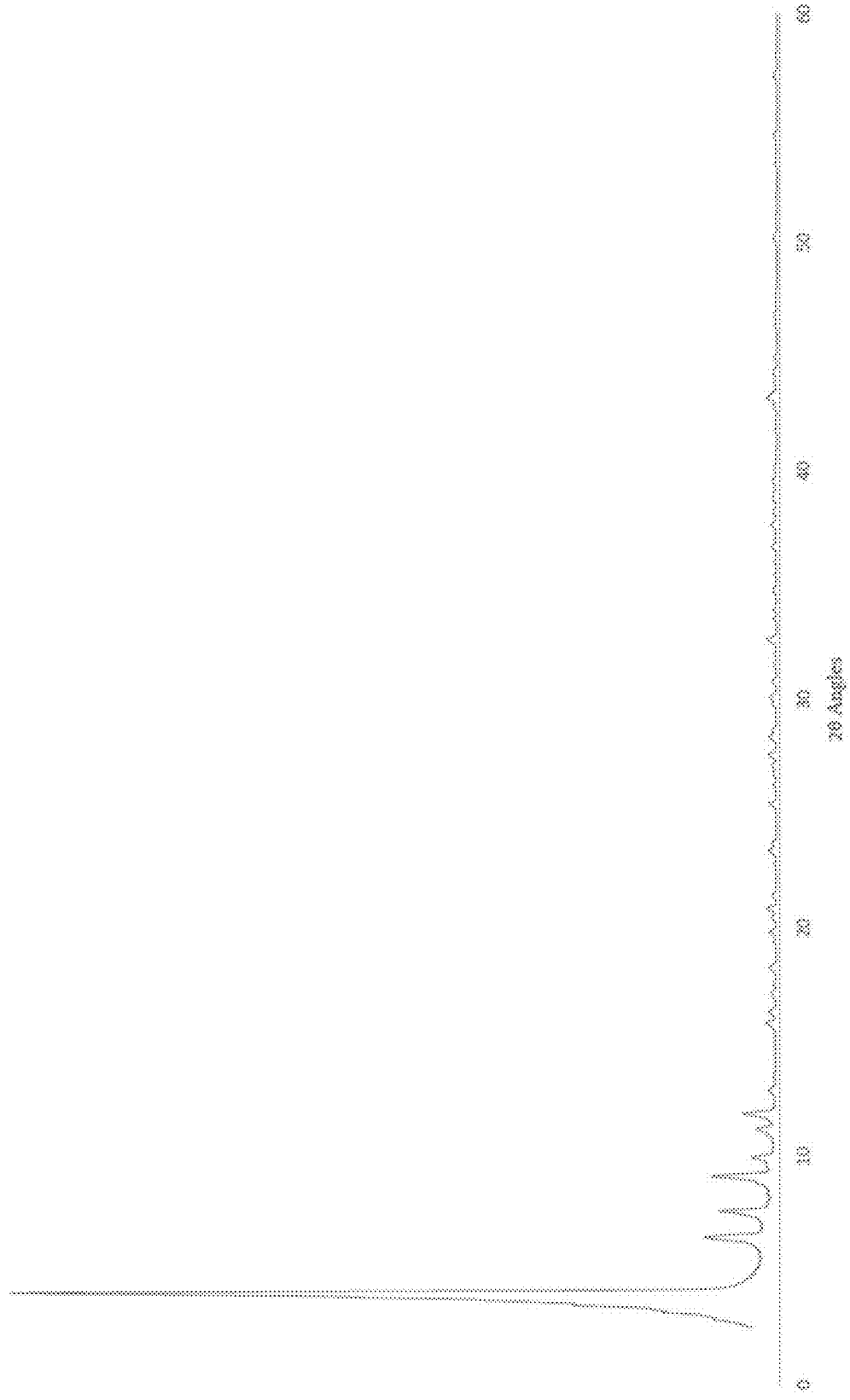
FIG. 11: is an example, illustrating a powder X-Ray pattern for various embodiments.

Discussion of FIG. 11

FIG. 11 is an example according to various embodiments, illustrating a characteristic powder X-Ray (XRD) pattern of a combination of 5 mol % blue MOF (based on a linker structurally illustrated in FIG. 2C); 5 mol % orange MOF (based on a linker structurally illustrated in FIG. 2D); and 90 mol % NF MOF (based on a linker structurally illustrated in FIG. 2B).

Figure 12:
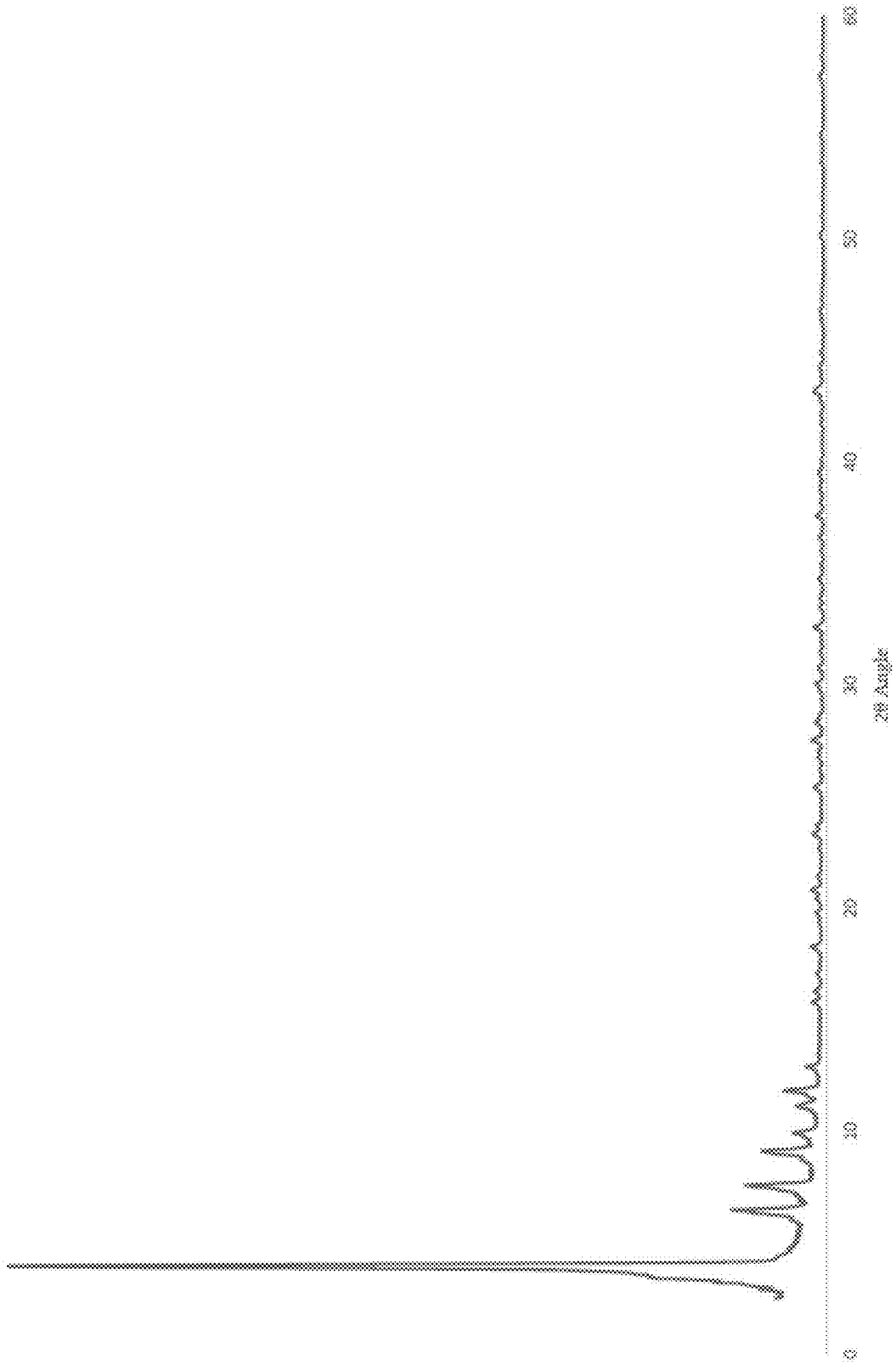
FIG. 12: is an example, illustrating a powder X-Ray pattern for various embodiments.

Discussion of FIG. 12

FIG. 12 is an example according to various embodiments, illustrating a characteristic powder X-Ray (XRD) pattern of a combination of 2.5 mol % blue MOF (based on a linker structurally illustrated in FIG. 2C); 7.5 mol % orange MOF (based on a linker structurally illustrated in FIG. 2D); and 90 mol % NF MOF (based on a linker structurally illustrated in FIG. 2B).

Discussion of FIGS. 13-18

FIGS. 13-18 are described above and are referenced in the following Examples.

Figure 19:
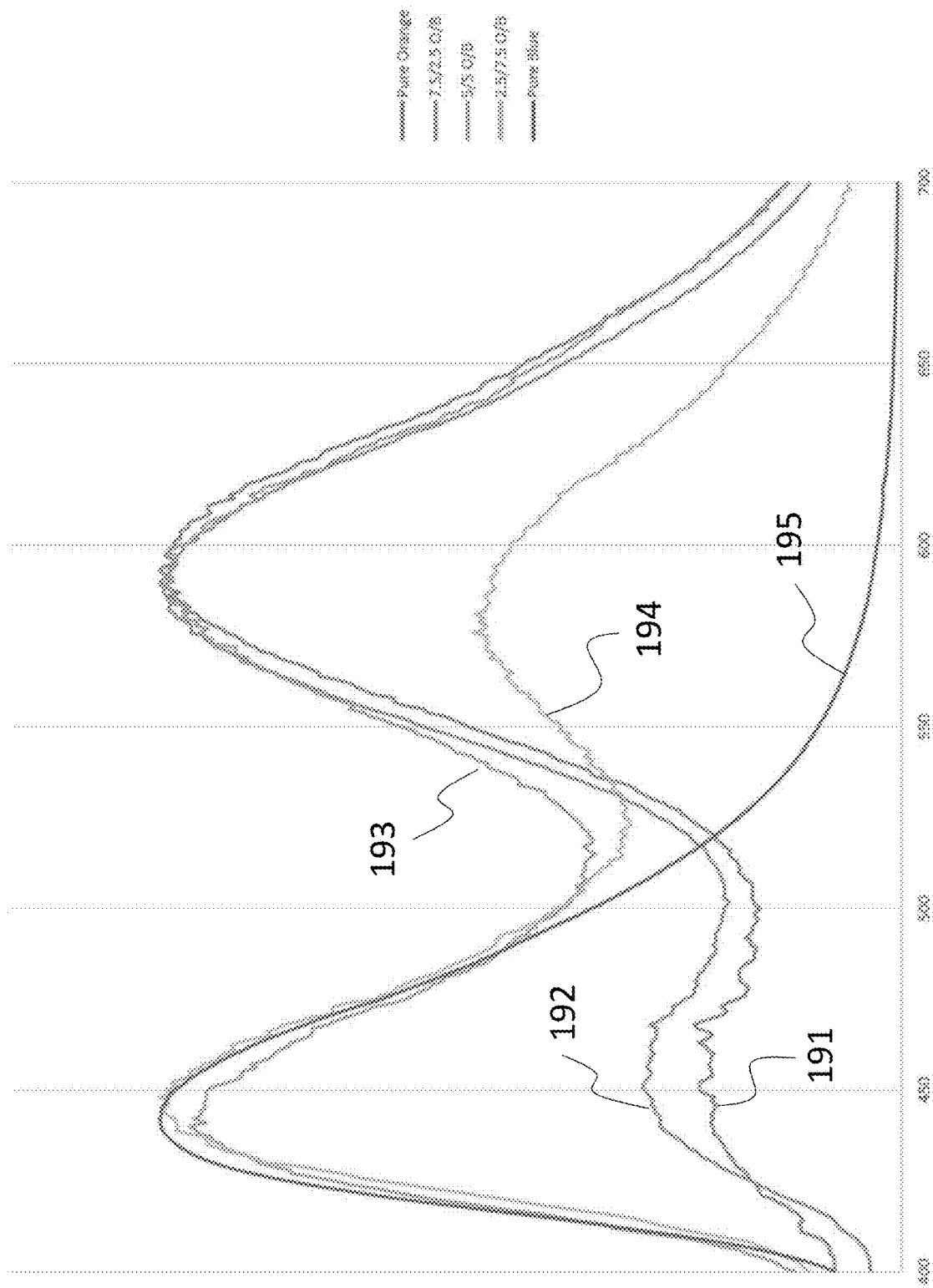
FIG. 19: is an example according to various embodiments, illustrating solid-state fluorescence spectra of synthesized blue MOFs, orange MOFs, and combinations thereof.

Discussion of FIG. 19

FIG. 19 is an example according to various embodiments, illustrating solid-state fluorescence spectra of synthesized blue MOFs, orange MOFs, and combinations thereof. Synthesis of such MOFs is described in the following Examples, including Examples 6-9. Spectra 191 is a solid state fluorescence spectrum of an orange MOF (structurally illustrated in FIG. 2D). Spectra 192 is a solid state fluorescence spectrum of a combination of 7.5 mol % orange MOF (structurally illustrated in FIG. 2D); 2.5 mol % blue MOF (structurally illustrated in FIG. 2C); and 90 mol % NF MOF (structurally illustrated in FIG. 2B). Spectra 193 is a solid state fluorescence spectrum of a combination of 5 mol % orange MOF (structurally illustrated in FIG. 2D); 5 mol % blue MOF (structurally illustrated in FIG. 2C); and 90 mol % NF MOF (structurally illustrated in FIG. 2B). Spectra 194 is a solid state fluorescence spectrum of a combination of 2.5 mol % orange MOF (structurally illustrated in FIG. 2D) and 7.5 mol % blue MOF (structurally illustrated in FIG. 2C) and 90 mol % NF MOF (structurally illustrated in FIG. 2B). Spectra 195 is a solid state fluorescence spectrum of a blue MOF (structurally illustrated in FIG. 2C).

Discussion of FIG. 20-60

FIGS. 20-60 are described above and are referenced in the following Examples.

EXAMPLES

Introduction

The following examples are put forth to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for.

The purpose of the following examples is not to limit the scope of the various embodiments, but merely to provide examples illustrating specific embodiments.

Materials and Methods

All starting materials and solvents, unless otherwise specified, were obtained from commercial sources (Aldrich, Fisher) and used without further purification. All reactions were performed at ambient laboratory conditions, and no precautions were taken to exclude oxygen or atmospheric moisture unless otherwise specified. Anhydrous N,N-dimethylformamide (DMF), Dichloromethane ($CH_2Cl_2$), and Tetrahydrofuran (THF) were purified using a custom-built alumina-column based solvent purification system (purchased from Inovative Technology). Anhydrous MeOH and dioxane were obtained from Aldrich (Sureseal grade). Deuterated solvents ($CDCl_3$, DMSO, NaOD 40% in $D_2O$) were obtained from Cambridge Isotope Lab. $K_2CO_3$ was dried in a 120° C. oven for 24 hours prior to use. Acetic Acid was dried over molecular sieves and degassed for 30 minutes using argon before being placed in an argon filled glovebox. 1,4-Benzoquinone was freshly sublimed prior to use.

High-resolution $^1H$, and $^{13}C$ nuclear magnetic resonance (NMR) spectra were recorded using Bruker AVANCE-III 400 MHz spectrometer. The $^1H$ chemical shifts are given relative to tetramethylsilane (TMS) as zero ppm, were calibrated using the residual solvent signal. Data processing was performed using MNova version 9.0.1.

Powder X-ray diffraction measurements were performed using a Rigaku Miniflex 600 diffractometer, with θ-2θ Bragg-Brentano geometry, and a 600 W (40 kV, 15 mA) Cu X-ray tube source using Kα (λ=1.5418 Å) radiation. Samples were measures from 3 to 80 2θ-degrees with a step size of 0.02° and a scan rate of 1.5 s per step. Samples were prepared by dropping the powder sample in a Si-zero background plate and pressing the powder with a razor blade spatula till smooth. Measurements on MTV MOF samples were performed at the spinning rate of a blank Si-zero background plate. Rietveld refinement was processed with GSAS II software. Simulated crystals and diffraction patterns were calculated using the Reflex module in Materials Studio (v8.0, Biovia) starting with the CIF file of UiO-66 (CCDC code) [5].

$N_2$ gas adsorption isotherm analysis was performed using a Micromertics ASAP 2020 porosimetry analyzer. The measurements was performed at 77 K. Mass spectra were recorded on an Agilent 6230 TOF LC-MS instrument with an Agilent Zorbax SB-C18 analytical column. Fourier-transform infrared spectra were recorded using a Perkin Elmer Spectrum ONE Universal FT-IR ATR under laboratory ambient conditions. A total of 32 transients were collected for each sample with a resolution of 0.05 $cm^{-1}$ between 4000-650 $cm^{-1}$.

Example 1

A purpose of this example is to illustrate a general synthetic scheme of the NF linker (also referenced in FIG. 2B).

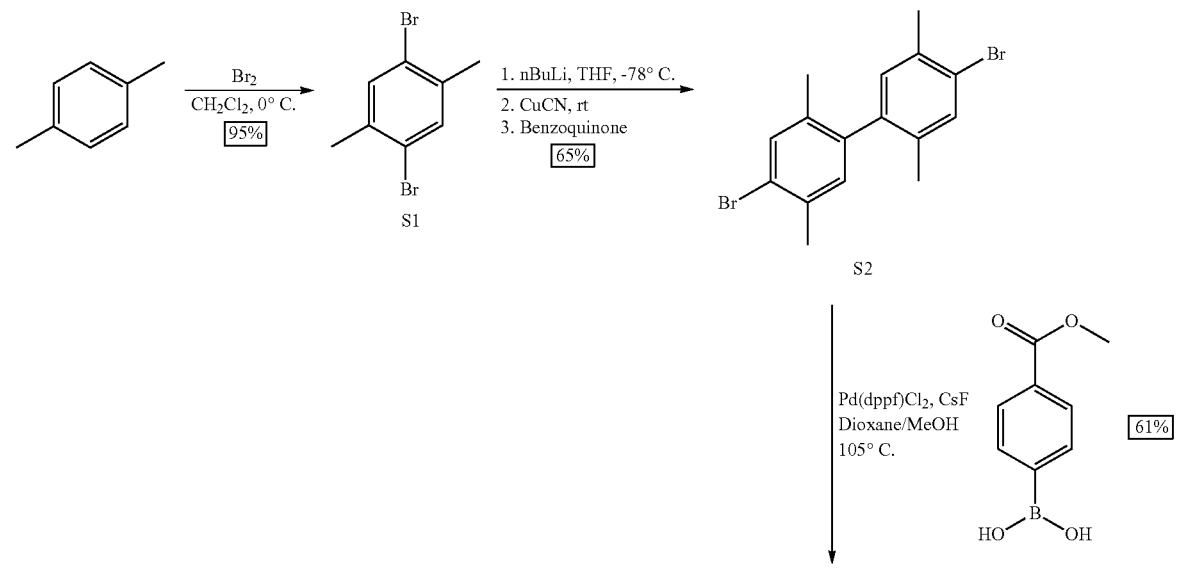

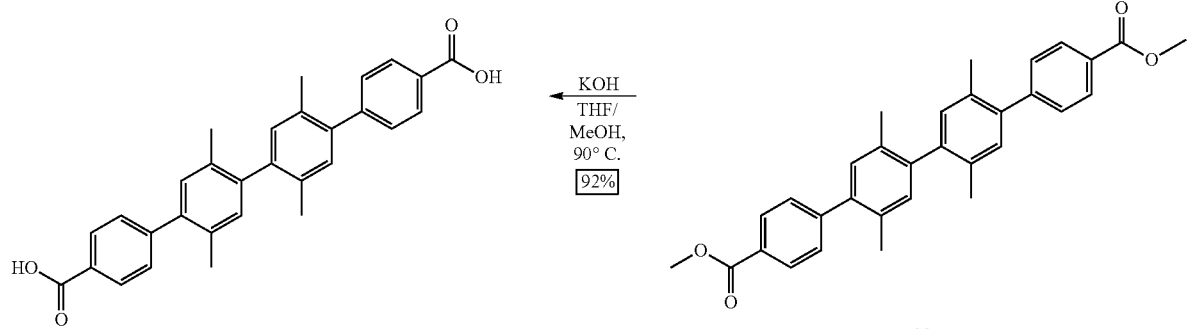

NF linker

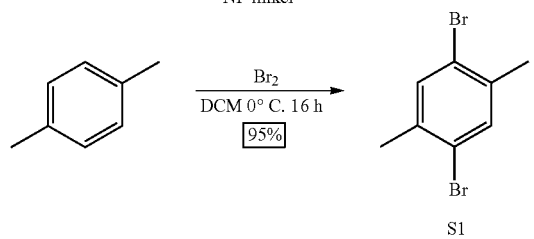

S3

2,5-dibromo-p-xylene (S1): Adapted from [1]. p-Xylene (27.8 mL, 226 mmol, 1 eq), 12 (2.87 g, 11.3 mmol, 0.05 eq) and $CH_2Cl_2$ (80 mL) were loaded into a 250 mL round bottom flask equipped with a magnetic stir bar and cooled to 0° C. $Br_2$ (23.5 mL, 456 mmol, 2.02 eq) and $CH_2Cl_2$ were loaded into an addition funnel and the solution was added dropwise to the xylene mixture over the course of 1 h keeping the temperature at 0° C. Upon completion of the addition, the mixture was allowed to warm to room temperature and stirred for 15 h, monitored by TLC. Aqueous KOH (30% w/w, 100 mL) was added to the mixture and stirred for 20 min until disappearance of the color in the organic layer. The organic fraction was separated from the mixture and rinsed with water (×1) and brine (×1), dried with $Na_2SO_4$ and filtered. The solvent was removed under reduced pressure in a rotary evaporator resulting in a pale white solid. Yield 56.4 g (95%).

Figure 20:
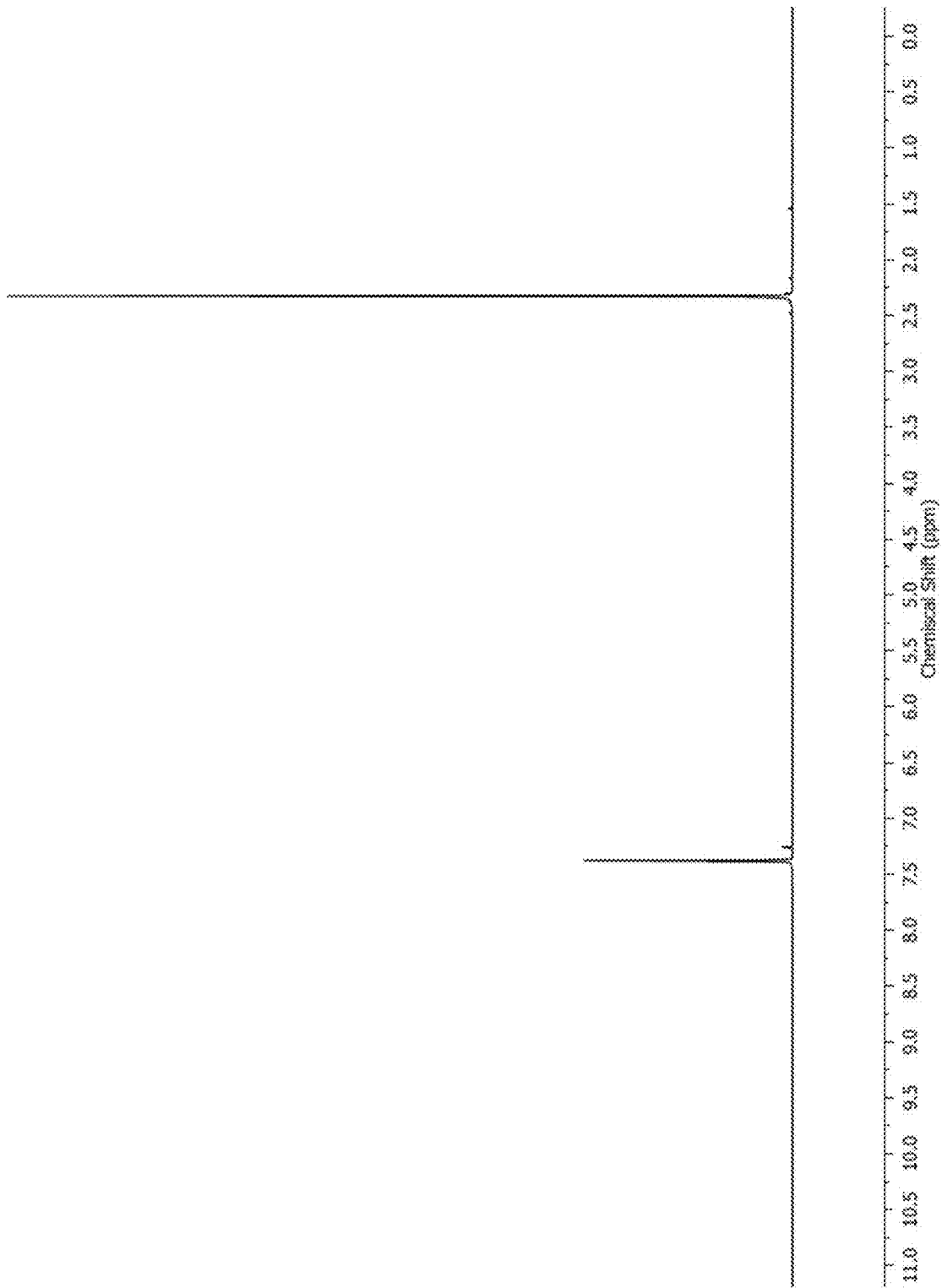
FIG. 20: is an example according to various embodiments, illustrating a characteristic $^1$HNMR (400 MHz, $CDCl_3$, 20° C.) spectra of compound S1 synthesized in the disclosed examples.

FIG. 20 shows $^1$HNMR (400 MHz, $CDCl_3$, 25° C.) δ (ppm) 7.39 (s, 2H), 2.33 (s, 6H) spectra of compound S1.

Figure 21:
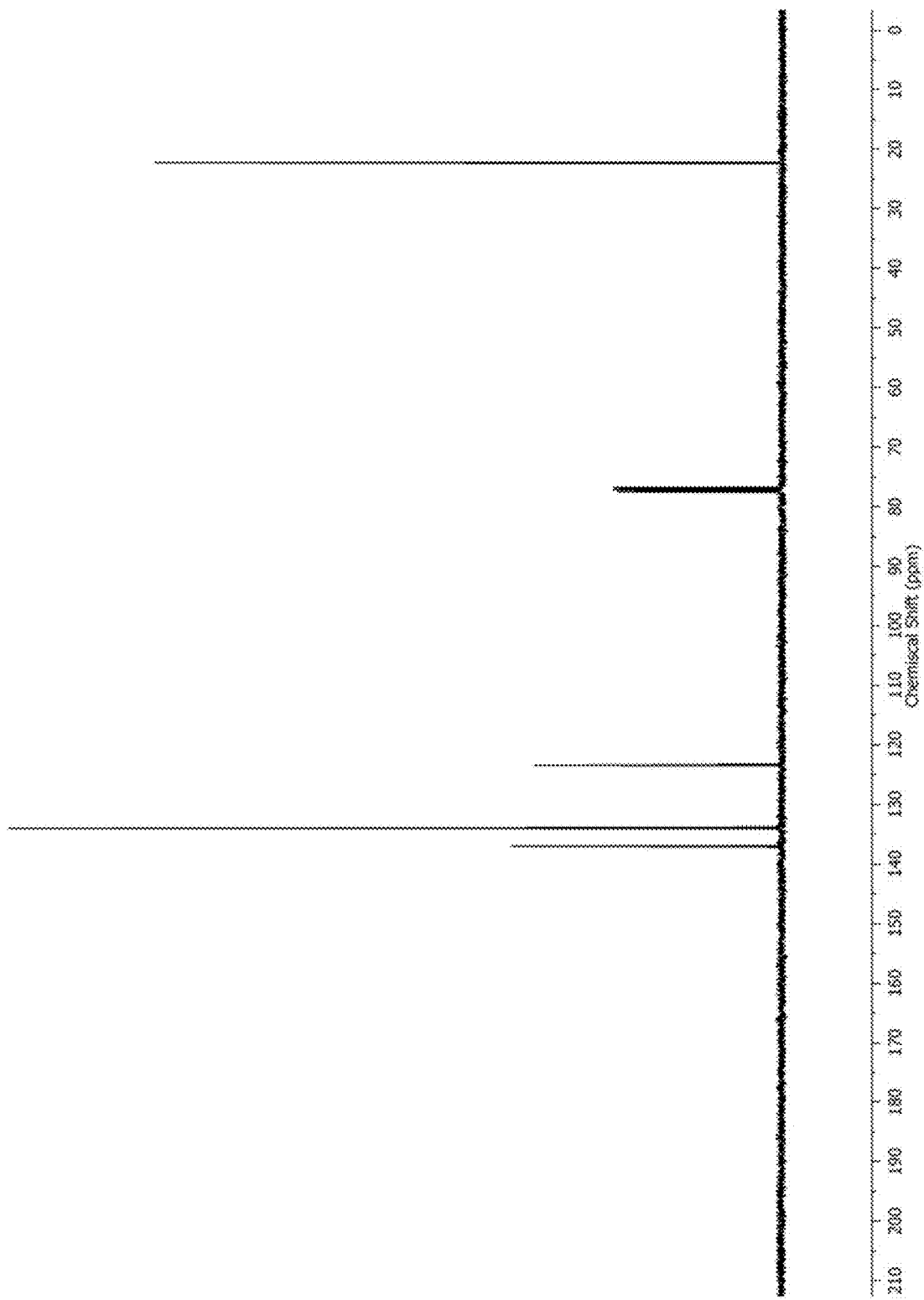
FIG. 21: is an example according to various embodiments, illustrating a characteristic $^{13}$CNMR (101 MHz, $CDCl_3$, 20° C.) spectra of compound S1 synthesized in the disclosed examples.

FIG. 21 shows $^{13}$C NMR (101 MHz, $CDCl_3$, 25° C.) δ (ppm) 136.95, 133.92, 123.40, 22.21 spectra of compound S1.

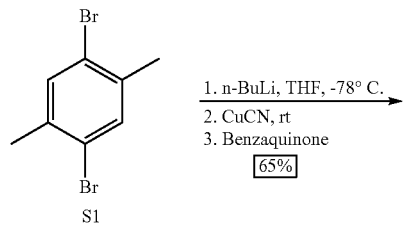

4,4'-dibromo-2,2',5,5'-tetramethyl-1,1'-Biphenyl (S2): S1 (2.00 g, 7.577 mmol, 1.0 eq) was added to a 250 mL Schlenk flask equipped with a magnetic stir bar and evacuated to 100 mtorr and back filled with $N_2$ gas, this procedure was repeated to a total of three times. Anhydrous THF (58 mL) was added to the Schlenk flask and cooled to −78° C. 2.5 M nBuLi (3.64 mL, 9.092 mmol, 1.2 eq) was added dropwise over the course of 5 min, and the solution was stirred at −78° C. for 1.5 h. CuCN (0.339 g, 3.788 mmol, 0.5 eq) was added under $N_2$ flow, and allowed to warm to room temperature until dissolution of the CuCN, approximately 1 h. Benzoquinone (1.229 g, 11.36 mmol, 1.5 eq) was added to the flask at room temperature forming a deep solution which was stirred at room temperature for 10 h. The reaction was quenched with aqueous 2 M HCl (100 mL) and diluted to a total volume of 200 mL with water. The aqueous phase was extracted with $CH_2Cl_2$ (×3), the combined organic extracts were rinsed with water (×1), brine (×1), dried over $Na_2SO_4$, and filtered. The solvent was removed under reduced pressure in a rotary evaporator. The crude product was then purified by column chromatography ($SiO_2$, hexanes) resulting in a clear oil. Yield 0.9115 g (65%).

Figure 22:
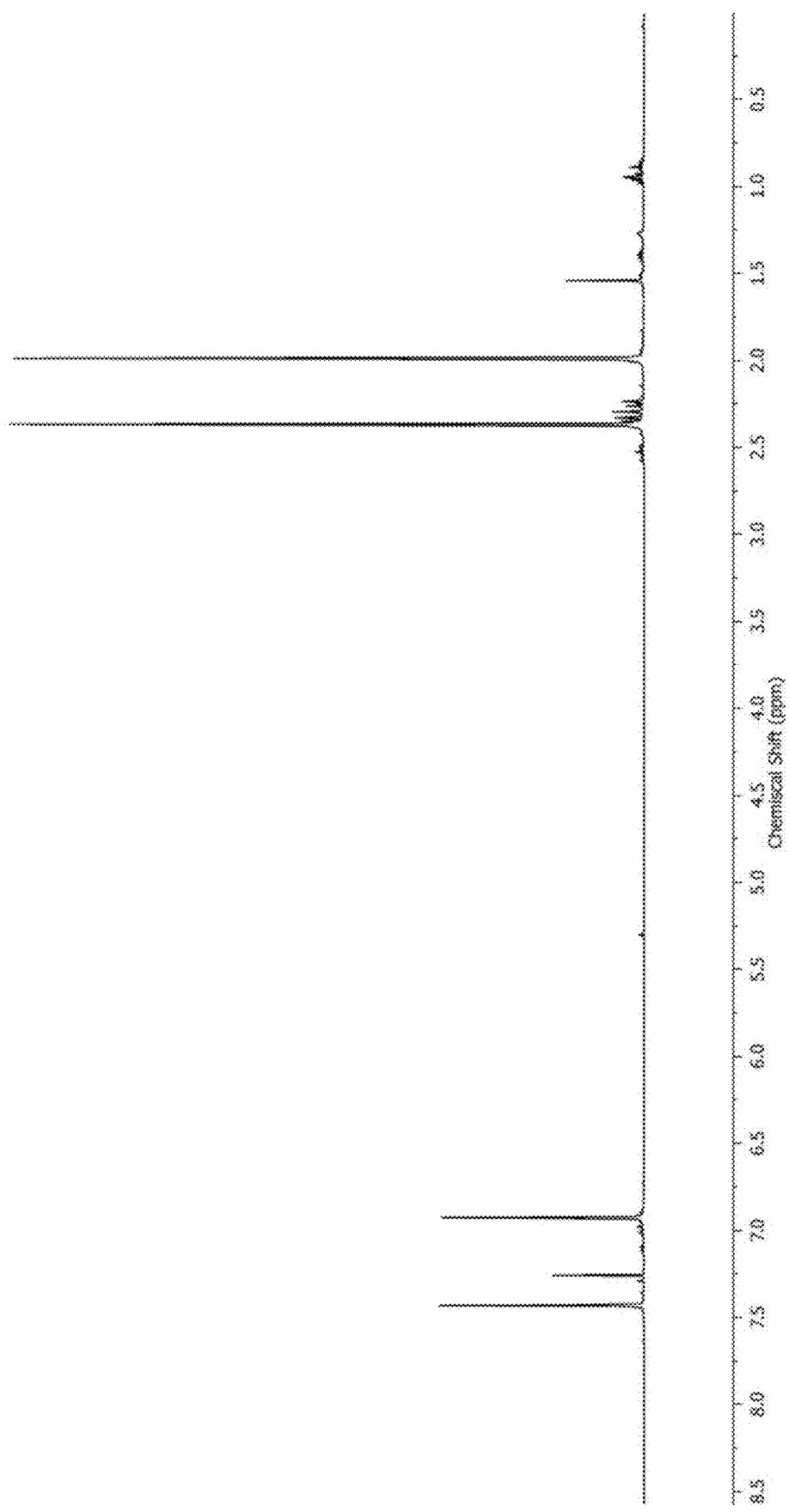
FIG. 22: is an example according to various embodiments, illustrating a characteristic $^1$HNMR (400 MHz, $CDCl_3$, 20° C.) spectra of compound S2 synthesized in the disclosed examples.

FIG. 22 shows $^1$HNMR (400 MHz, $CDCl_3$, 25° C.) δ (ppm) 7.43 (s, 2H), 6.93 (s, 2H), 2.37 (s, 6H), 1.99 (s, 6H) spectra of compound S2.

Figure 23:
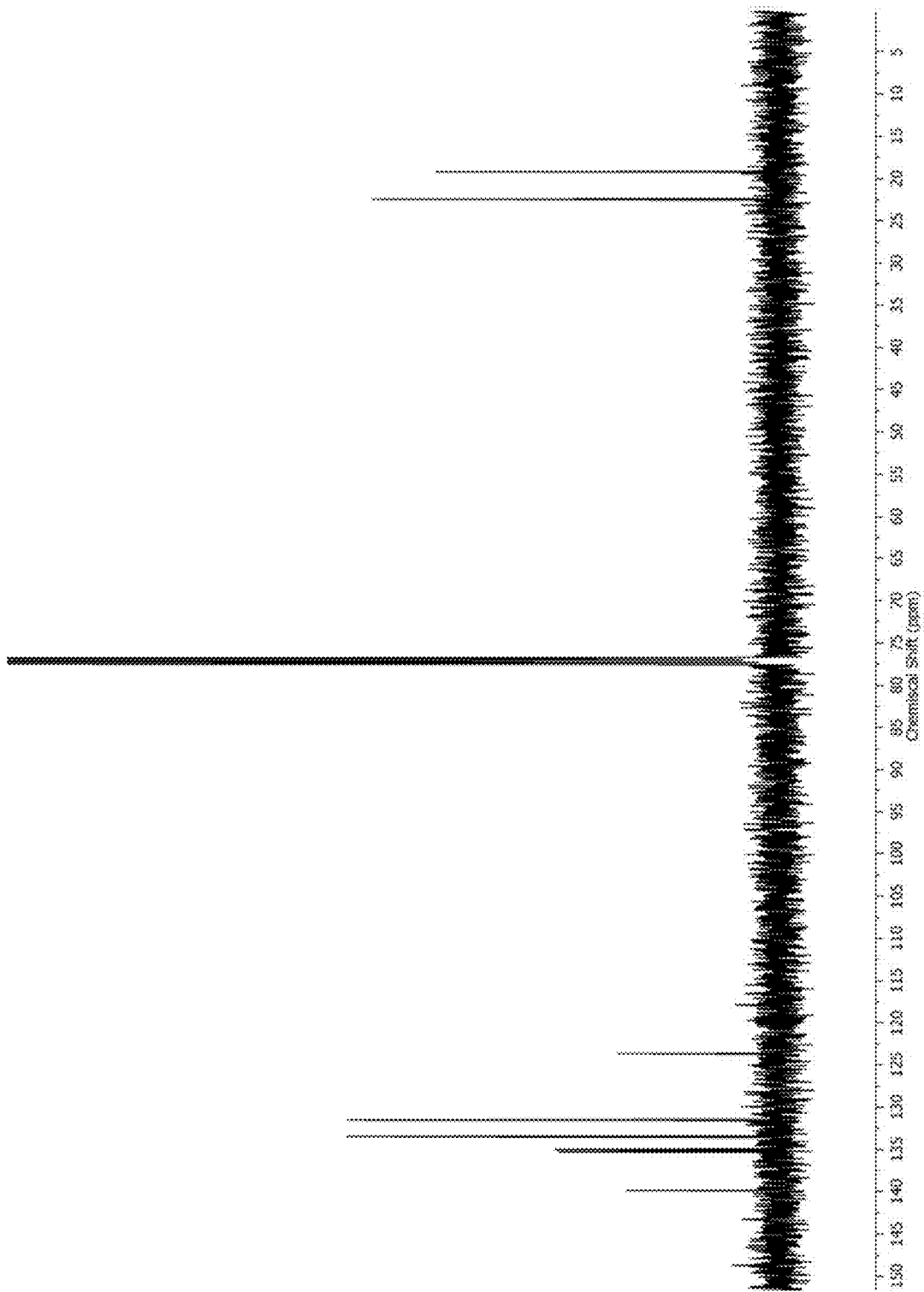
FIG. 23: is an example according to various embodiments, illustrating a characteristic $^{13}$CNMR (101 MHz, $CDCl_3$, 20° C.) spectra of compound S2 synthesized in the disclosed examples.

FIG. 23 shows $^{13}$C NMR (101 MHz, $CDCl_3$, 25° C.) δ (ppm) 139.85, 135.28, 135.04, 133.48, 131.53, 123.69, 22.45, 19.18 spectra of compound S2. This synthetic step is an adaptation of reference [7]).

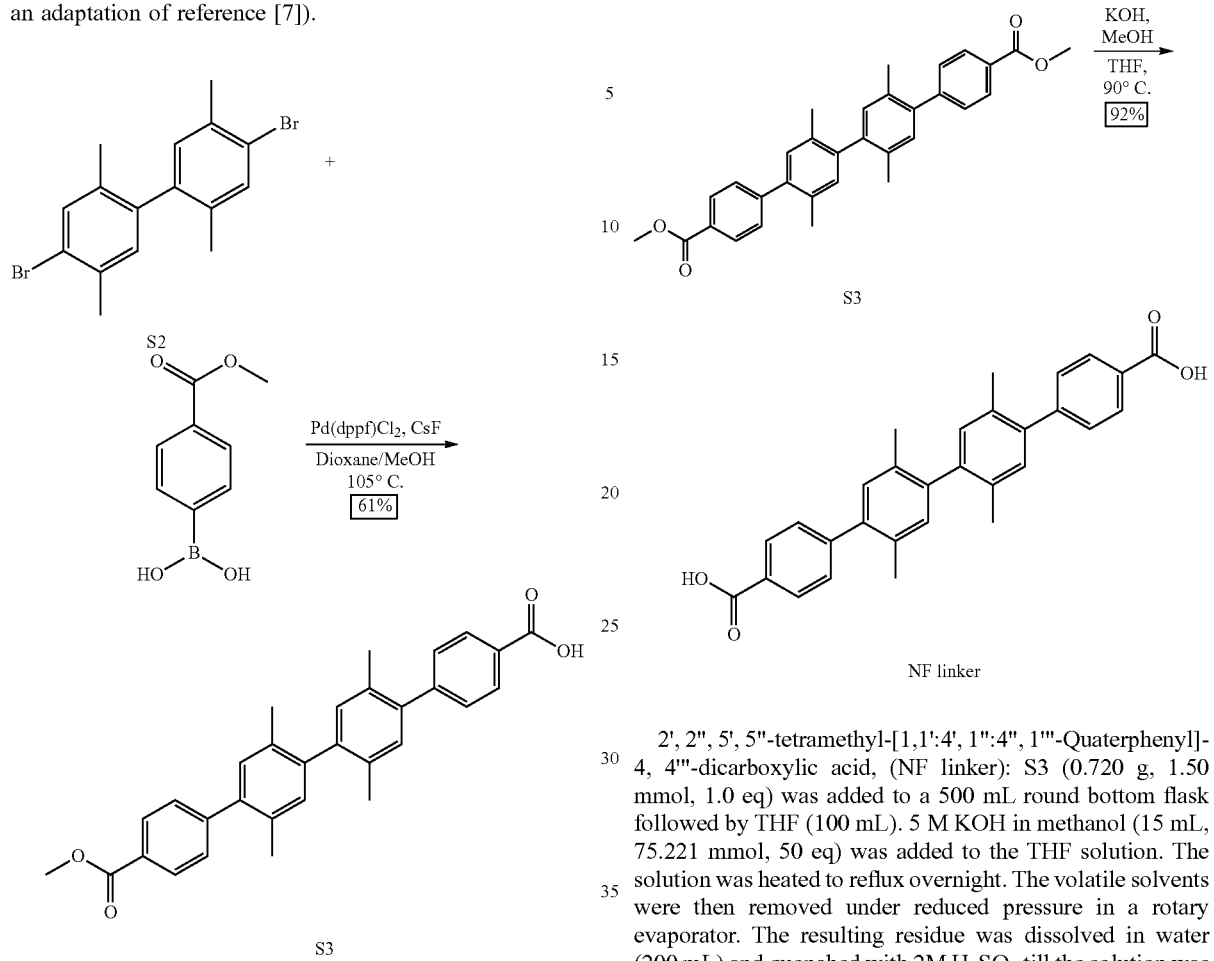

2', 2'',5',5''-tetramethyl-[1,1':4',1'':4'',1'''-Quaterphenyl]-4, 4'''-dicarboxylic acid, 4,4'''-dimethyl ester (S3): S2 (0.911 g, 2.475 mmol, 1.0 eq), 4-(methoxycarbonyl)-phenyl boronic acid (1.113 g, 6.187 mmol, 2.5 eq), CsF (1.128 g, 7.424 mmol, 3.0 eq), and Pd(dppf)Cl$_2$ (0.101 g, 0.124 mmol, 0.05 eq) were added to a 50 mL Schlenk flask containing S2. The Schlenk flask was the evacuated to 100 mtorr and backfilled with N$_2$, this procedure was repeated for a total of three times. Anhydrous dioxane (19 mL) and anhydrous methanol (6.2 mL) were added to the Schlenk flask under N$_2$. The solution was stirred and heated to 105° C. for 20 h. The solution was cooled to room temperature and quenched with water (50 mL), and was extracted with CH$_2$Cl$_2$ (×3). The combined organic layers were rinsed once with water and once with brine, dried over Na$_2$SO$_4$, and filtered. The CH$_2$Cl$_2$ was removed under reduced pressure in a rotary evaporator. The crude was purified using column chromatography (SiO$_2$, 5-15% v/v EtOAc/Hexanes), resulting in a white solid. Yield 0.72 g (61%).

Figure 24:
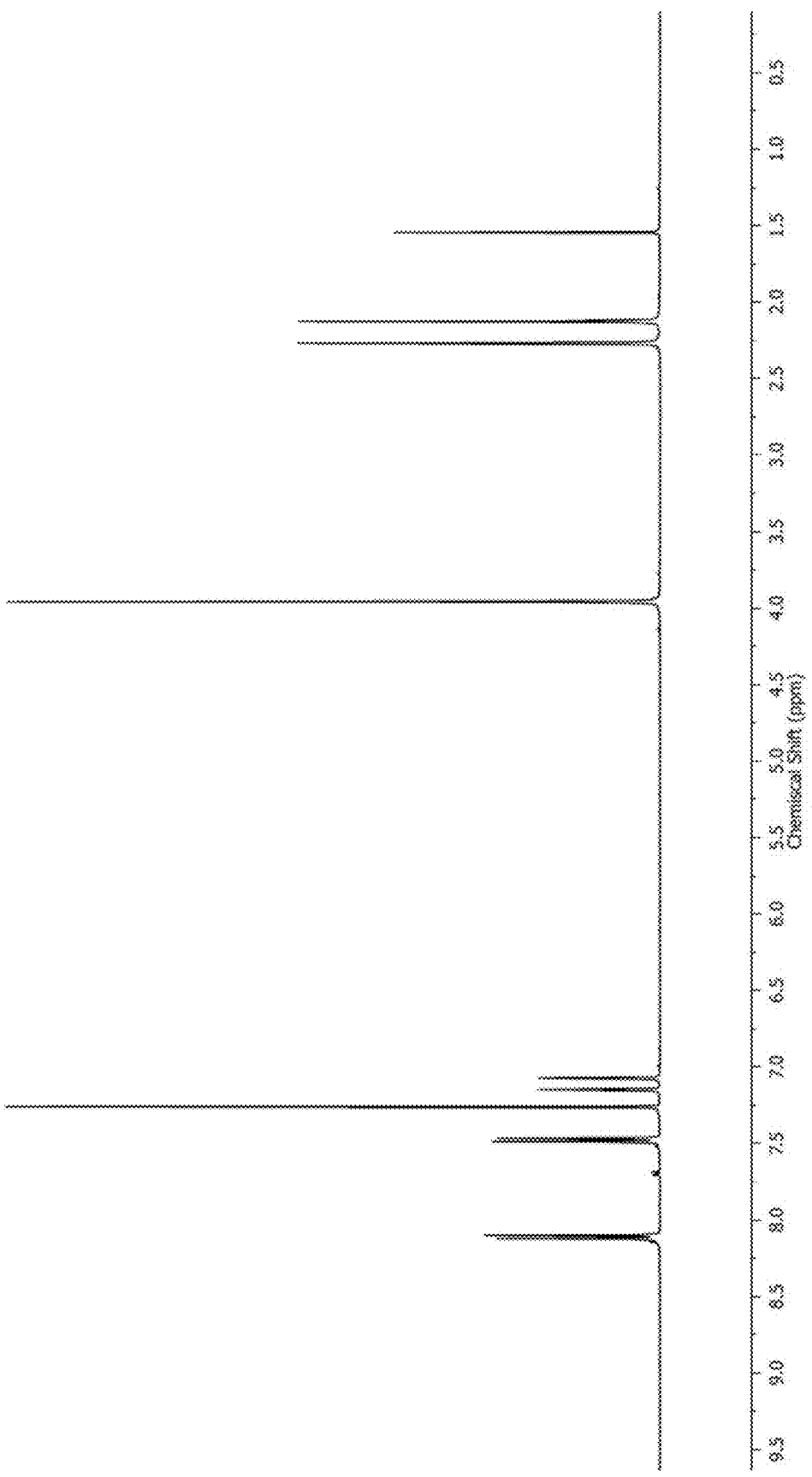
FIG. 24: is an example according to various embodiments, illustrating a characteristic $^1$HNMR (400 MHz, $CDCl_3$, 20° C.) spectra of compound S3 synthesized in the disclosed examples.

FIG. 24 shows $^1$HNMR (400 MHz, CDCl$_3$, 25° C.) δ (ppm) 8.11 (d, J=8.5 Hz, 4H), 7.48 (d, J=8.5 Hz, 4H), 7.15 (s, 2H), 7.07 (s, 2H), 3.96 (s, 6H), 2.27 (s, 6H), 2.13 (s, 6H) spectra of compound S3.

Figure 25:
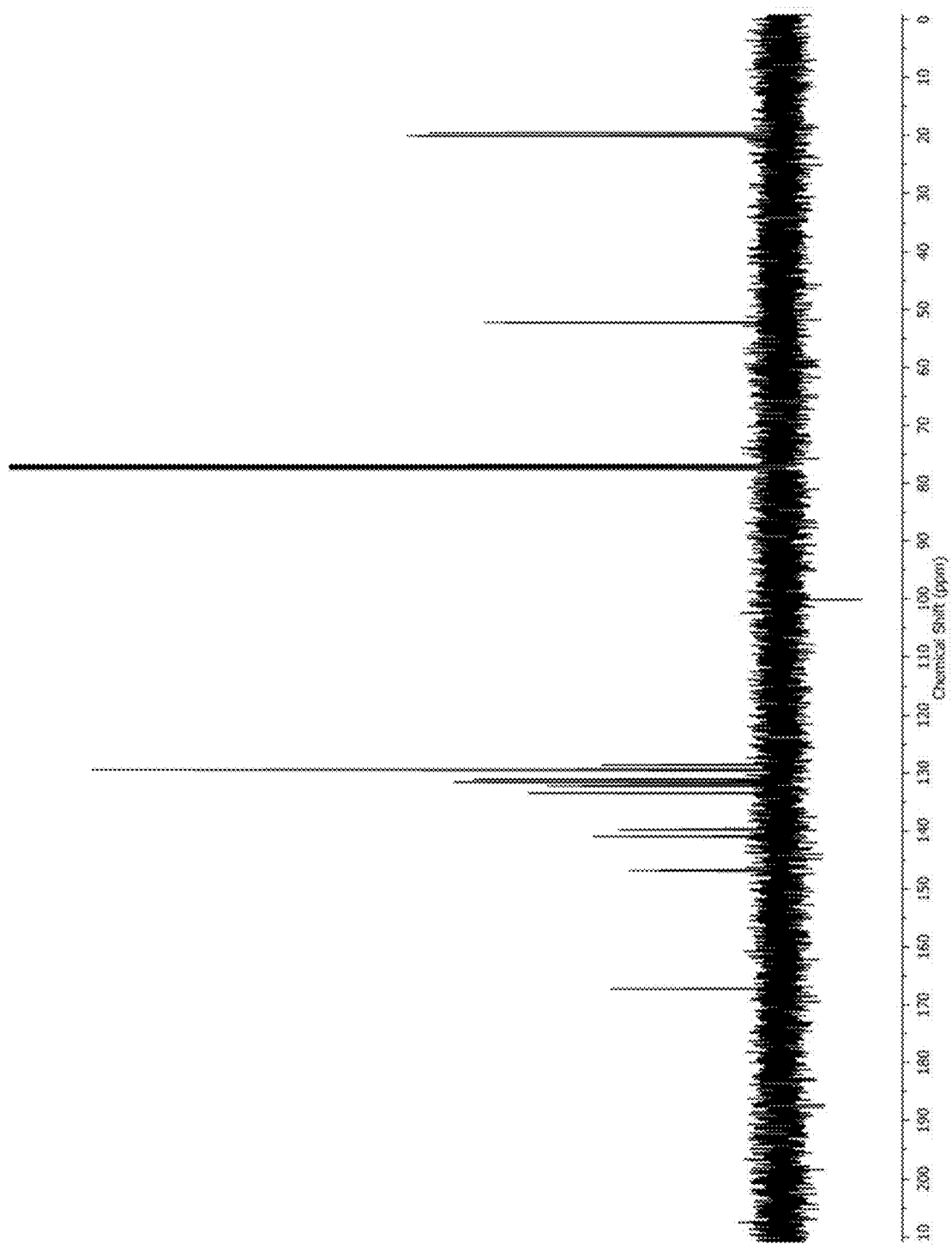
FIG. 25: is an example according to various embodiments, illustrating a characteristic $^{13}$CNMR (101 MHz, $CDCl_3$, 20° C.) spectra of compound S3 synthesized in the disclosed examples.

FIG. 25 $^{13}$C NMR (101 MHz, CDCl$_3$, 25° C.) δ (ppm) 170.36, 167.26, 146.86, 140.95, 139.80, 133.50, 132.29, 131.66, 131.14, 129.55, 129.49, 128.65, 100.09, 52.28, 20.05, 19.53 spectra of compound S3.

2', 2'', 5', 5''-tetramethyl-[1,1':4', 1'':4'', 1'''-Quaterphenyl]-4, 4'''-dicarboxylic acid, (NF linker): S3 (0.720 g, 1.50 mmol, 1.0 eq) was added to a 500 mL round bottom flask followed by THF (100 mL). 5 M KOH in methanol (15 mL, 75.221 mmol, 50 eq) was added to the THF solution. The solution was heated to reflux overnight. The volatile solvents were then removed under reduced pressure in a rotary evaporator. The resulting residue was dissolved in water (200 mL) and quenched with 2M H$_2$SO$_4$ till the solution was acidic and a light grey solid had precipitated out of the solution. The precipitate was collected by vacuum filtration and rinsed with water and cold methanol. Yield 0.62 g (92%).

Figure 26:
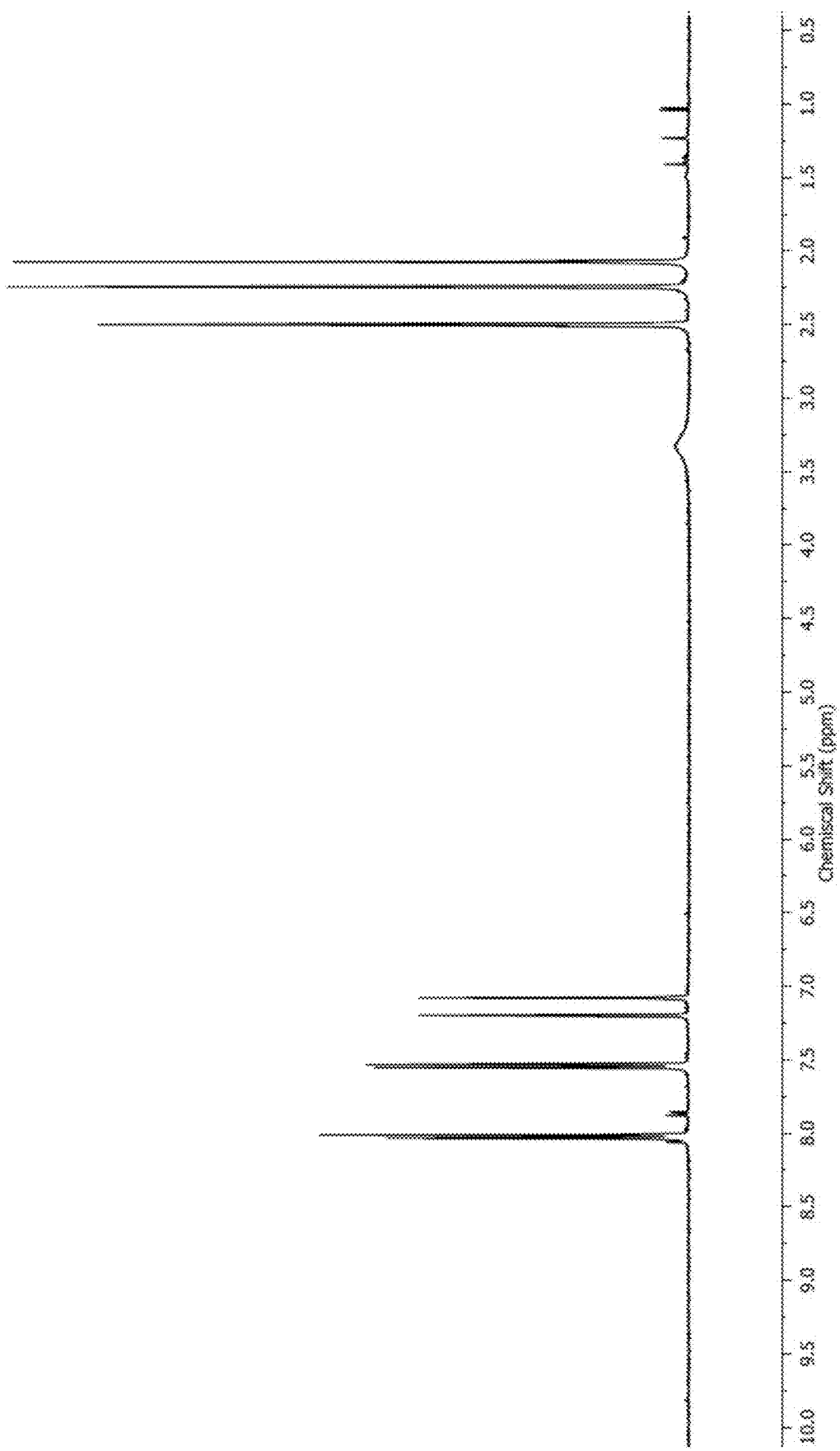
FIG. 26: is an example according to various embodiments, illustrating a characteristic $^1$HNMR (400 MHz, DMSO-$d_6$, 20° C.) spectra of an NF linker compound synthesized in the disclosed examples.

FIG. 26 shows $^1$HNMR (400 MHz, DMSO-d$_6$) δ (ppm) 8.02 (d, J=6.6 Hz, 4H), 7.54 (d, J=8.0 Hz, 4H), 7.20 (s, 2H), 7.07 (s, 2H), 2.24 (s, 6H), 2.07 (s, 6H) spectra of the NF linker.

Figure 27:
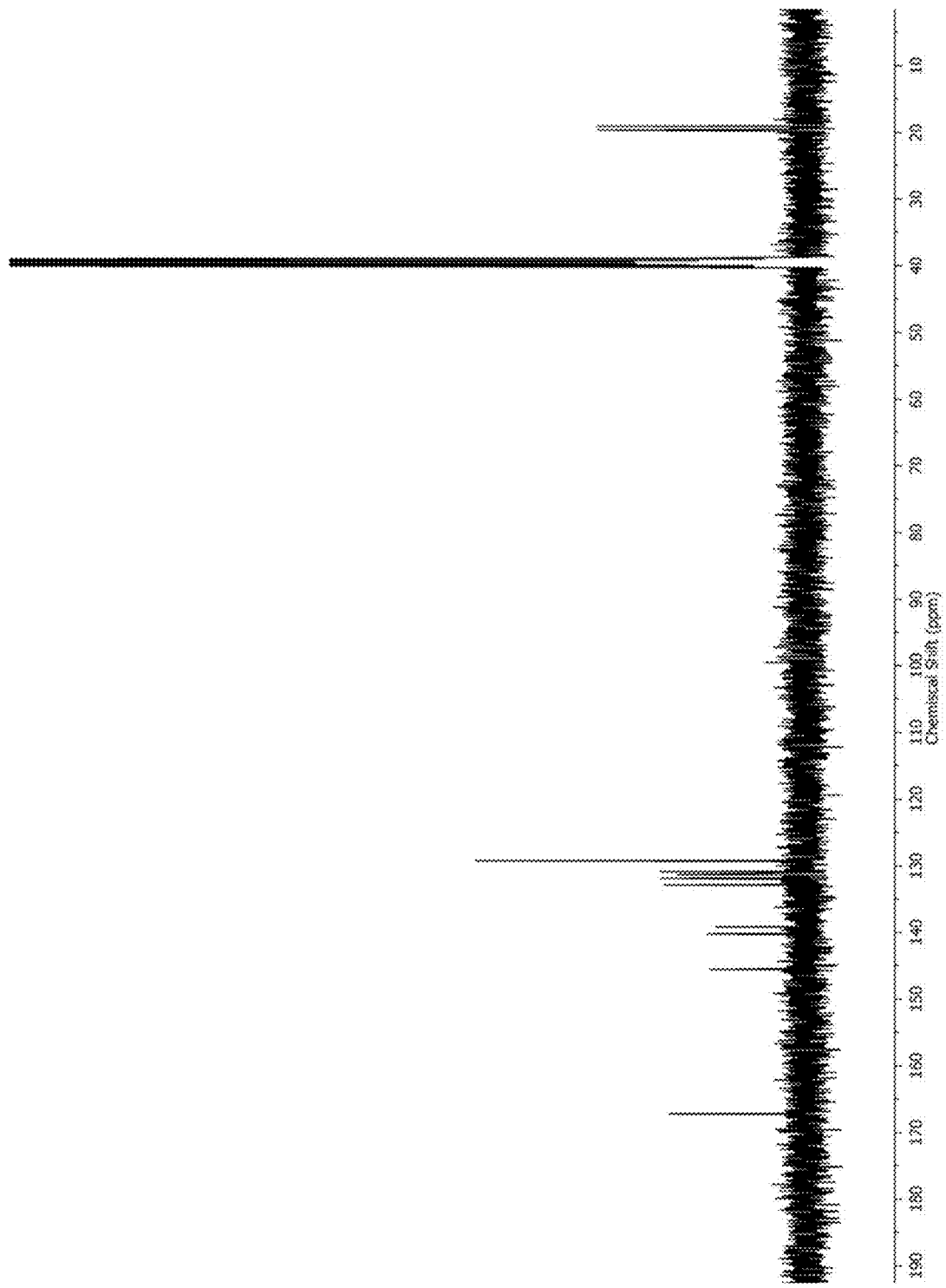
FIG. 27: is an example according to various embodiments, illustrating a characteristic $^{13}$CNMR (101 MHz, DMSO-$d_6$, 20° C.) spectra of an NF linker compound synthesized in the disclosed examples.

FIG. 27 shows $^{13}$C NMR (101 MHz, DMSO-d$_6$, 25° C.) δ (ppm) HRMS 167.18, 145.57, 140.25, 139.19, 132.84, 131.84, 131.29, 130.84, 129.28, 129.23, 129.23, 19.62, 19.06 spectra of the NF linker.

Example 2

A purpose of this example is to illustrate a general synthetic Scheme of Blue linker (also referenced in FIG. 2C).

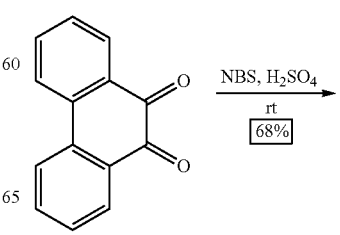

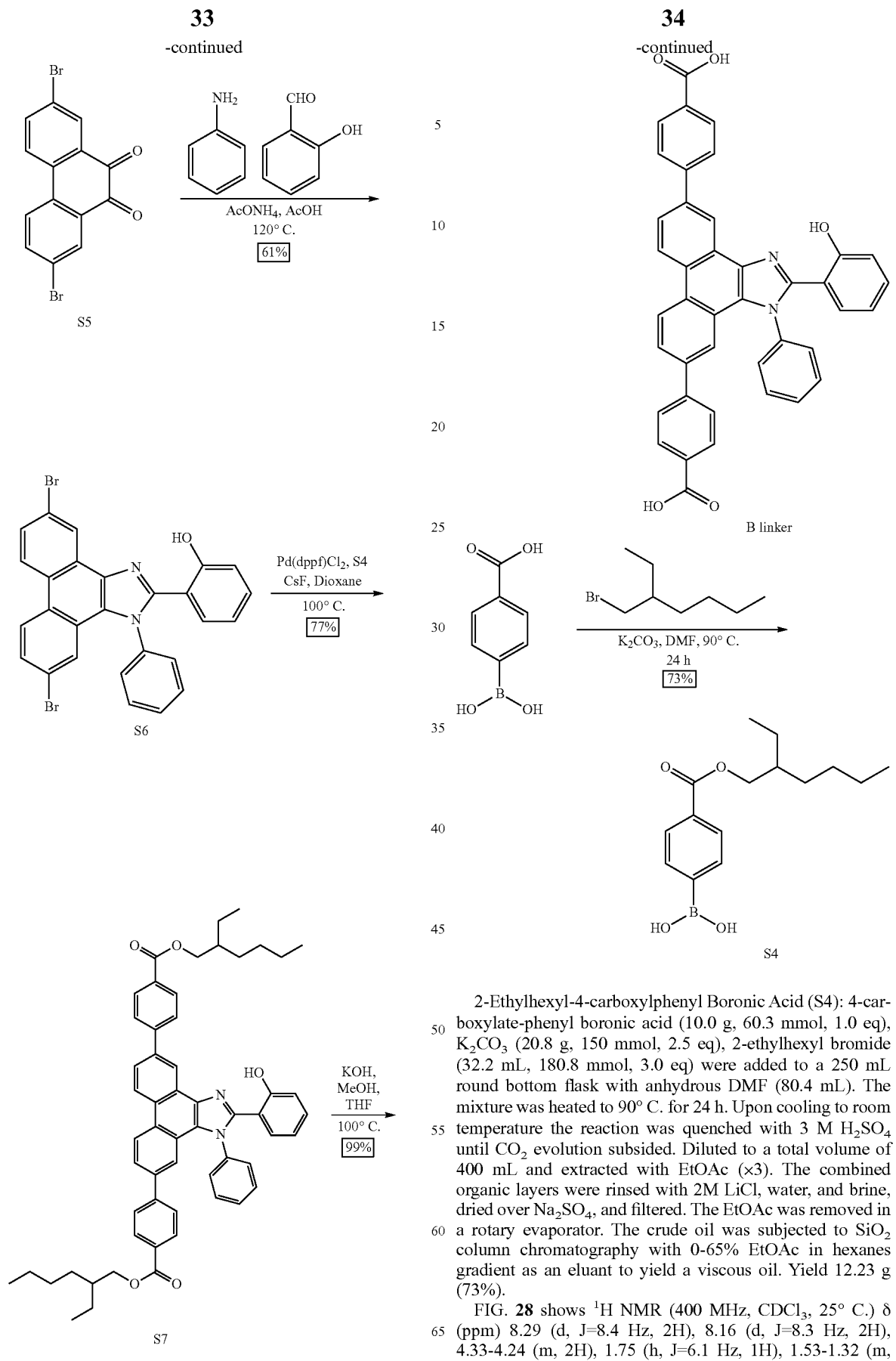

2-Ethylhexyl-4-carboxylphenyl Boronic Acid (S4): 4-carboxylate-phenyl boronic acid (10.0 g, 60.3 mmol, 1.0 eq), $K_2CO_3$ (20.8 g, 150 mmol, 2.5 eq), 2-ethylhexyl bromide (32.2 mL, 180.8 mmol, 3.0 eq) were added to a 250 mL round bottom flask with anhydrous DMF (80.4 mL). The mixture was heated to 90° C. for 24 h. Upon cooling to room temperature the reaction was quenched with 3 M $H_2SO_4$ until $CO_2$ evolution subsided. Diluted to a total volume of 400 mL and extracted with EtOAc (×3). The combined organic layers were rinsed with 2M LiCl, water, and brine, dried over $Na_2SO_4$, and filtered. The EtOAc was removed in a rotary evaporator. The crude oil was subjected to $SiO_2$ column chromatography with 0-65% EtOAc in hexanes gradient as an eluant to yield a viscous oil. Yield 12.23 g (73%).

Figure 28:
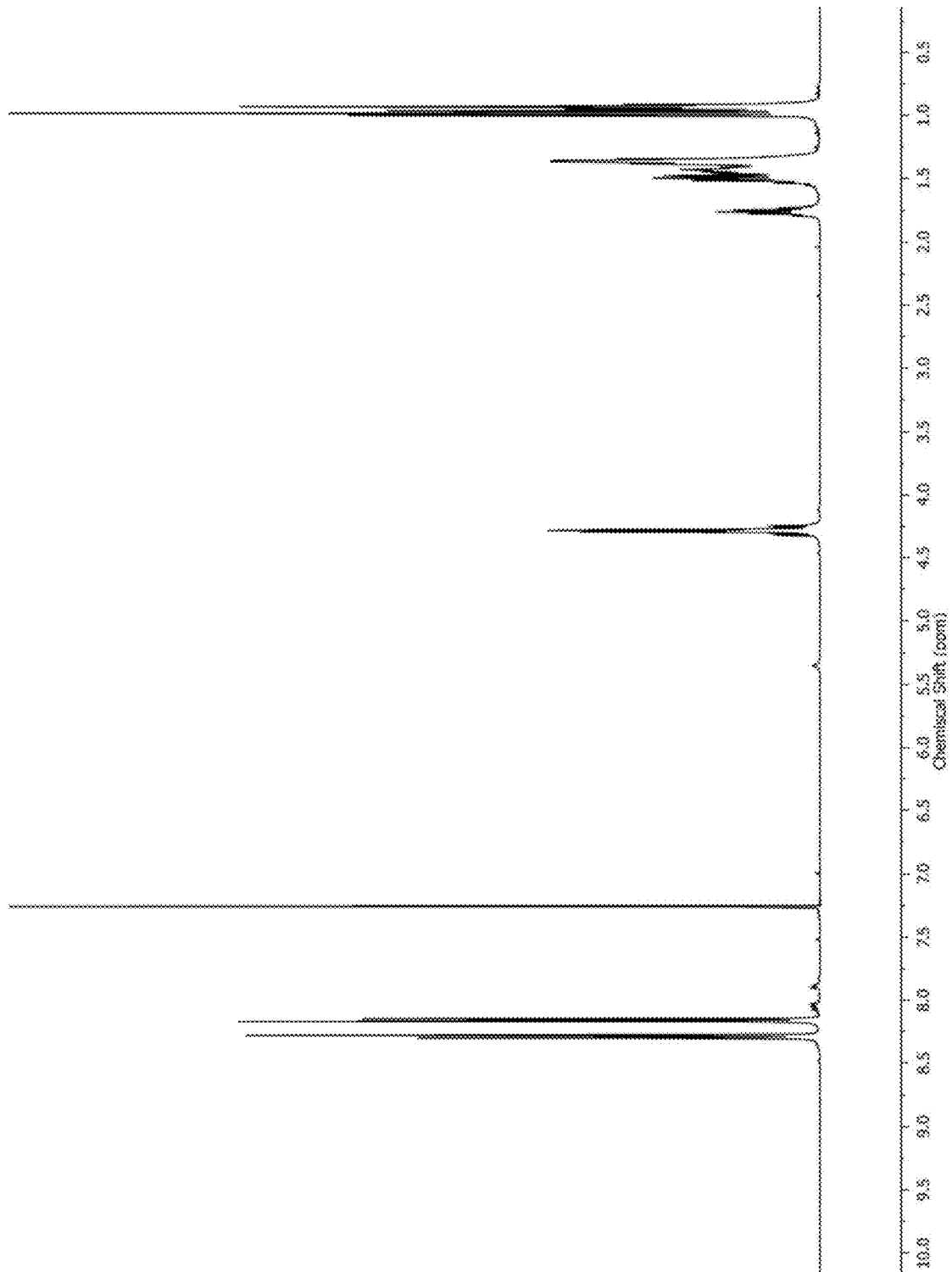
FIG. 28: is an example according to various embodiments, illustrating a characteristic $^1$HNMR (400 MHz, $CDCl_3$, 20° C.) spectra of compound S4 synthesized in the disclosed examples.

FIG. 28 shows $^1$H NMR (400 MHz, $CDCl_3$, 25° C.) δ (ppm) 8.29 (d, J=8.4 Hz, 2H), 8.16 (d, J=8.3 Hz, 2H), 4.33-4.24 (m, 2H), 1.75 (h, J=6.1 Hz, 1H), 1.53-1.32 (m, 8H), 1.00-0.89 (m, 6H) spectra of compound S4.

Figure 29:
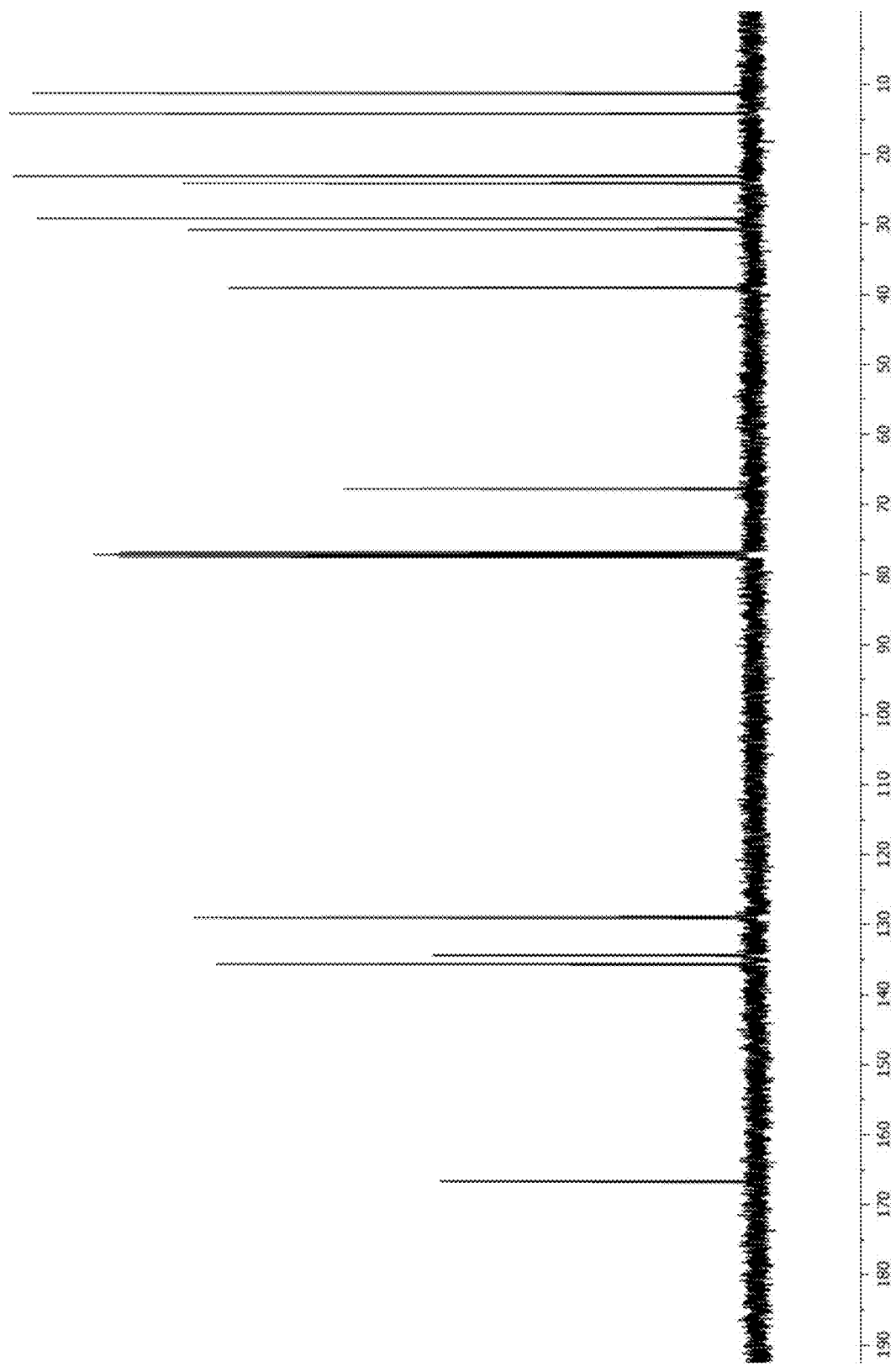
FIG. 29: is an example according to various embodiments, illustrating a characteristic $^{13}$CNMR (101 MHz, $CDCl_3$, 20° C.) spectra of compound S4 synthesized in the disclosed examples.

FIG. 29 shows $^{13}$C NMR (101 MHz, CDCl$_3$) δ (ppm) 166.67, 135.70, 134.43, 129.02, 67.80, 39.07, 30.76, 29.14, 24.17, 23.14, 14.20, 11.27 spectra of compound S4.

Figure 30:
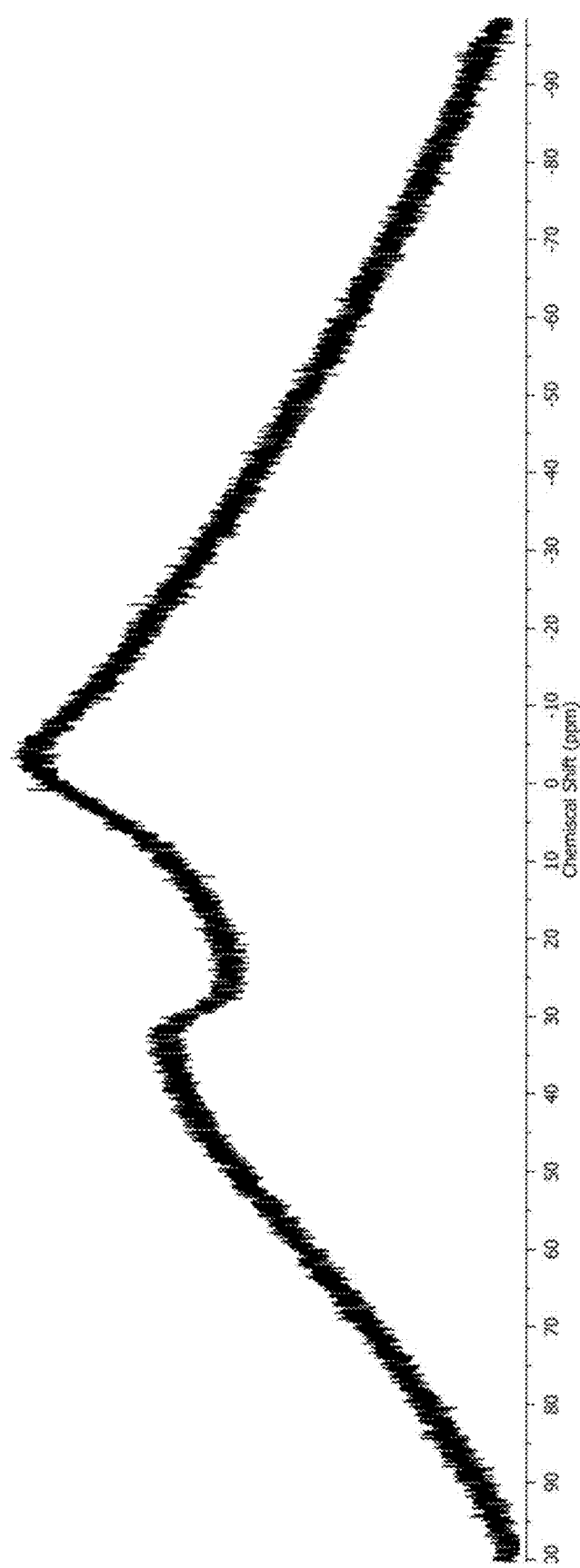
FIG. 30: is an example according to various embodiments, illustrating a characteristic $^{11}$BNMR (128 MHz, $CDCl_3$, 20° C.) spectra of compound S4 synthesized in the disclosed examples.

FIG. 30 shows 11 BNMR (128 MHz, CDCl3, 20° C.) spectra of compound S4.

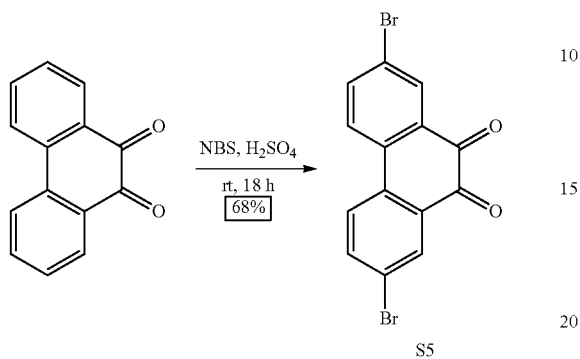

S5

2,7-dibromo-9,10-phenanthraquinone (S5): 9,10-phenanthraquinone (5.00 g, 24.01 mmol, 1.0 eq), N-bromosuccinimide, NBS, (9.40 g, 52.83 mmol, 2.2 eq) was added to a 500 mL round bottom flask equipped with a magnetic stir bar followed by sulfuric acid (138.8 mL). The solution was stirred at room temperature for one hour, at which point the viscosity of the solution was high enough that the magnetic stir bar would not mix the solution. Thus the flask was lowered into an ultrasonic bath which lowered the viscosity and allowed the solution to continue mixing. The mixture was then stirred 17 h at room temperature. The reaction was quenched by pouring onto ice. The product was collected by vacuum filtration and rinsed with water. The crude was recrystallized from boiling DMSO. The pure product was filtered off and rinsed with water and dried under a low pressure vacuum, resulting in deep orange crystals. Yield 5.93 g (68%).

Figure 31:
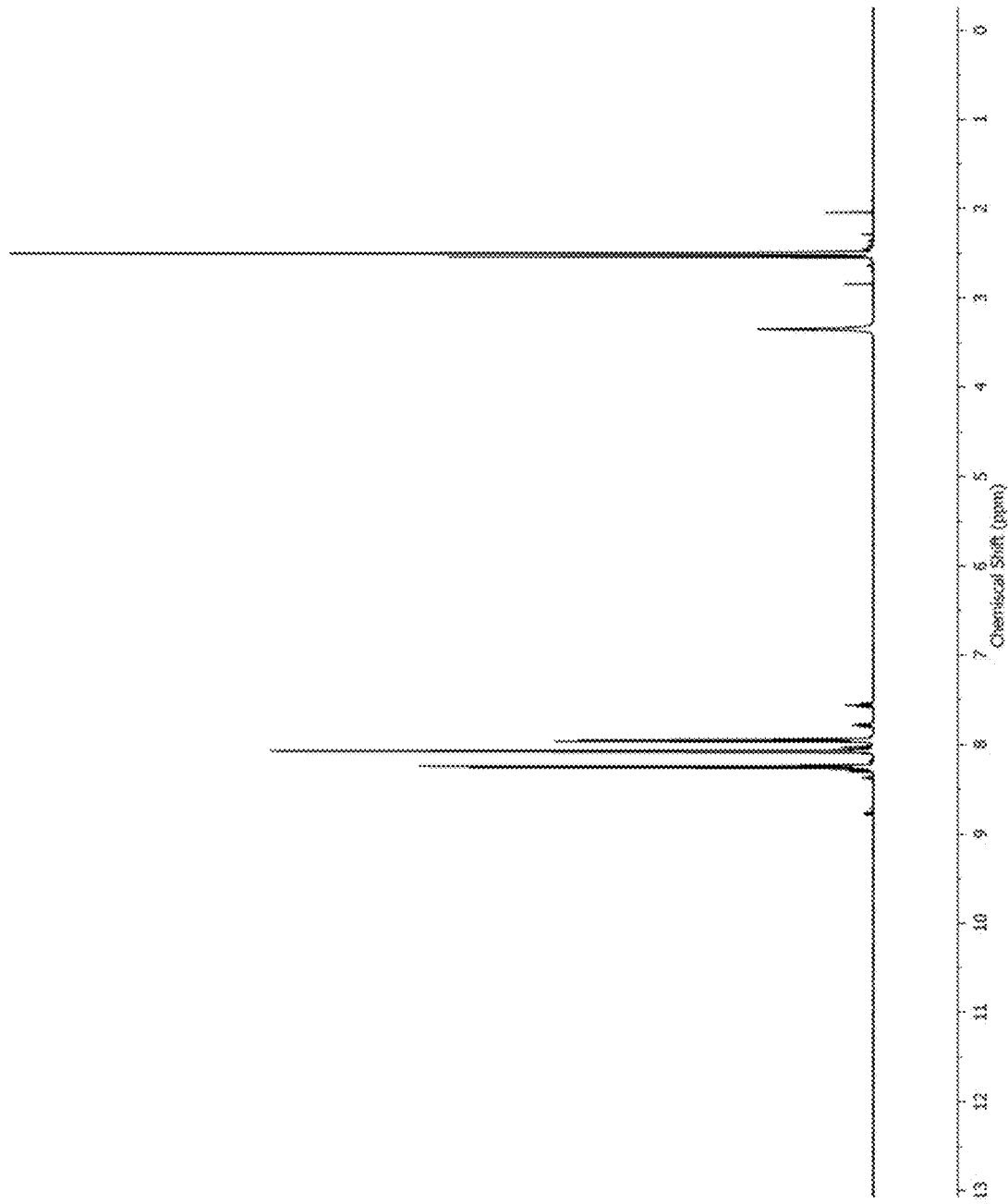
FIG. 31: is an example according to various embodiments, illustrating a characteristic $^1$HNMR (400 MHz, DMSO-$d_6$, 20° C.) spectra of compound S5 synthesized in the disclosed examples.

FIG. 31 shows $^1$HNMR (400 MHz, DMSO-d$_6$, 25° C.) δ (ppm) 8.25 (d, J=8.6 Hz, 1H), 8.08 (d, J=2.3 Hz, 1H), 7.96 (dd, J=8.5, 2.3 Hz, 1H) spectra of compound S5.

Figure 32:
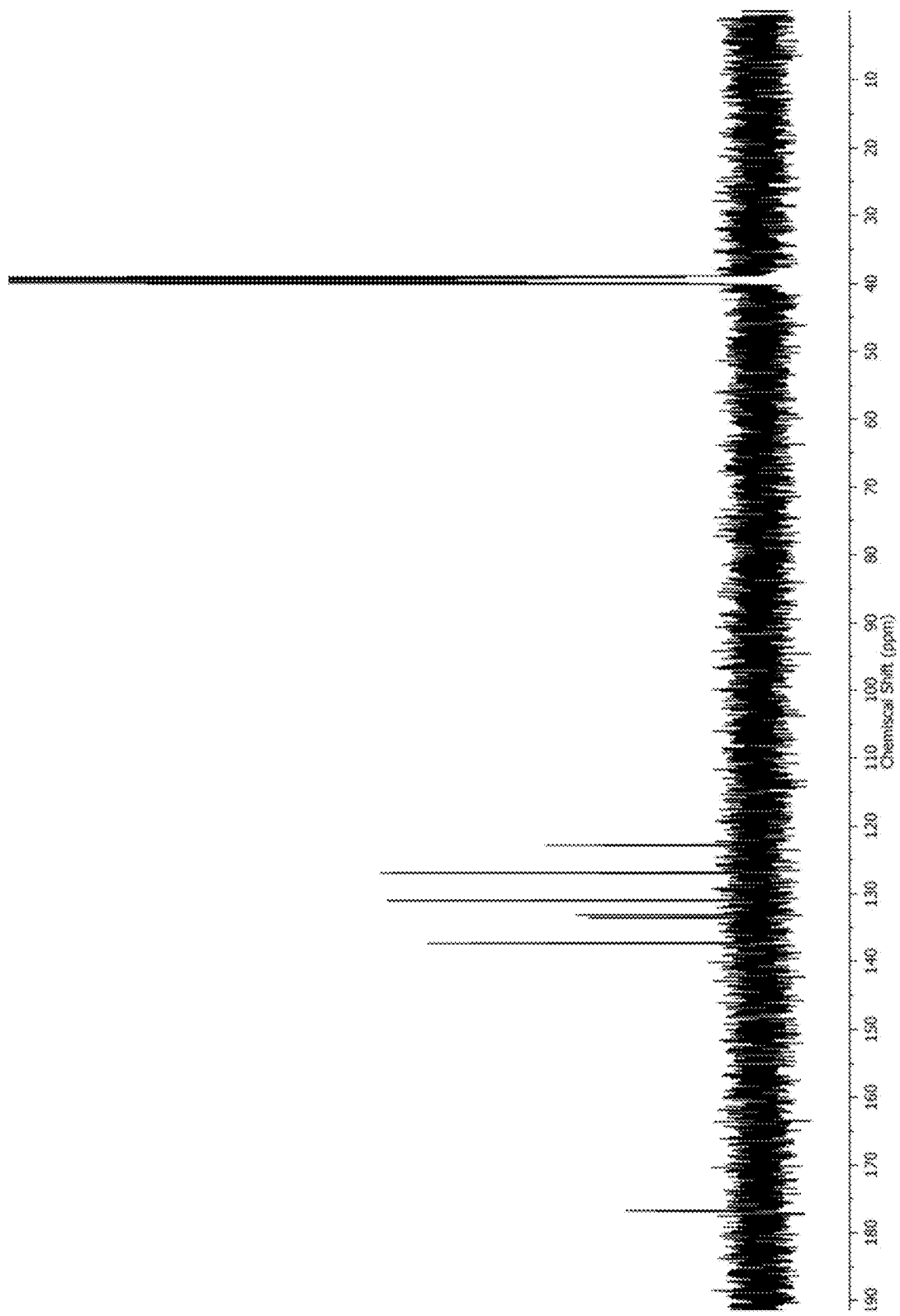
FIG. 32: is an example according to various embodiments, illustrating a characteristic $^{13}$CNMR (101 MHz, DMSO-$d_6$, 20° C.) spectra of compound S5 synthesized in the disclosed examples.

FIG. 32 shows $^{13}$C NMR (101 MHz, DMSO-d$_6$, 25° C.) δ (ppm) 176.73, 137.36, 133.55, 133.12, 130.97, 126.90, 122.81 spectra of compound S5.

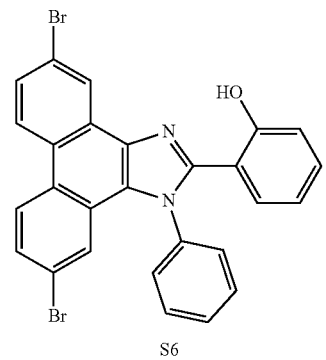

S6

2-(5,10-dibromo-1-phenyl-1H-phenanthro[9,10-d]imidazol-2-yl)-phenol (S6): Adapted from [3]. S5 (3.5 g, 9.56 mmol, 1.0 eq) and ammonium acetate (3.69 g, 47.81 mmol, 5.0 eq) were added to a 250 mL two neck flask equipped with a magnetic stir bar. The flask was purged with nitrogen gas three times as mentioned previously, and acetic acid (70 mL) was added, followed by aniline (1.75 mL, 19.13 mmol, 2.0 eq) and salicylaldehyde (1.02 mL, 9.56 mmol, 1.0 eq). The solution was heated to 120° C. After 12 h the solution was cooled to room temperature and quenched with water. The green precipitate was collected by vacuum filtration and rinsed with 40% aqueous acetic acid and pure water. The crude product was dissolved in CH$_2$Cl$_2$ and rinsed with brine (×1), dried over Na$_2$SO$_4$ and filtered through a silica plug to remove an insoluble brown material. The collected crude was dried in a rotary evaporator and subjected to column chromatography (SiO$_2$, 15-35% v/v CH$_2$Cl$_2$/hexanes) producing a yellow solid. Yield 3.18 g (61%).

Figure 33:
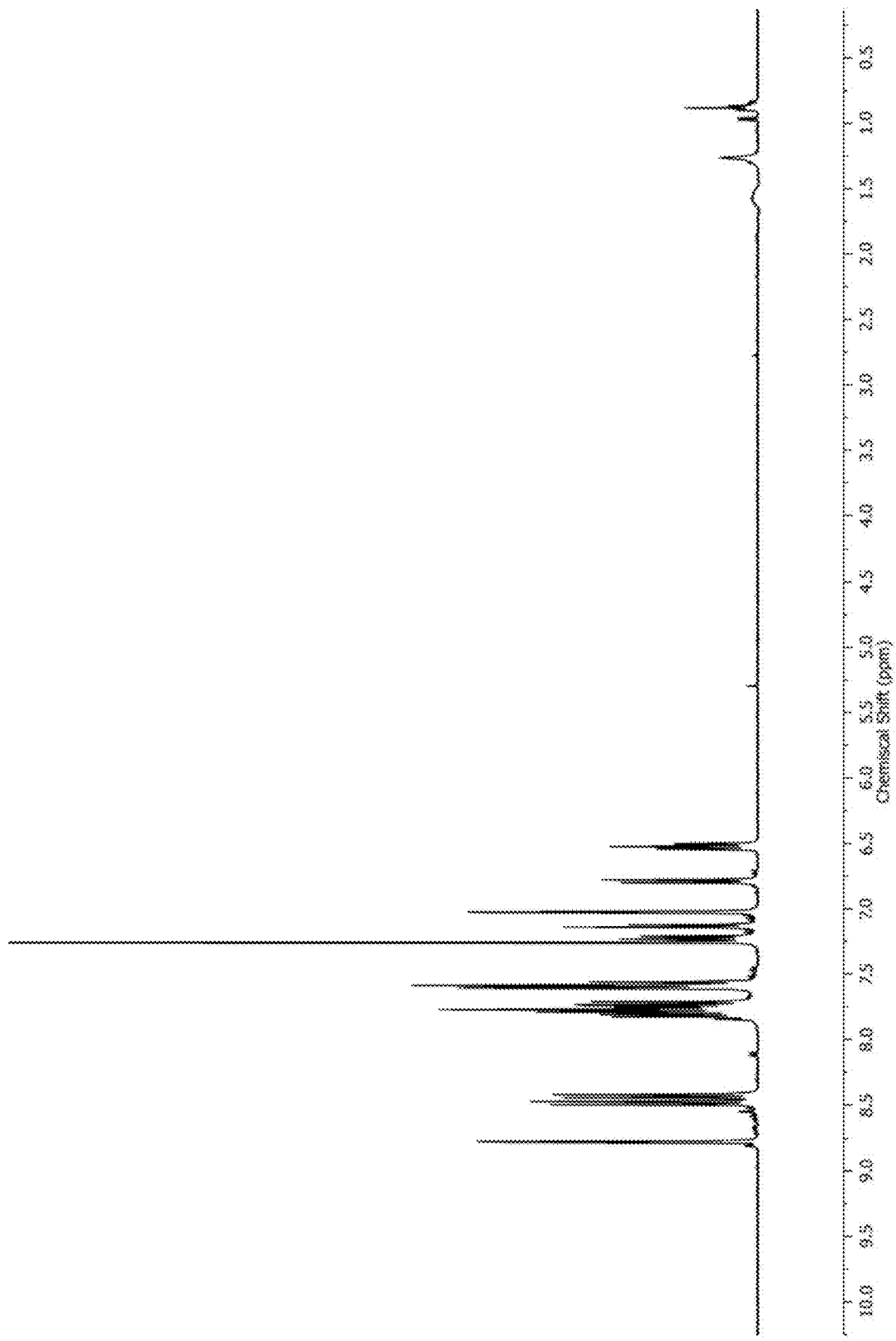
FIG. 33: is an example according to various embodiments, illustrating a characteristic $^1$HNMR (400 MHz, $CDCl_3$, 20° C.) spectra of compound S6 synthesized in the disclosed examples.

FIG. 33 shows $^1$HNMR (400 MHz, CDCl$_3$, 25° C.) δ (ppm) 8.78 (d, J=2.1 Hz, 1H), 8.48 (d, J=9.0 Hz, 1H), 8.43 (d, J=8.9 Hz, 1H), 7.84-7.71 (m, 4H), 7.60-7.56f (m, 3H), 7.25-7.21 (m, 1H), 7.13 (dd, J=8.3, 1.1 Hz, 1H), 7.02 (d, J=2.0 Hz, 1H), 6.79 (dd, J=8.2, 1.4 Hz, 1H), 6.52 (ddd, J=8.3, 7.2, 1.3 Hz, 1H) spectra of compound S6.

Figure 34:
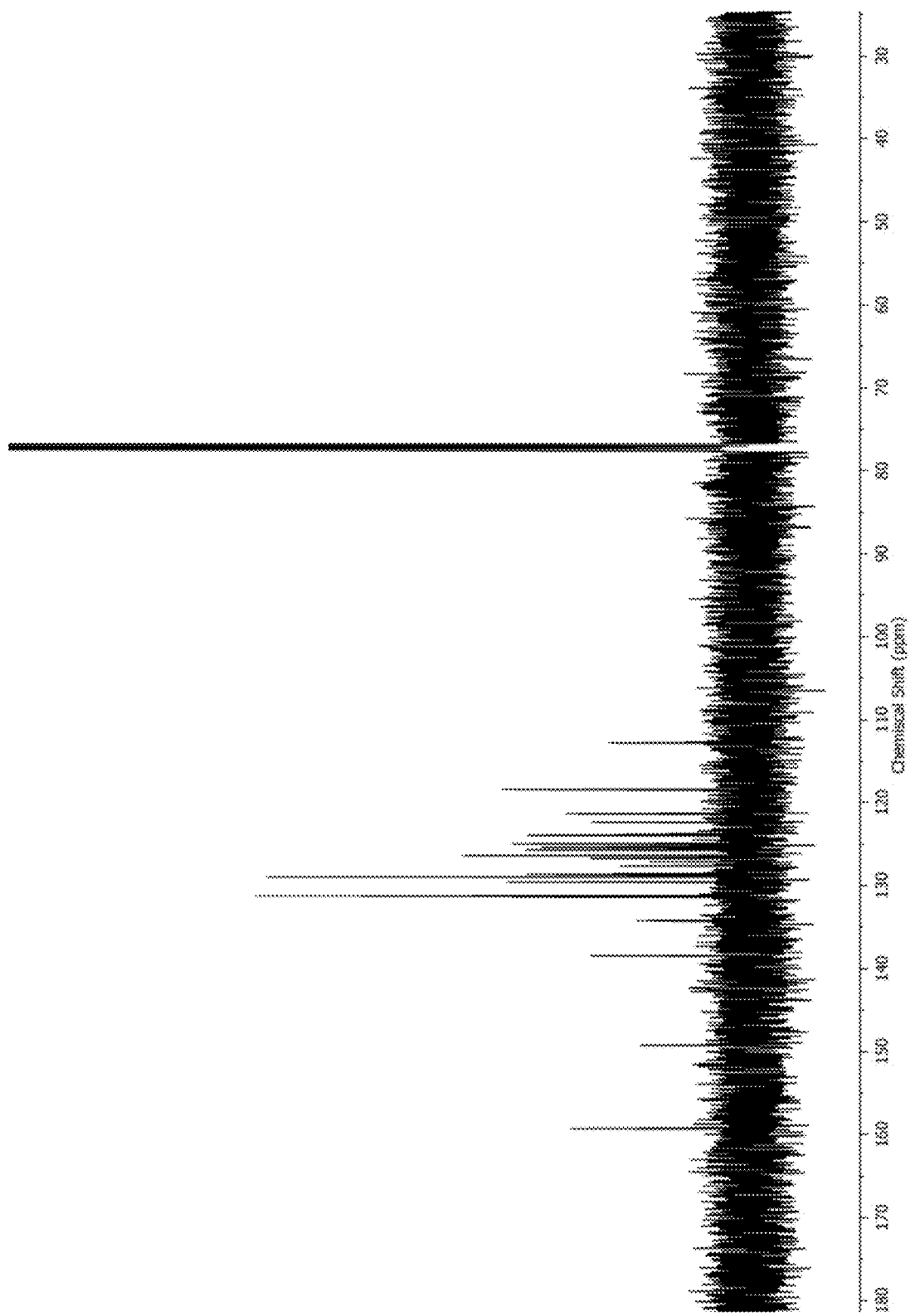
FIG. 34: is an example according to various embodiments, illustrating a characteristic $^{13}$CNMR (101 MHz, $CDCl_3$, 20° C.) spectra of compound S6 synthesized in the disclosed examples.

FIG. 34 shows $^{13}$C NMR (101 MHz, CDCl$_3$, 25° C.) δ (ppm) 159.31, 149.29, 138.43, 134.22, 131.37, 131.24, 131.14, 129.60, 128.95, 128.63, 127.64, 127.13, 126.73, 126.64, 126.40, 125.71, 125.40, 125.00, 123.96, 123.81, 122.39, 121.34, 118.41, 118.36, 112.78 spectra of compound S6.

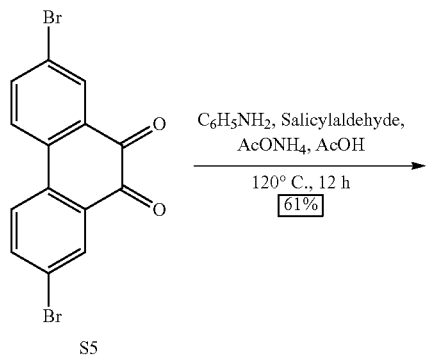

S5

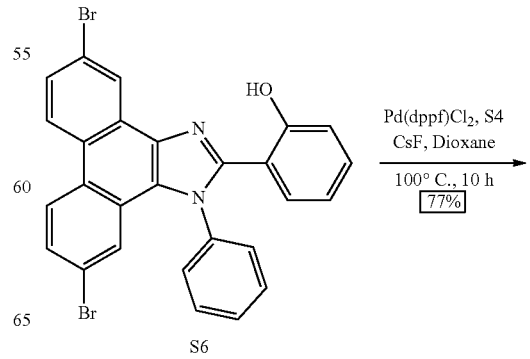

S6

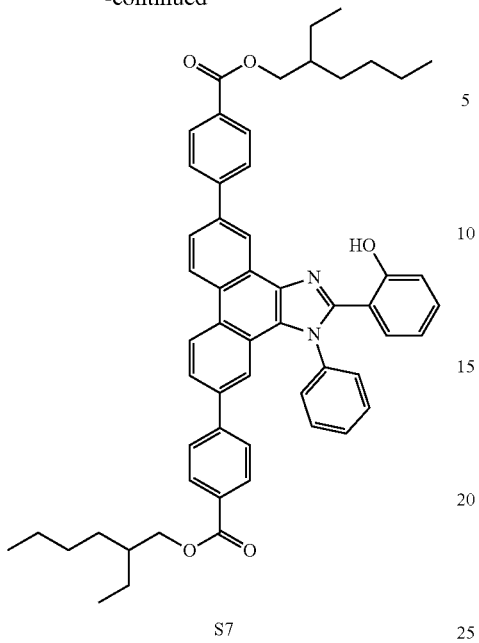

S7

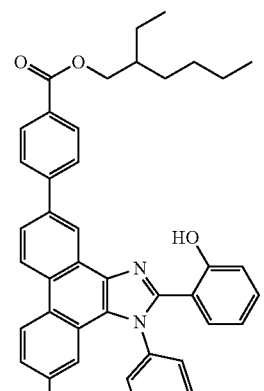

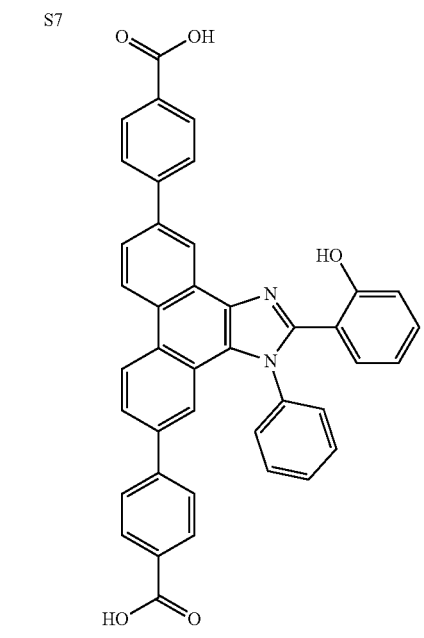

B linker 2-(5,10-bis-(2-ethylhexyl-4-benzoate)-1-phenyl-1H-phenanthro[9,10-d]imidazol-2-yl)-phenol (S7): S6 (1.8 g, 3.31 mmol, 1.0 eq), S4 (2.02 g, 7.28 mmol, 2.2 eq), CsF (3.01 g, 19.84 mmol, 6.0 eq), and Pd(dppf)Cl$_2$ (0.108 g, 0.132 mmol, 0.04 eq) were added to a 250 mL Schlenk flask equipt with a magnetic stir bar. The flask was purged three times with N$_2$ gas, as mentioned previously, and anhydrous dioxane (66 mL) was added. The reaction vessel was heated to 100° C. for 10 h. Upon cooling to room temperature the reaction was quenched with water and extracted with CH$_2$Cl$_2$ (×3). The CH$_2$Cl$_2$ was rinsed with brine, dried over Na$_2$SO$_4$, and filtered. The solvent was removed in a rotary evaporator and the residue was subjected to column chromatography (SiO$_2$, 15-25% v/v CH$_2$Cl$_2$/hexanes), where the column was pretreated with 3% v/v TEA in hexanes, to yield a yellow wax. Yield 1.58 g (82%).

Figure 35:
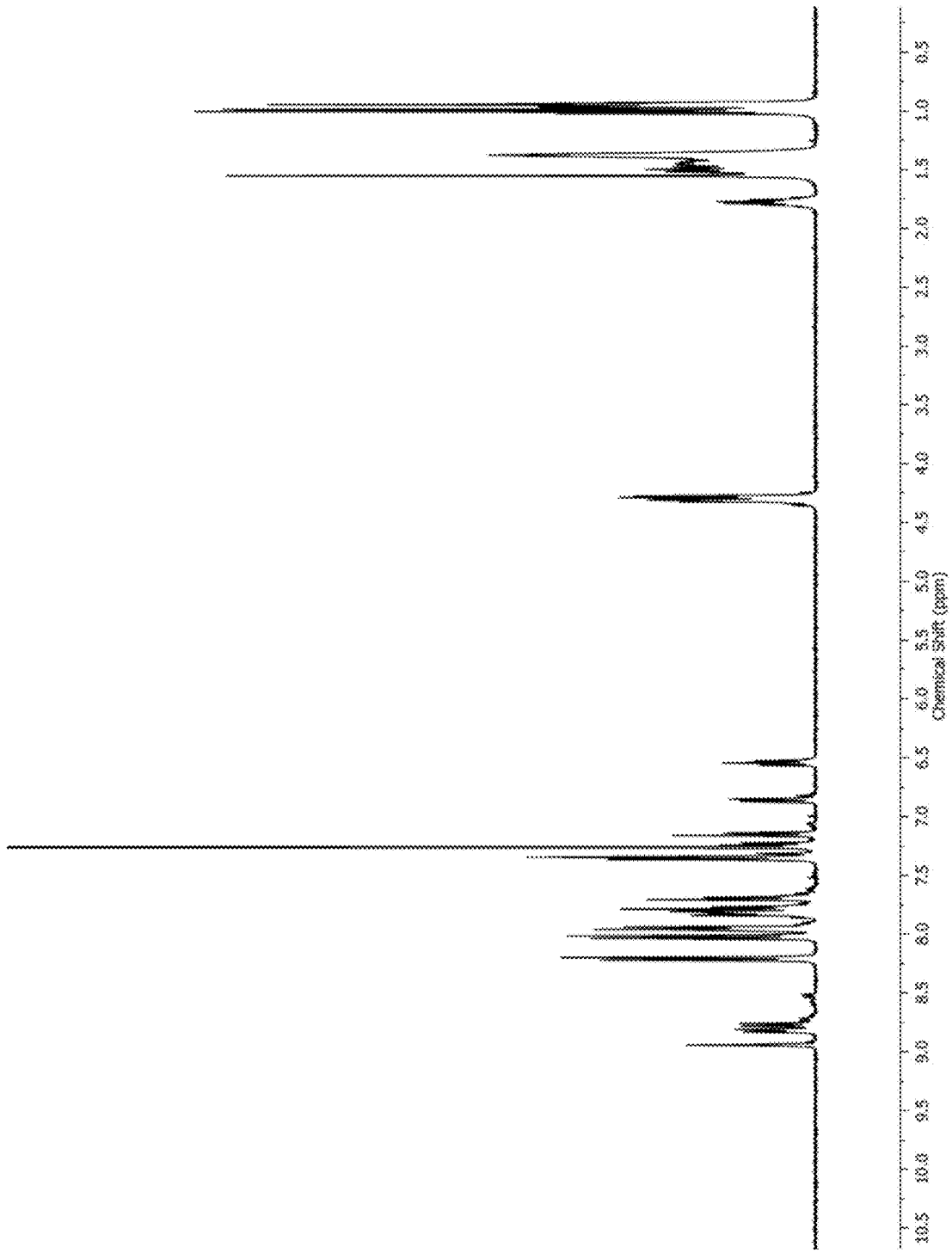
FIG. 35: is an example according to various embodiments, illustrating a characteristic $^1$HNMR (400 MHz, $CDCl_3$, 20° C.) spectra of compound S7 synthesized in the disclosed examples.

FIG. 35 shows $^1$HNMR (400 MHz, CDCl$_3$, 25° C.) δ (ppm) 8.92 (t, J=3.3 Hz, 1H), 8.76 (dd, J=19.1, 8.9 Hz, 2H), 8.20 (dd, J=8.4, 2.1 Hz, 2H), 8.06-7.98 (m, 2H), 7.98-7.89 (m, 3H), 7.86-7.73 (m, 4H), 7.72-7.63 (m, 2H), 7.34 (dq, J=9.3, 2.1 Hz, 3H), 7.23 (dd, J=7.0, 1.4 Hz, 1H), 7.15 (dd, J=8.2, 1.3 Hz, 1H), 6.88-6.81 (m, 1H), 6.54 (ddd, J=8.3, 7.1, 1.4 Hz, 1H), 4.32-4.27 (m, 4H), 1.80-1.75 (m, 2H), 1.54-1.39 (m, 16H), 1.04-0.95 (m, 12H) spectra of compound S7.

Figure 36:
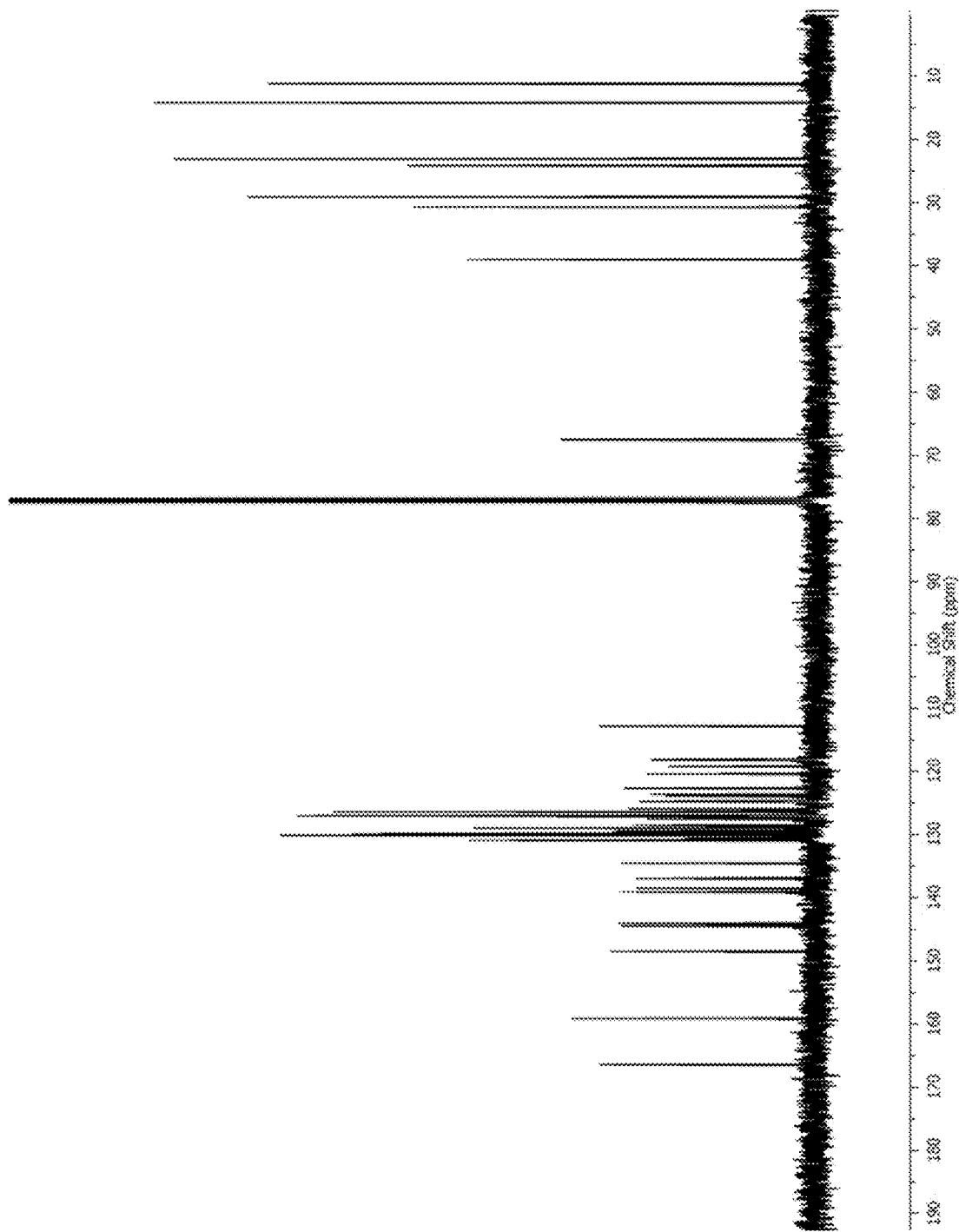
FIG. 36: is an example according to various embodiments, illustrating a characteristic $^{13}$CNMR (101 MHz, $CDCl_3$, 20° C.) spectra of compound S7 synthesized in the disclosed examples.

FIG. 36 shows $^{13}$C NMR (101 MHz, CDCl$_3$) δ (ppm) 166.63, 166.53, 159.23, 148.60, 144.53, 144.12, 139.14, 138.61, 137.08, 134.64, 131.05, 130.99, 130.69, 130.22, 130.00, 129.64, 129.49, 129.08, 128.63, 127.63, 127.29, 127.17, 126.54, 126.11, 126.08, 124.86, 124.04, 123.75, 122.80, 120.57, 119.37, 118.25, 118.14, 112.90, 67.60, 67.51, 39.08, 39.03, 30.76, 30.71, 29.14, 29.12, 24.18, 24.13, 23.15, 23.13, 14.23, 14.21, 11.28, 11.23 spectra of compound S7.

Figure 13:
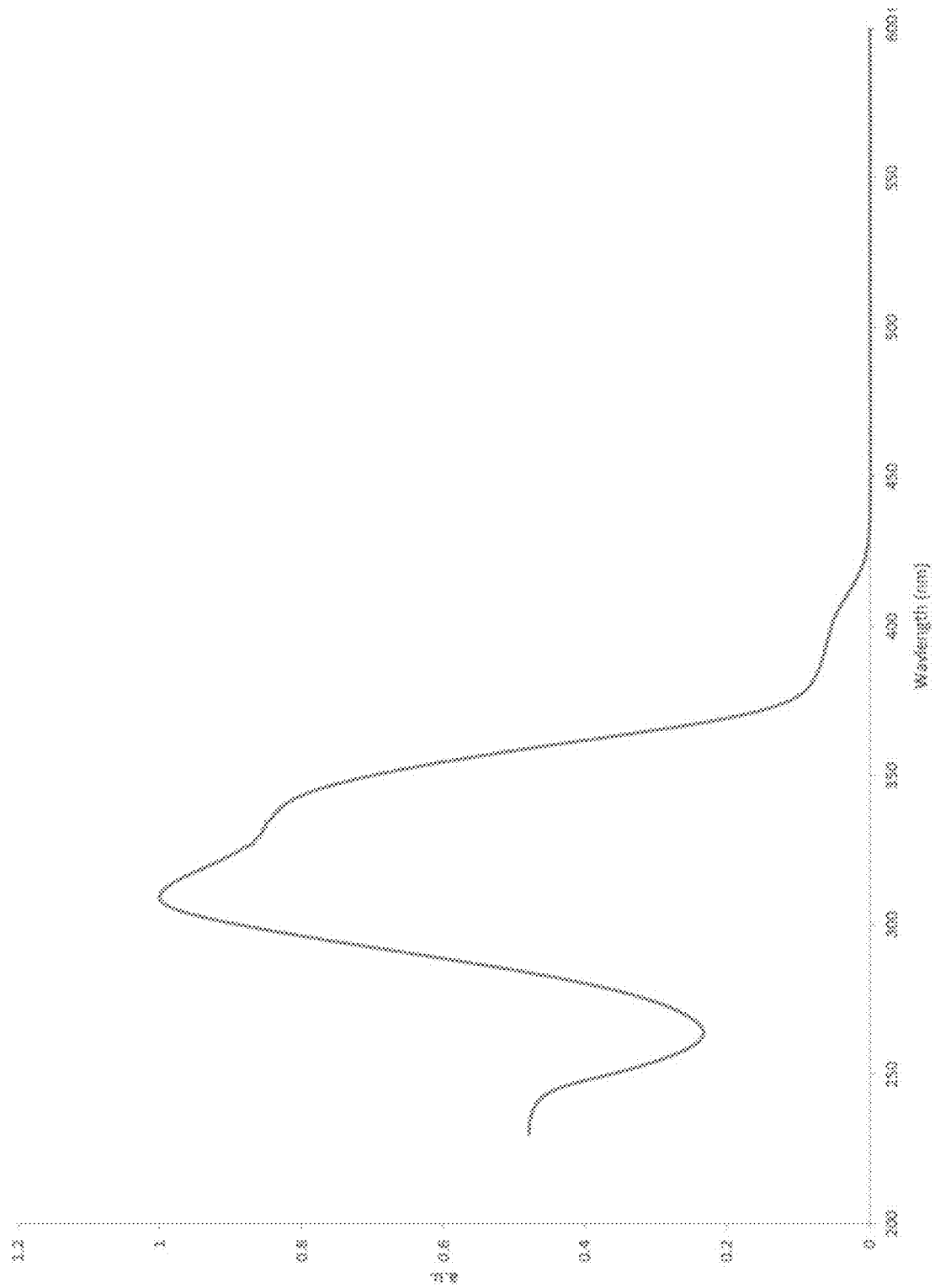
FIG. 13: is an example according to various embodiments illustrating a solid-state absorbance spectrum of compound S7 (as synthesized in the Examples) in 1,2-Dichloroethane (DCE)
Figure 16:
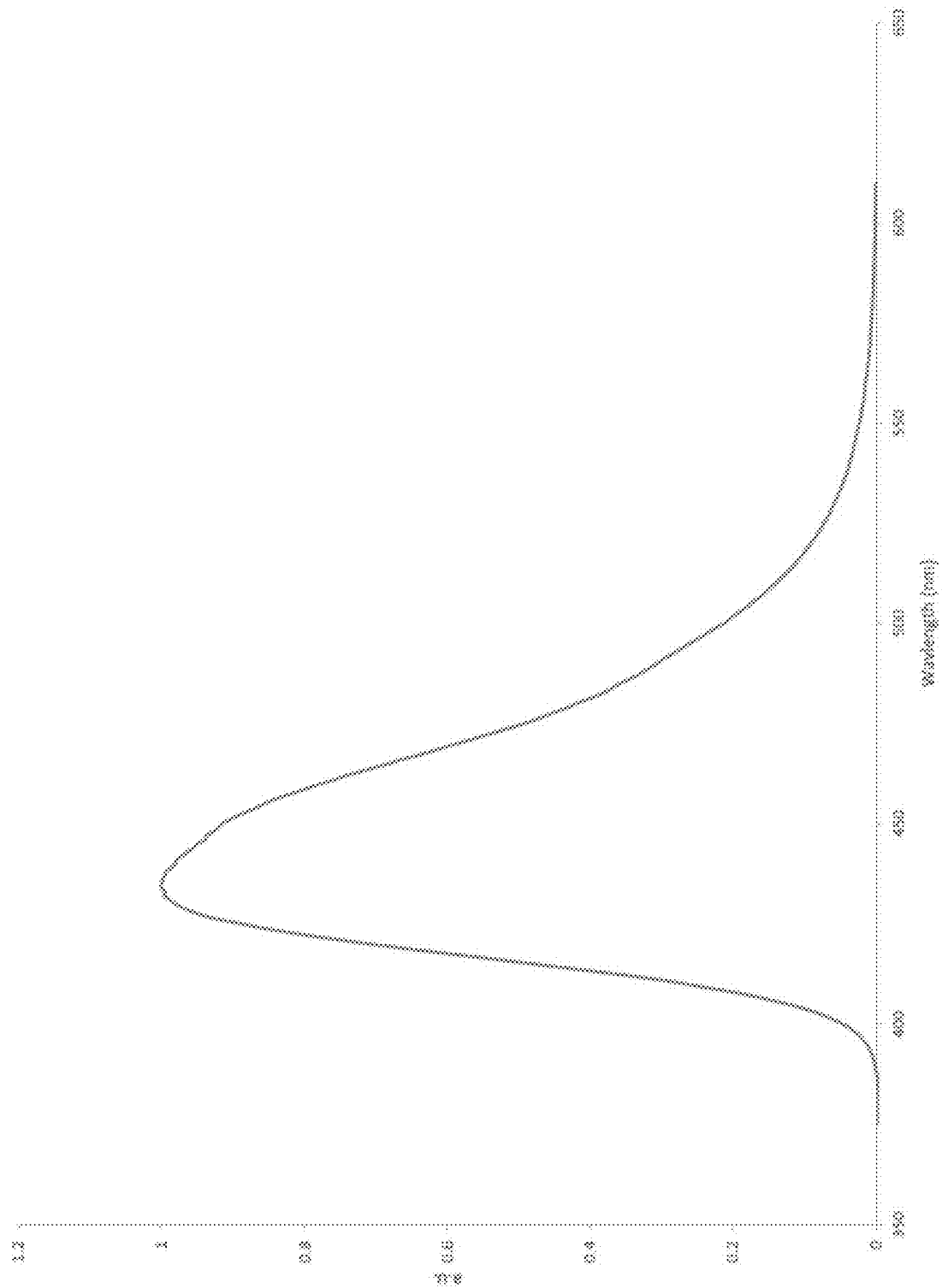
FIG. 16: is an example according to various embodiments illustrating a solid-state fluorescence spectrum of compound S7 (as synthesized in the Examples) in DCE.

FIG. 13: is an example according to various embodiments illustrating a solid-state absorbance spectrum of compound S7 (as synthesized in the Examples) in 1,2-Dichloroethane (DCE);

FIG. 16: is an example according to various embodiments illustrating a solid-state fluorescence spectrum of compound S7 (as synthesized in the Examples) in DCE;

2-(5,10-bis-(4-benzoic acid)-1-phenyl-1H-phenanthro[9,10-d]imidazol-2-yl)-phenol (B linker): S7 (1.58 g, 1.86 mmol, 1.0 eq) was added to a 500 mL round bottom flask with 124 mL of THF. 5 M KOH in methanol (18.6 mL, 92.8 mmol, 50 eq) was added to the THF solution. The solution was heated to reflux overnight. The volatile solvents were then removed in a rotary evaporator. The resulting residue was dissolved in 200 mL of water and quenched with 3M H$_2$SO$_4$ till the solution was acidic and a yellow solid had crashed out of the solution. The precipitate was collected by vacuum filtration and rinsed with water and cold methanol. Yield 1.1 g (95%).

Figure 37:
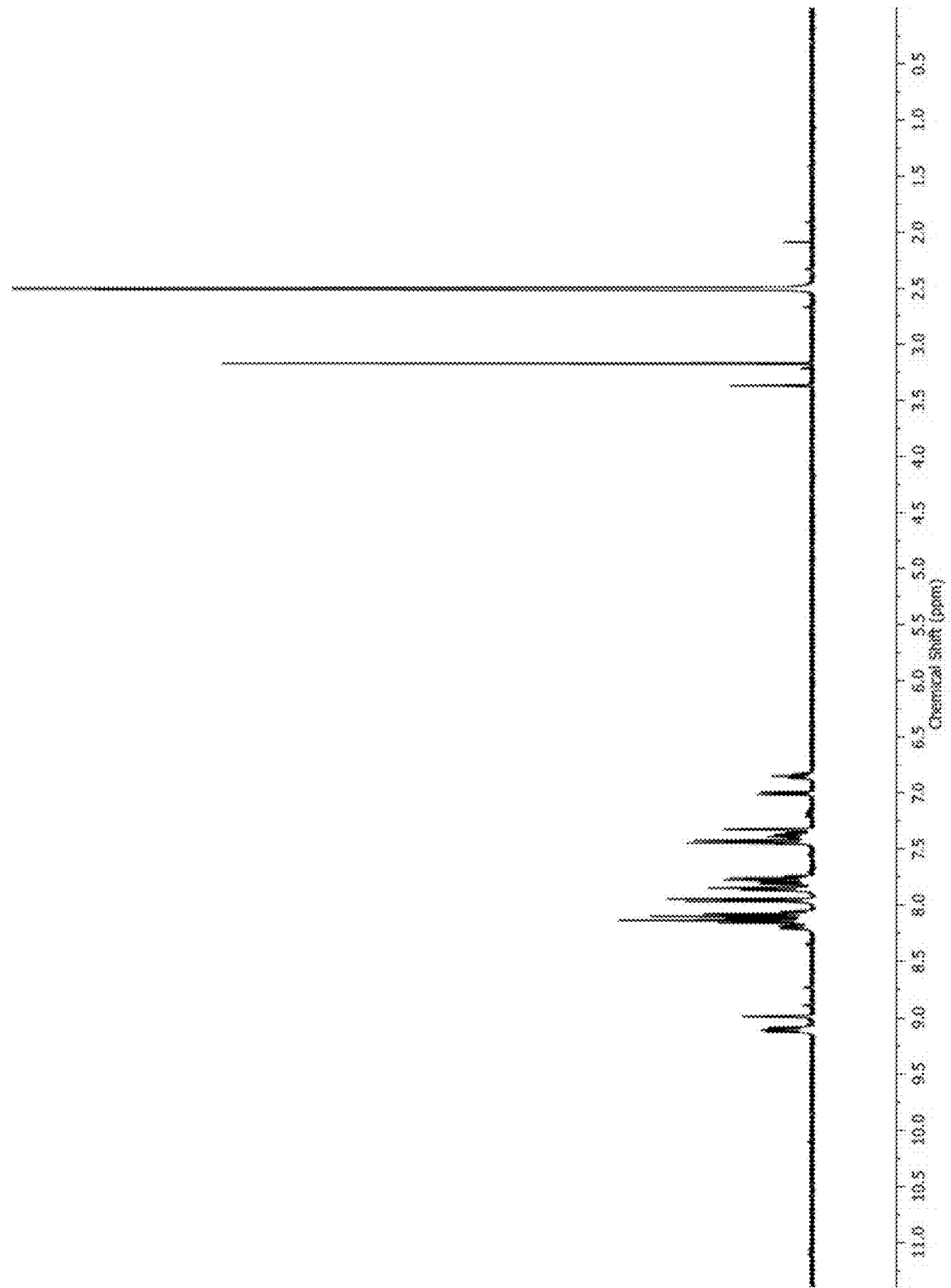
FIG. 37: is an example according to various embodiments, illustrating a characteristic $^1$HNMR (400 MHz, DMSO-$d_6$, 20° C.) spectra of a blue linker compound synthesized in the disclosed examples.

FIG. 37 shows $^1$HNMR (400 MHz, DMSO-d6) δ (ppm) 9.00 (dd, J=12.9, 8.7 Hz, 2H), 8.90 (d, J=2.1 Hz, 1H), 8.17-8.02 (m, 5H), 7.99-7.89 (m, 3H), 7.76 (dq, J=15.1, 8.4 Hz, 5H), 7.42 (d, J=8.3 Hz, 2H), 7.32 (d, J=2.0 Hz, 1H), 7.25 (d, J=8.6 Hz, 1H), 7.21-7.15 (m, 1H), 6.96 (d, J=8.2 Hz, 1H), 6.72 (t, J=7.6 Hz, 1H) spectra of blue linker.

Figure 38:
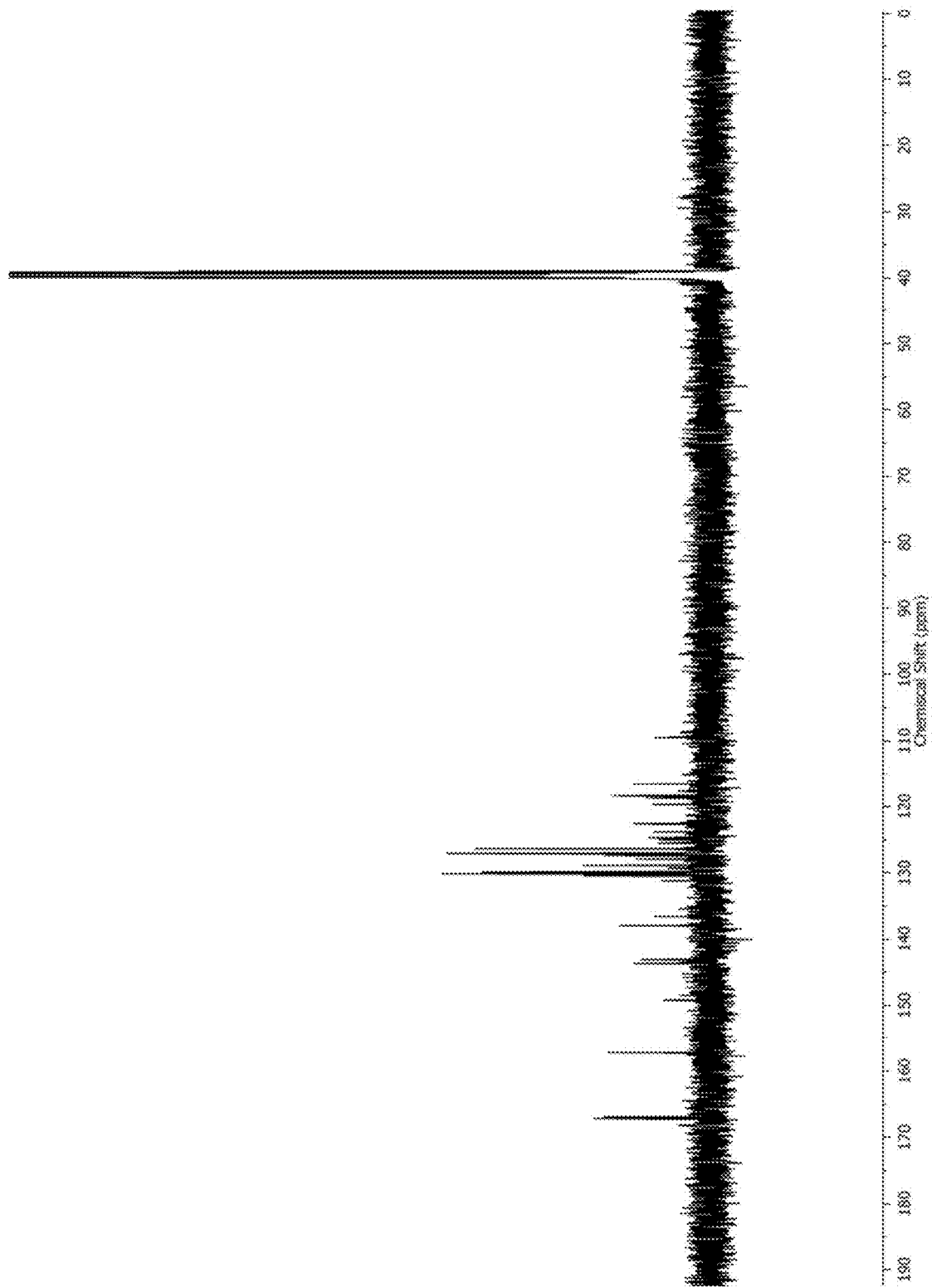
FIG. 38: is an example according to various embodiments, illustrating a characteristic $^{13}$CNMR (101 MHz, DMSO-$d_6$, 20° C.) spectra of a blue linker compound synthesized in the disclosed examples.

FIG. 38 shows $^{13}$C NMR (101 MHz, CDCl$_3$, 25° C.) δ (ppm) 167.13, 166.94, 157.18, 149.18, 143.66, 143.09, 137.95, 136.56, 131.18, 130.45, 130.37, 130.15, 129.92, 129.89, 129.25, 128.87, 128.83, 127.91, 127.34, 127.16, 127.07, 126.37, 125.56, 124.98, 124.68, 123.82, 122.60, 122.58, 119.67, 118.66, 118.35, 116.55, 109.51 spectra of blue linker.

Example 3

A purpose of this example is to illustrate a general synthetic scheme of an orange linker (also referenced in FIG. 2D).

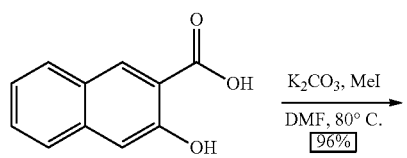
K$_2$CO$_3$, MeI
DMF, 80° C.
96%

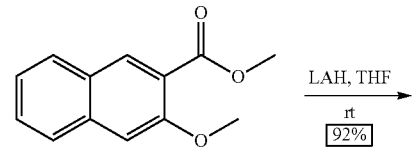
S8
LAH, THF
rt
92%

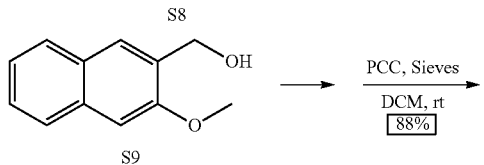
S9
PCC, Sieves
DCM, rt
88%

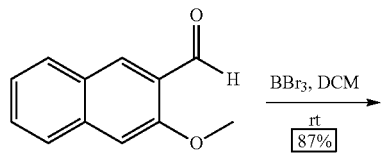
S10
BBr$_3$, DCM
rt
87%

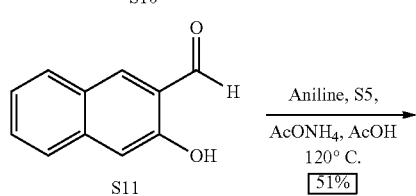
S11
Aniline, S5,
AcONH$_4$, AcOH
120° C.
51%

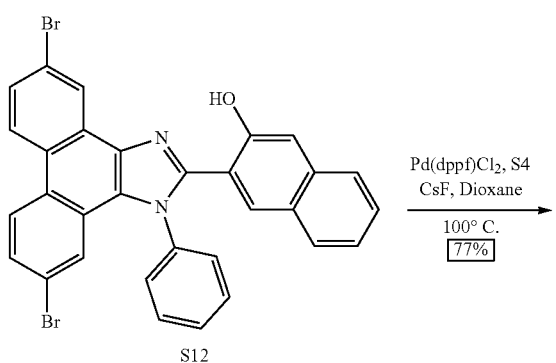
S12
Pd(dppf)Cl$_2$, S4
CsF, Dioxane
100° C.
77%

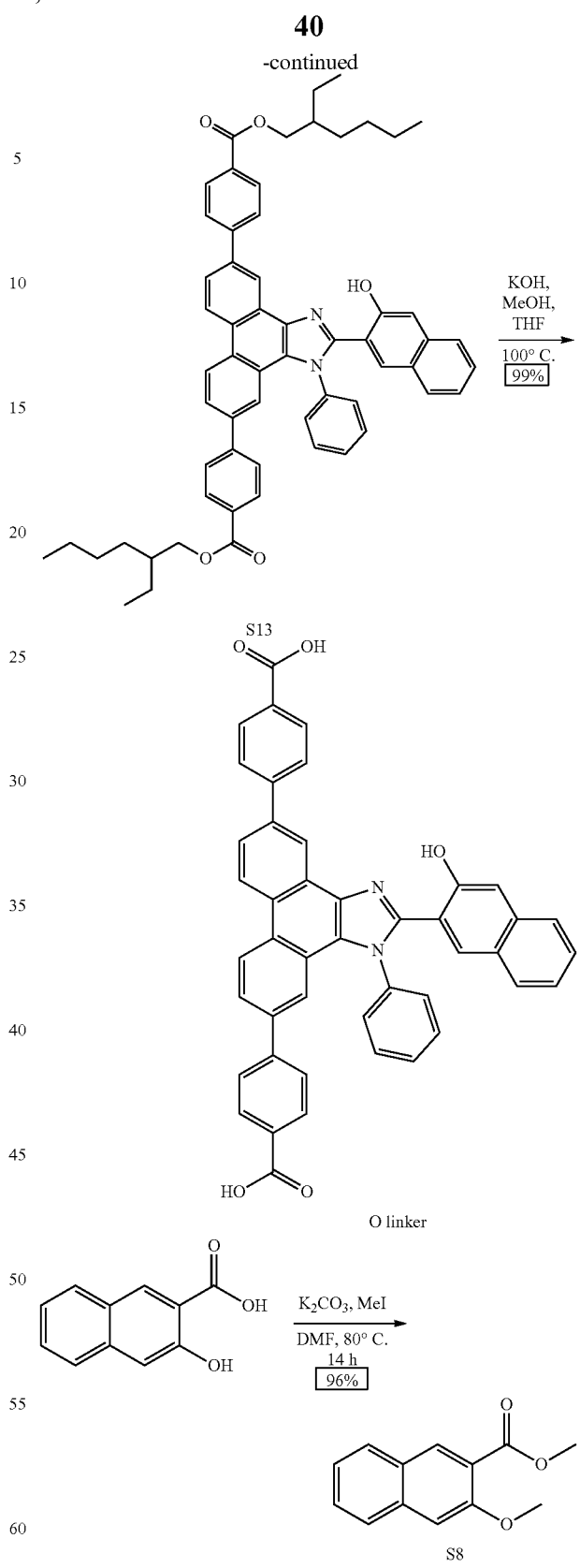

KOH, MeOH, THF
100° C.
99%

S13

O linker

K$_2$CO$_3$, MeI
DMF, 80° C.
14 h
96%

S8

Methyl 3-methoxy-2-naphthanoate (S8): Adapted from [4] 3-hydroxy-2-naphthanoic acid (5.0 g, 26.6 mmol, 1.0 eq) and K$_2$CO$_3$ (14.7 g, 106.3 mmol, 4.0 eq) were added to a 250 mL round bottom flask. The flask was evacuated to 150 mtorr and back filled with nitrogen gas three times. Anhydrous DMF (60 mL) was then added and stirred in the round bottom flask. MeI (8.60 mL, 138.2 mmol, 5.2 eq) was added to the flask and the mixture was heated to 80° C. for 24 h. After which the vessel was cooled to room temperature and the excess carbonate was quenched by the addition of 3 M $H_2SO_4$. The solution was then diluted to 500 mL using DI water. The solution was extracted with EtOAc (×3). The combined organic extracts were rinsed with 75 mL of 2 M LiCl (×1), 175 mL water (×3), and brine (×1) after which the EtOAc was dried over $Na_2SO_4$ and filtered. The ethyl acetate was removed using a rotary evaporator and the crude product was subjected to column chromatography, ($SiO_2$, 7% v/v EtOAc/hexanes). Yield 5.48 g (96%).

Figure 39:
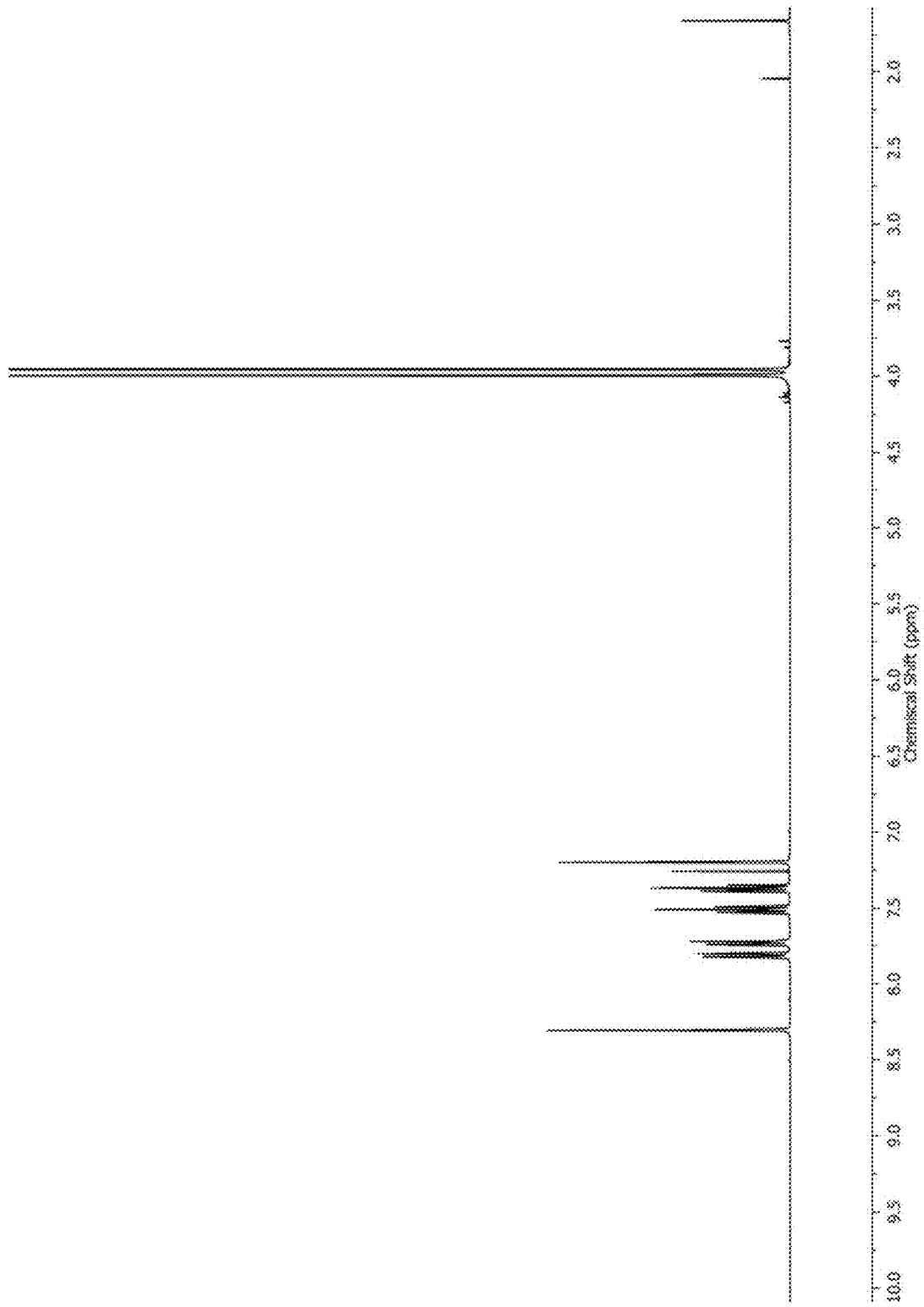
FIG. 39: is an example according to various embodiments, illustrating a characteristic $^1$HNMR (400 MHz, $CDCl_3$, 20° C.) spectra of compound S8 synthesized in the disclosed examples.

FIG. 39 shows $^1$HNMR (400 MHz, $CDCl_3$, 25° C.) δ (ppm) 8.30 (s, 1H), 7.81 (d, J=8.9 Hz, 1H), 7.73 (d, J=9.0 Hz, 1H), 7.51 (t, J=8.2 Hz, 1H), 7.37 (t, J=8.1 Hz, 1H), 7.20 (s, 1H), 3.98 (d, J=15.4 Hz, 6H) spectra of compound S8.

Figure 40:
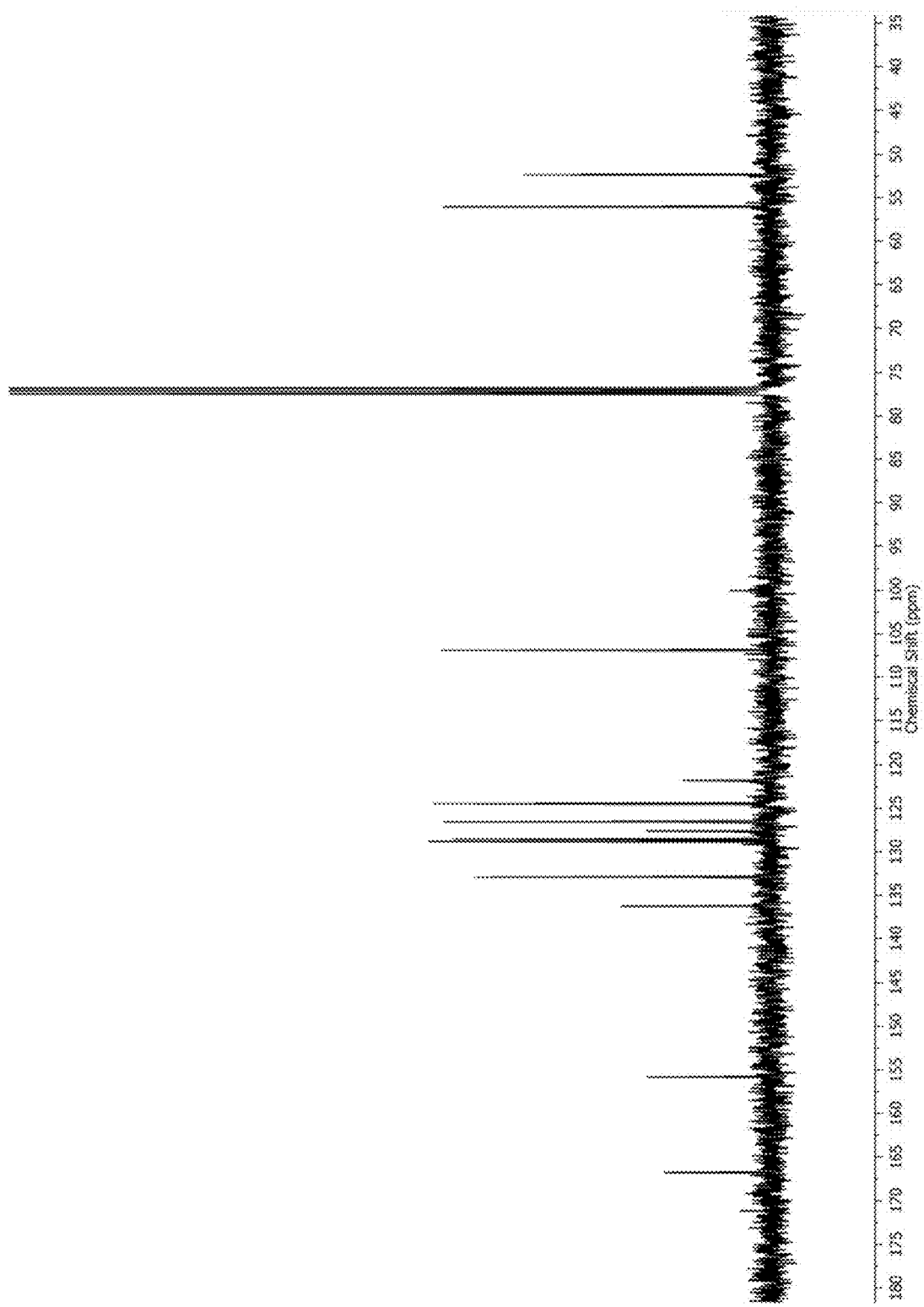
FIG. 40: is an example according to various embodiments, illustrating a characteristic $^{13}$CNMR (101 MHz, $CDCl_3$, 20° C.) spectra of compound S8 synthesized in the disclosed examples.

FIG. 40 shows $^{13}$C NMR (101 MHz, $CDCl_3$, 25° C.) δ (ppm) 166.80, 155.81, 136.20, 132.89, 128.79, 128.52, 127.62, 126.55, 124.50, 121.80, 106.88, 77.16, 56.09, 52.38 spectra of compound S8.

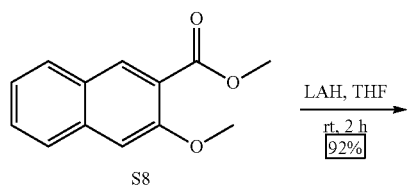

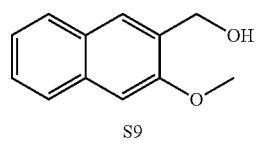

3-Methoxy-2-naphthalenemethanol (S9): Adapted from [5]. LAH (1.924 g, 50.68 mmol, 2.0 eq) was collected in a 250 mL schlenk flask from an argon filled glove box. Anhydrous THF (118 mL) was added to the LAH and stirred into a slurry, which was then lowered into an ice bath. In a separate 50 mL schlenk flask S8 was purged with $N_2$ gas and anhydrous THF (29 mL) was added. The solution of S8 was added slowly over the course of 15 min to the mixing LAH slurry. Upon completion of the reaction, as monitored by TLC, of the addition the ice bath was removed and the reaction was allowed to mix at room temperature for 2 h. The reaction was then quenched with ice water and extracted 3 times with $CH_2Cl_2$. The $CH_2Cl_2$ was rinsed with brine, dried over $Na_2SO_4$, and filtered. The $CH_2Cl_2$ was removed in a rotary evaporator and the crude was purified using column chromatography ($SiO_2$, 25% v/v EtOAc/hexanes) to yield a white solid. Yield 4.37 g (92%).

Figure 41:
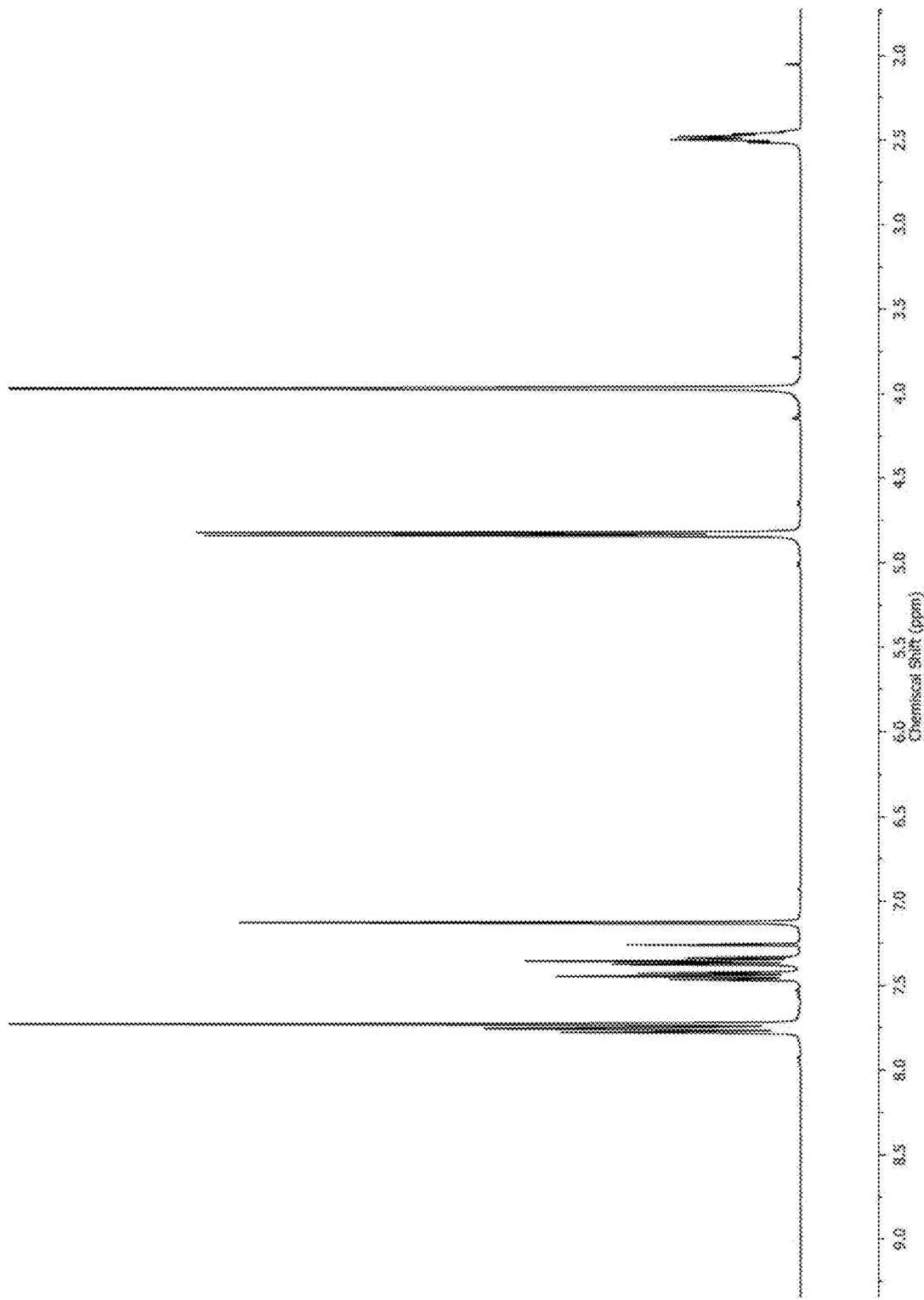
FIG. 41: is an example according to various embodiments, illustrating a characteristic $^1$HNMR (400 MHz, $CDCl_3$, 20° C.) spectra of compound S9 synthesized in the disclosed examples.

FIG. 41 shows $^1$HNMR (400 MHz, $CDCl_3$, 25° C.) δ (ppm) 7.81-7.70 (m, 3H), 7.45 (d, J=16.3 Hz, 1H), 7.36 (d, J=15.8 Hz, 1H), 7.13 (s, 1H), 4.83 (d, J=6.5 Hz, 2H), 3.97 (s, 3H), 2.49 (d, J=19.9 Hz, 1H) spectra of compound S9.

Figure 42:
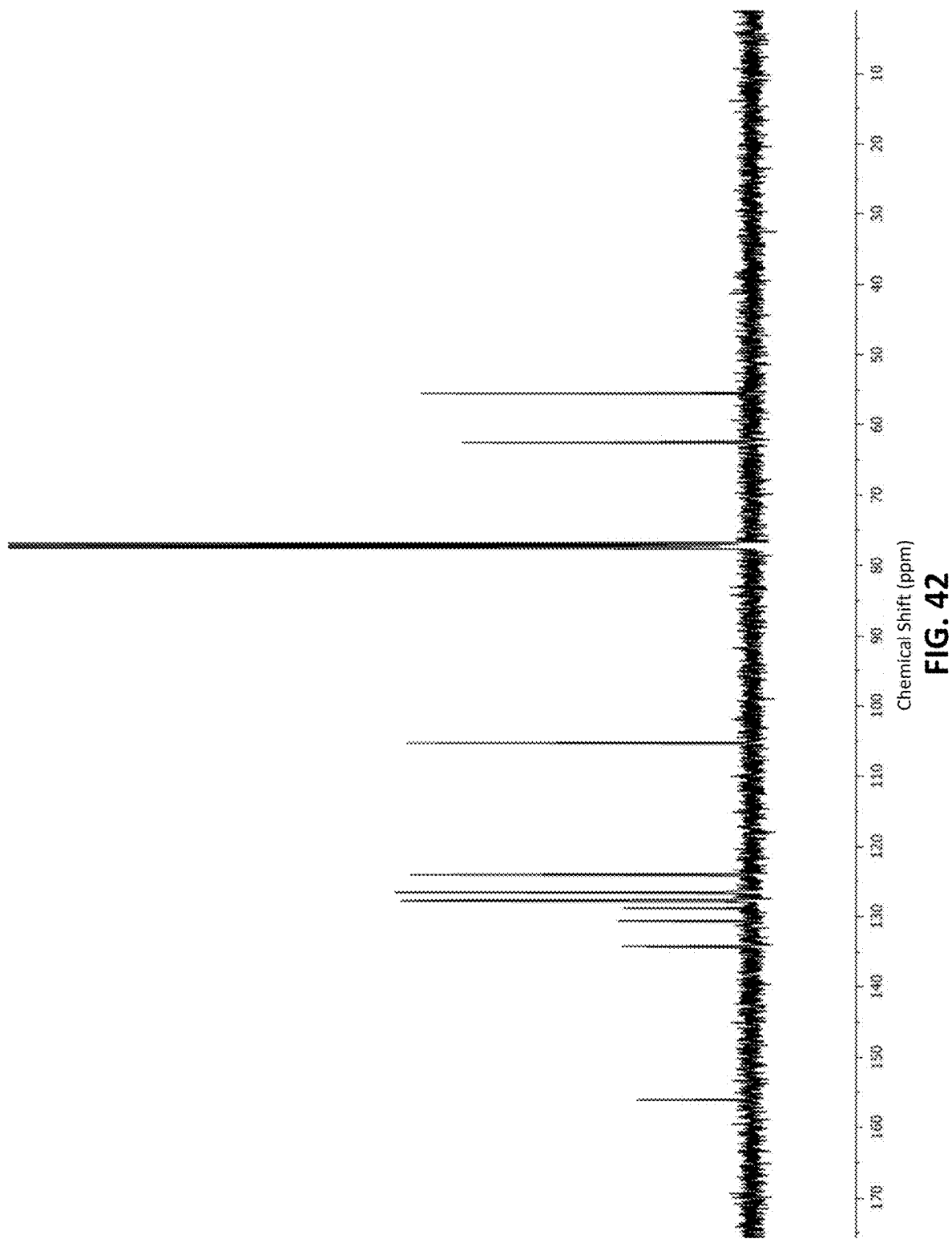
FIG. 42: is an example according to various embodiments, illustrating a characteristic $^{13}$CNMR (101 MHz, $CDCl_3$, 20° C.) spectra of compound S9 synthesized in the disclosed examples.

FIG. 42 shows $^{13}$C NMR (101 MHz, $CDCl_3$, 25° C.) δ (ppm) 156.03, 134.23, 130.61, 128.79, 127.78, 127.64, 126.56, 126.44, 124.05, 105.28, 77.16, 62.55, 55.48 spectra of compound S9.

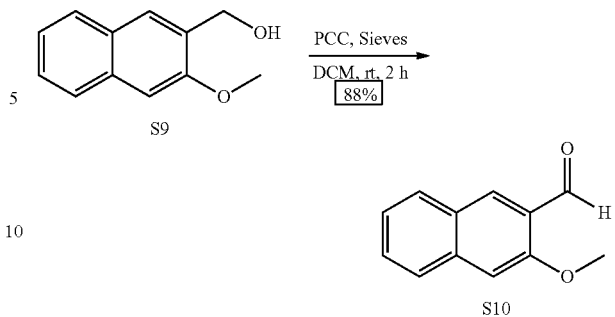

3-Methoxy-2-naphthaldehyde (S10): Adapted from [5]. Pyridinium Chlorochromate, PCC, (7.51 g, 34.8 mmol, 1.5 eq) and potassium acetate (3.42 g, 34.8 mmol, 1.5 eq) were added to a 250 mL schlenk flask. The flask was purged with $N_2$ gas as previously mentioned. Then 3 g of activated molecular sieves were added. S9 was placed in a separate schlenk flask and purged with $N_2$ gas. Anhydrous $CH_2Cl_2$ was added to each flask, 70 mL to the PCC flask and 35 mL to the second flask. The PCC solution was cooled to 0° C. and the S9 solution was added dropwise to the PCC solution over 5 minutes as the solution turned brown. Upon completion of the addition of S9 the reaction vessel was warmed up to room temperature and allowed to mix for 2 h. Upon completion of the reaction all insoluble material was filtered off and rinsed with diethyl ether. The $CH_2Cl_2$ and ether were combined and removed in a rotary evaporator. The crude product was purified by column chromatography ($SiO_2$, 40% v/v EtOAc/hexanes) to yield a yellow solid. Yield 3.79 g (88%).

Figure 43:
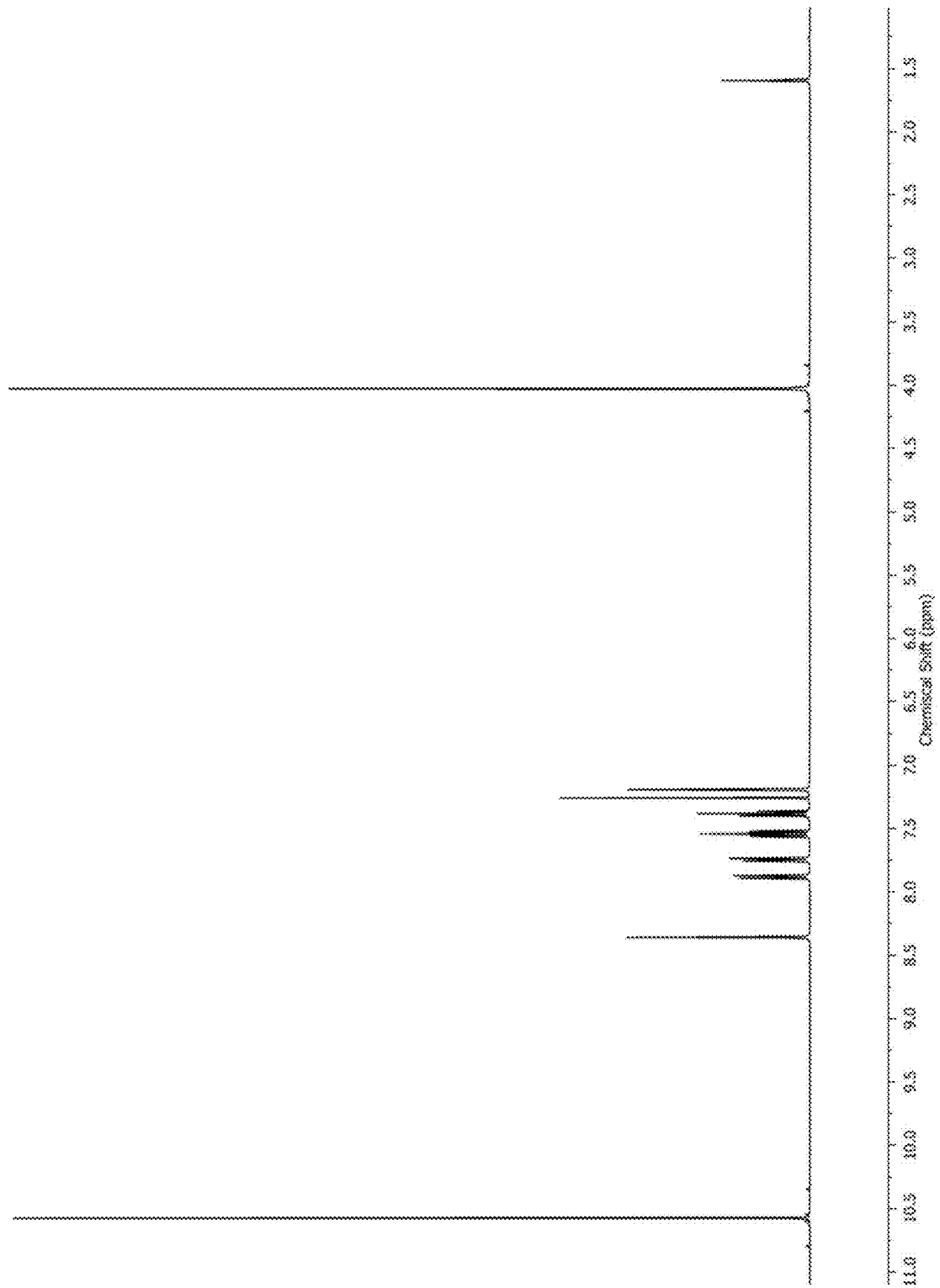
FIG. 43: is an example according to various embodiments, illustrating a characteristic $^1$HNMR (400 MHz, $CDCl_3$, 20° C.) spectra of compound S10 synthesized in the disclosed examples.

FIG. 43 shows $^1$HNMR (400 MHz, $CDCl_3$, 25° C.) δ (ppm) 10.58 (s, 1H), 8.36 (s, 1H), 7.88 (d, J=9.0 Hz, 1H), 7.74 (d, J=9.1 Hz, 1H), 7.54 (t, J=8.2 Hz, 1H), 7.38 (t, J=8.1 Hz, 1H), 7.19 (s, 1H), 4.03 (s, 3H) spectra of compound S10.

Figure 44:
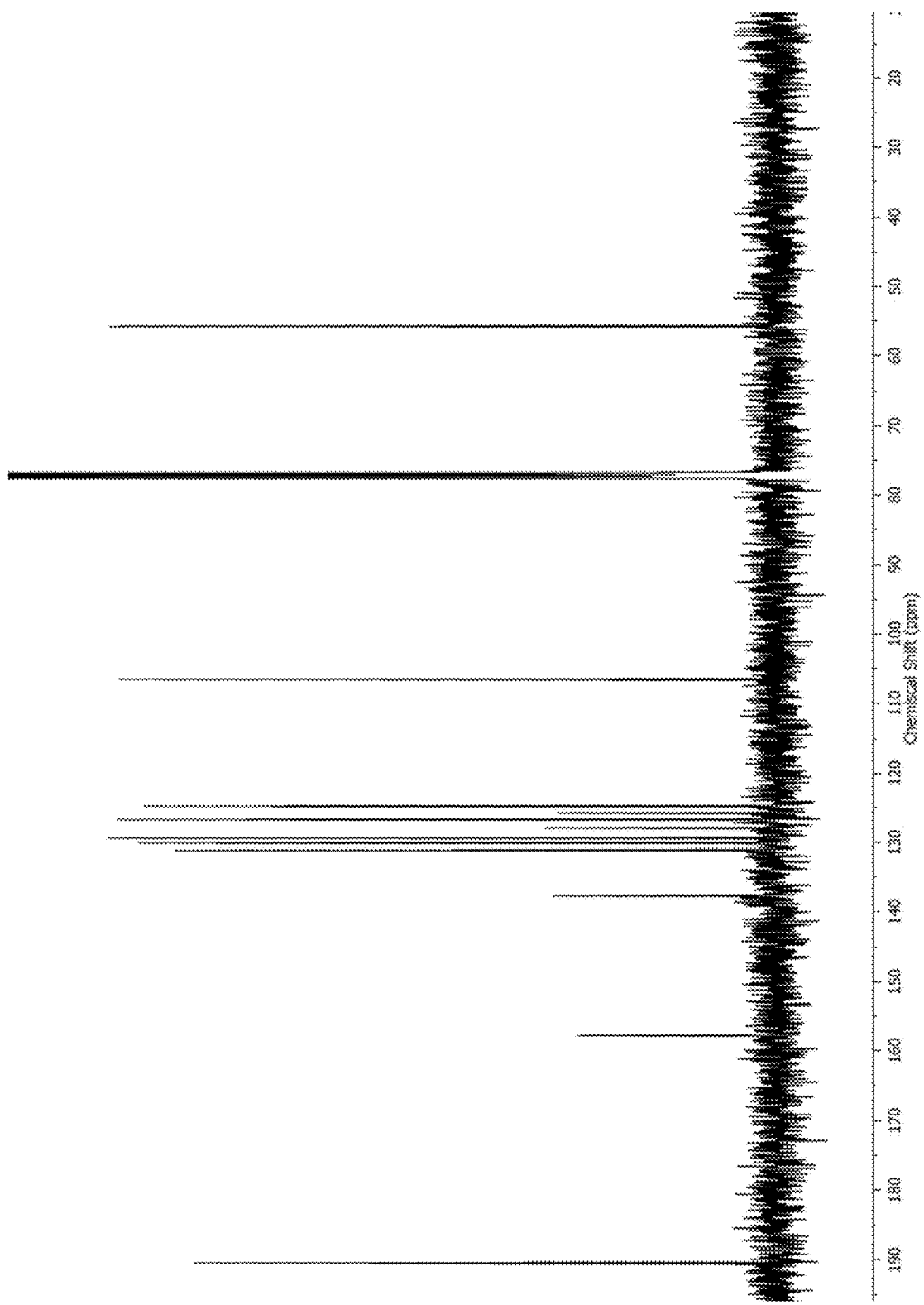
FIG. 44: is an example according to various embodiments, illustrating a characteristic $^{13}$CNMR (101 MHz, $CDCl_3$, 20° C.) spectra of compound S10 synthesized in the disclosed examples.

FIG. 44 shows $^{13}$C NMR (101 MHz, $CDCl_3$, 25° C.) δ (ppm) 190.42, 157.76, 137.68, 131.14, 130.07, 129.36, 127.91, 126.75, 125.77, 124.79, 106.50, 77.16, 55.79 spectra of compound S10.

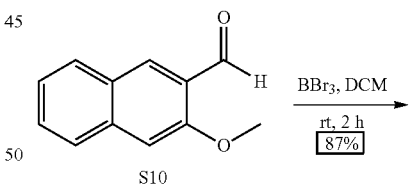

3-Methoxy-2-naphthaldehyde (S11): Adapted from [5]. S10 (2.76 g, 14.82 mmol, 1.0 eq) was placed in a 50 mL 2 neck flask and purged with $N_2$ gas. Anhydrous $CH_2Cl_2$ (27.4 mL) was added to the flask. A 100 mL schlenk flask was purged with $N_2$ 3 times before the addition of $BBr_3$ (1.69 mL, 17.78 mmol, 1.2 eq). Anhydrous $CH_2Cl_2$ (27.8 mL) was added to the $BBr_3$ flask, which was then cooled to 0° C. The solution of S10 was then added slowly to the $BBr_3$ solution over 5 minutes. Upon completion of the addition the flask was warmed to room temperature and stirred for one hour. The reaction was quenched with 150 mL of saturated NaHCO₃. The CH₂Cl₂ was collected and the aqueous phase was extracted with EtOAc 3 times. The combined organic phases were rinsed with brine, dried over Na₂SO₄, and filtered. The organic solvent was removed with a rotary evaporator and the crude product was purified using column chromatography (SiO₂, 30% v/v EtOAc/hexanes) resulting in a bright yellow solid. Yield 2.21 g (87%).

Figure 45:
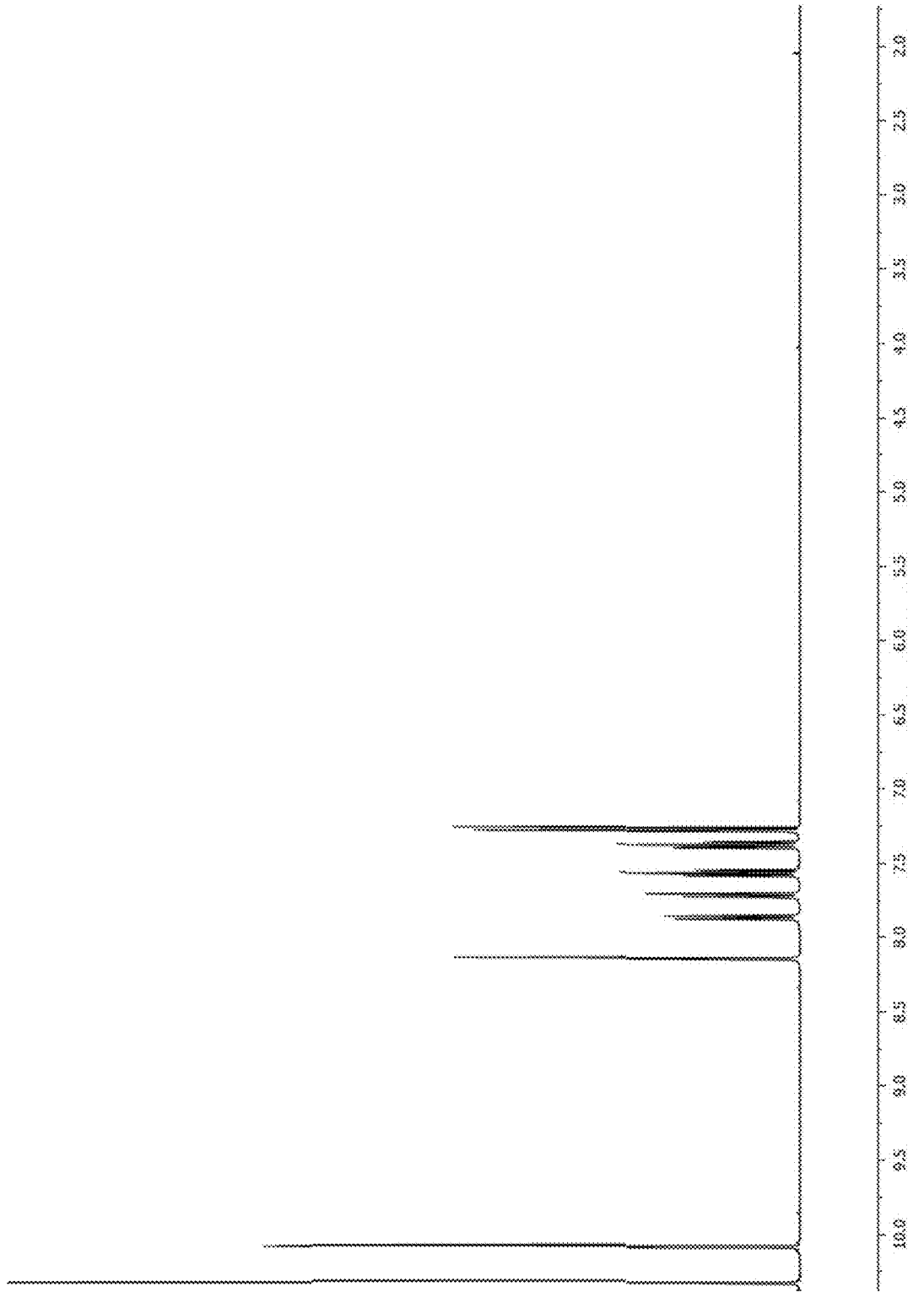
FIG. 45: is an example according to various embodiments, illustrating a characteristic $^1$HNMR (400 MHz, CDCl$_3$, 20° C.) spectra of compound S11 synthesized in the disclosed examples.

FIG. 45 shows ¹HNMR (400 MHz, CDCl₃, 25° C.) δ (ppm) 10.33 (s, 1H), 10.08 (d, J=0.6 Hz, 1H), 8.14 (s, 1H), 7.89-7.84 (m, 1H), 7.71 (d, J=8.4 Hz, 1H), 7.56 (d, J=16.5 Hz, 1H), 7.38 (d, J=16.3 Hz, 1H), 7.28 (s, 1H) spectra of compound S11.

Figure 46:
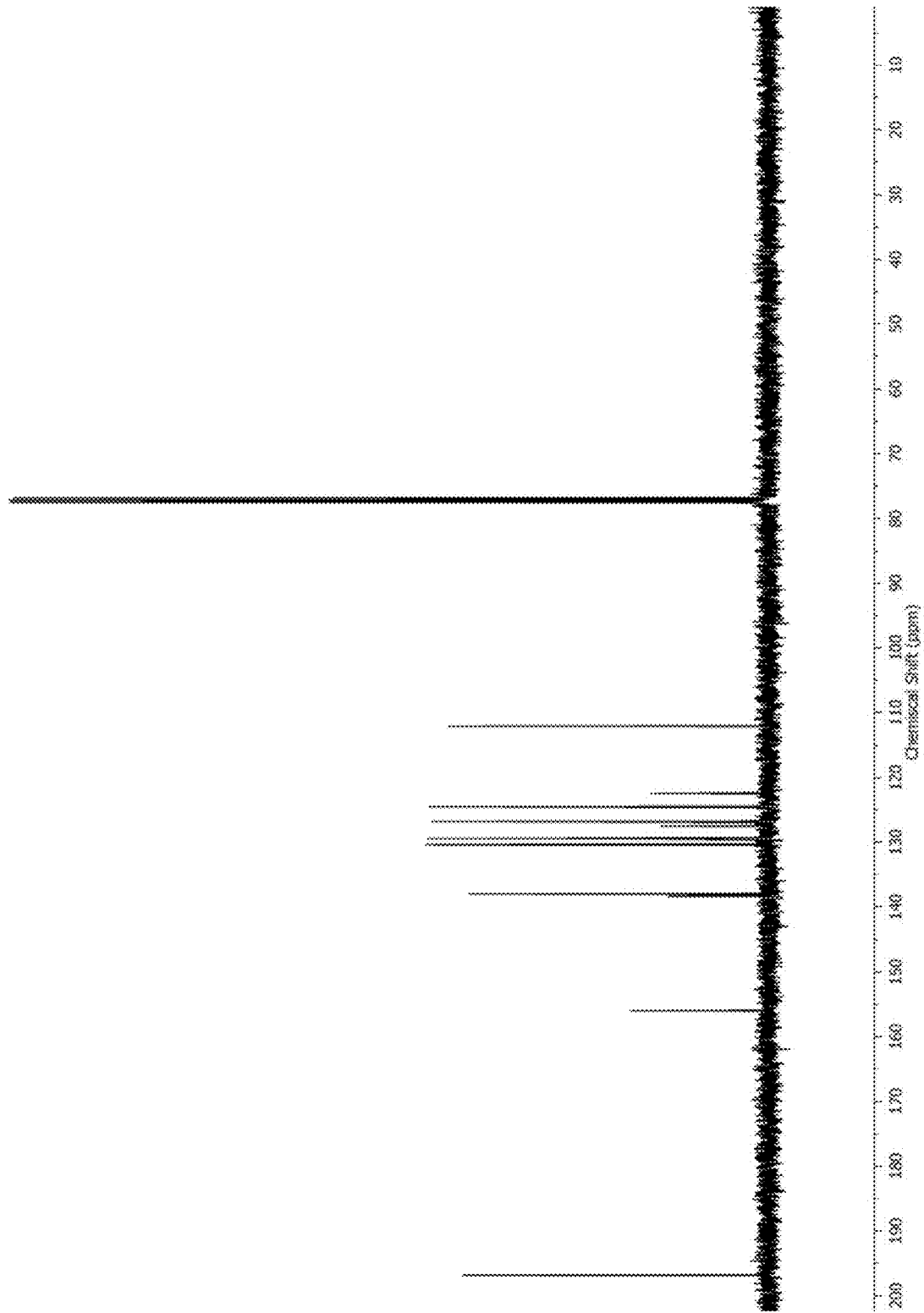
FIG. 46: is an example according to various embodiments, illustrating a characteristic $^{13}$CNMR (101 MHz, CDCl$_3$, 20° C.) spectra of compound S11 synthesized in the disclosed examples.

FIG. 46 shows ¹³C NMR (101 MHz, CDCl₃, 25° C.) δ (ppm) 196.80, 155.96, 138.33, 137.99, 130.41, 129.50, 127.54, 126.82, 124.55, 122.43, 112.07 spectra of compound S11.

Figure 48:
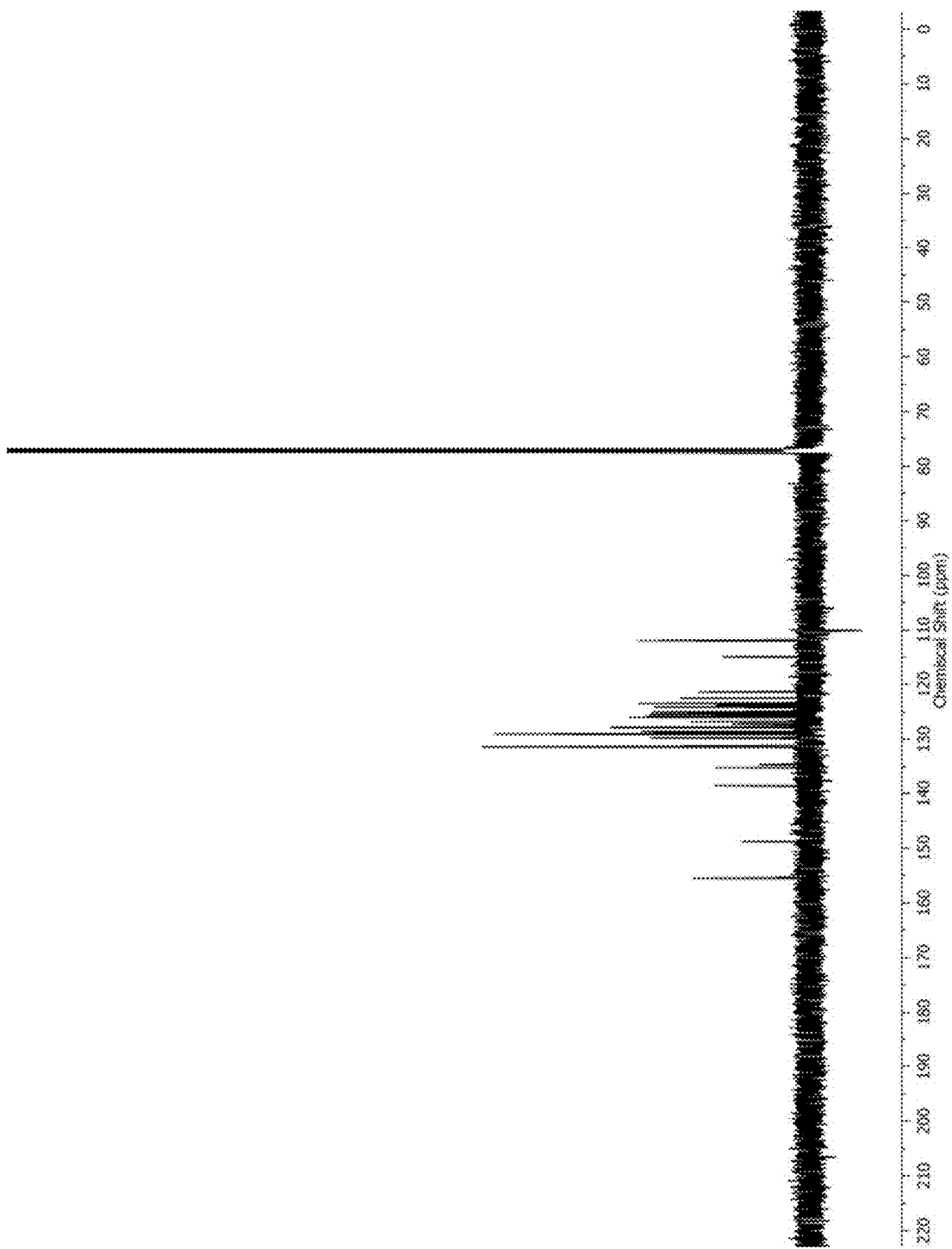
FIG. 48: is an example according to various embodiments, illustrating a characteristic $^{13}$CNMR (101 MHz, CDCl$_3$, 20° C.) spectra of compound S12 synthesized in the disclosed examples.

FIG. 48 shows ¹³C NMR (101 MHz, CDCl₃) δ (ppm) 155.51, 148.75, 138.56, 135.23, 134.63, 131.38, 131.23, 129.72, 129.05, 128.86, 128.59, 127.86, 127.84, 127.78, 127.22, 126.94, 126.80, 126.80, 125.98, 125.78, 125.42, 125.04, 124.11, 123.81, 123.46, 122.46, 121.39, 114.94, 111.96 spectra for compound S12.

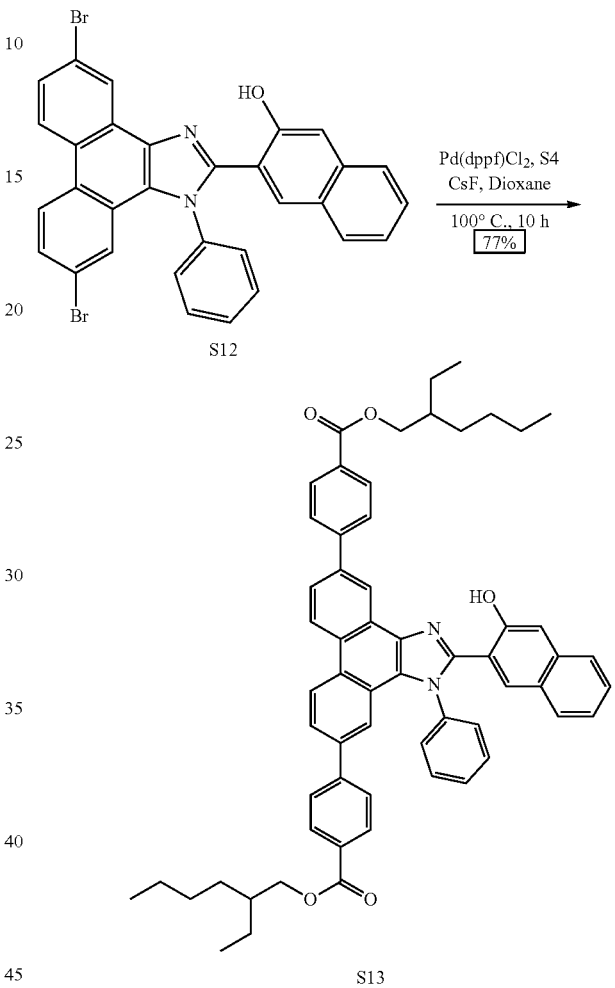

S12

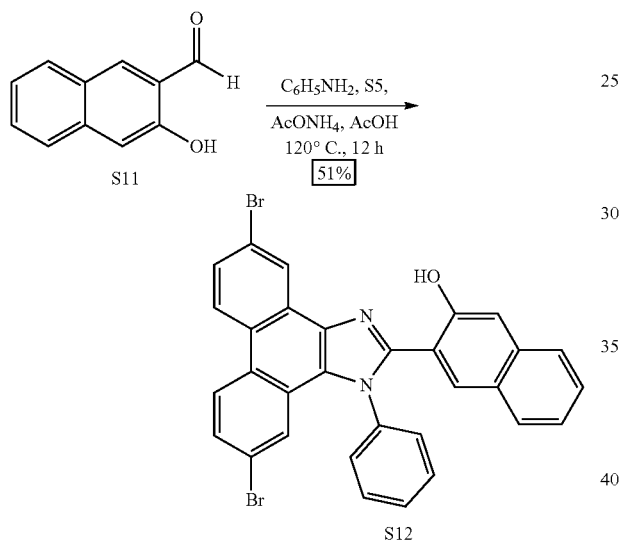

S11

S12

2-(5,10-dibromo-1-phenyl-1H-phenanthro[9, 10-d]imidazol-2-yl)-naphthol (S12): Adapted from [3]. S5 (1.00 g, 2.73 mmol, 1.0 eq) was added to a 50 mL schlenk flask with ammonium acetate (1.05 g, 13.66 mmol, 5.0 eq). The system was purged with N₂ gas three times. Then acetic acid (13.7 mL) was added to the vessel followed by aniline (0.50 mL, 5.45 mmol, 2.0 eq) and S11 (0.47 g, 2.73 mmol, 1.0 eq). The reaction vessel was then heated to reflux for 12 h. Upon cooling to room temperature the reaction was quenched with water and the resulting precipitate was collected via vacuum filtration and rinsed with water. The brown solid was dissolved in CH₂Cl₂ and rinsed once with brine, then passed through a silica plug with hot CH₂Cl₂. The CH₂Cl₂ was then removed in a rotary evaporator and the residue was recrystallized from ethyl acetate resulting in a light cocoa colored solid. Yield 0.830 g (51%).

Figure 47:
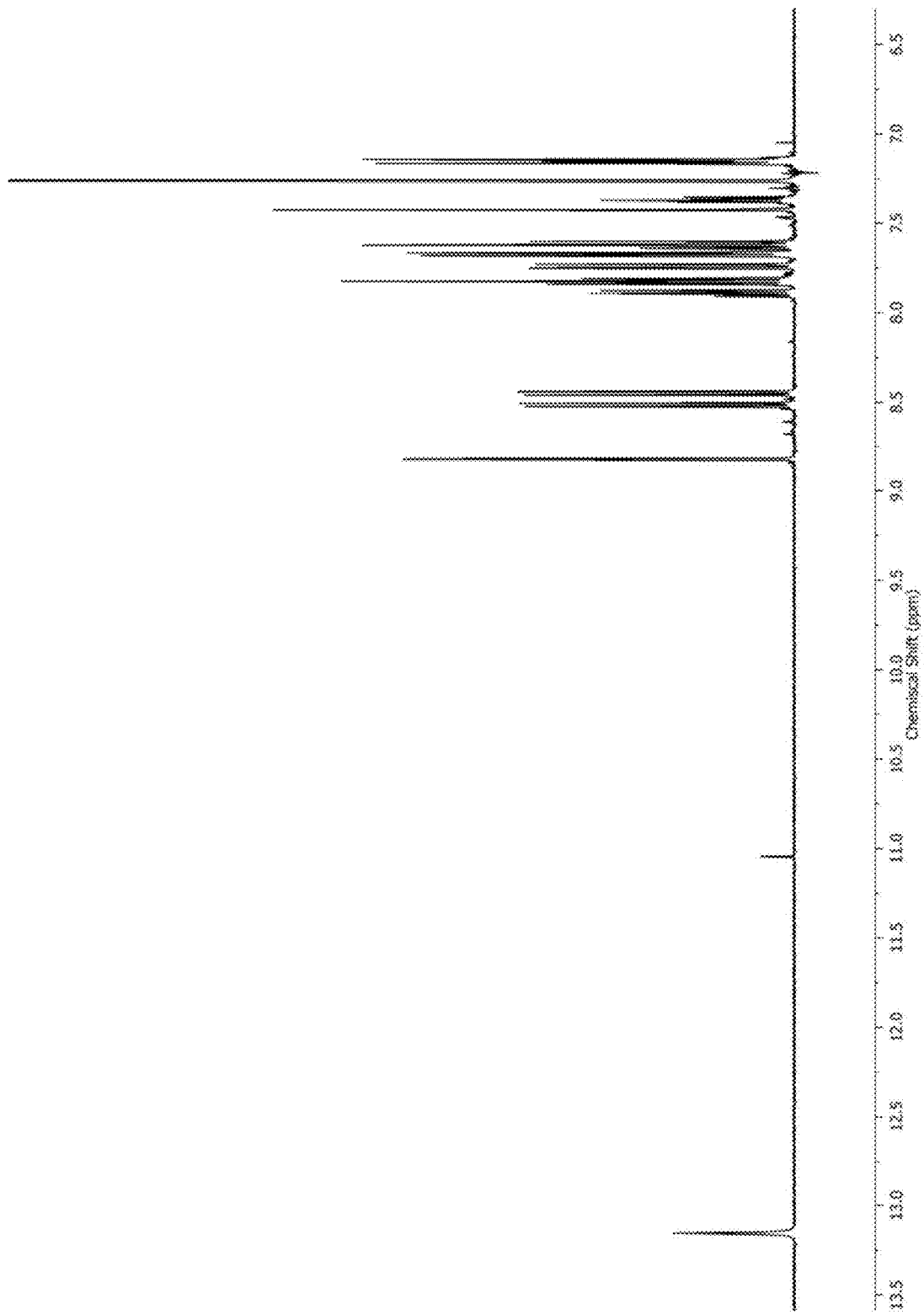
FIG. 47: is an example according to various embodiments, illustrating a characteristic $^1$HNMR (400 MHz, CDCl$_3$, 20° C. spectra of compound S12 synthesized in the disclosed examples.

FIG. 47 shows ¹HNMR (400 MHz, CDCl₃, 25° C.) δ (ppm) 13.15 (s, 1H), 8.82 (d, J=2.1 Hz, 1H), 8.52 (d, J=9.0 Hz, 1H), 8.45 (d, J=8.9 Hz, 1H), 7.91-7.87 (m, 1H), 7.83 (t, J=7.6 Hz, 2H), 7.74 (dd, J=8.8, 2.2 Hz, 1H), 7.69-7.66 (m, 2H), 7.64-7.59 (m, 2H), 7.43 (s, 1H), 7.37 (d, J=16.3 Hz, 1H), 7.26 (s, 1H), 7.15 (d, J=11.7 Hz, 3H) spectra for compound S12.

S13

2-(5,10-bis-(2-ethylhexyl-4-benzoate)-1-phenyl-1H-phenanthro[9, 10-d]imidazol-2-yl)-naphthol (S13): S12 (1.10 g, 1.85 mmol, 1.0 eq) was added to 50 mL schlenk flask followed by: S4 (1.49 g, 5.37 mmol, 2.9 eq), CsF (1.69 g, 11.11 mmol, 6.0 eq), and Pd(dppf)Cl₂ (0.098 g, 0.12 mmol, 0.065 eq). The vessel was purged with N₂ three times and anhydrous dioxane (24.7 mL) was added. The system was heated to reflux for 10 h and then cooled to room temperature. The reaction was quenched with water and extracted with CH₂Cl₂. The combined organic layers were rinsed once with water and brine, then dried over Na₂SO₄. The CH₂Cl₂ was removed using a rotary evaporator and the crude was subjected to column chromatography (SiO₂, 0-40% v/v CH₂Cl₂/hexanes), where the column was pretreated with 3% v/v TEA in hexanes, to yield a yellow wax. Yield 1.29 g (77.2%).

Figure 49:
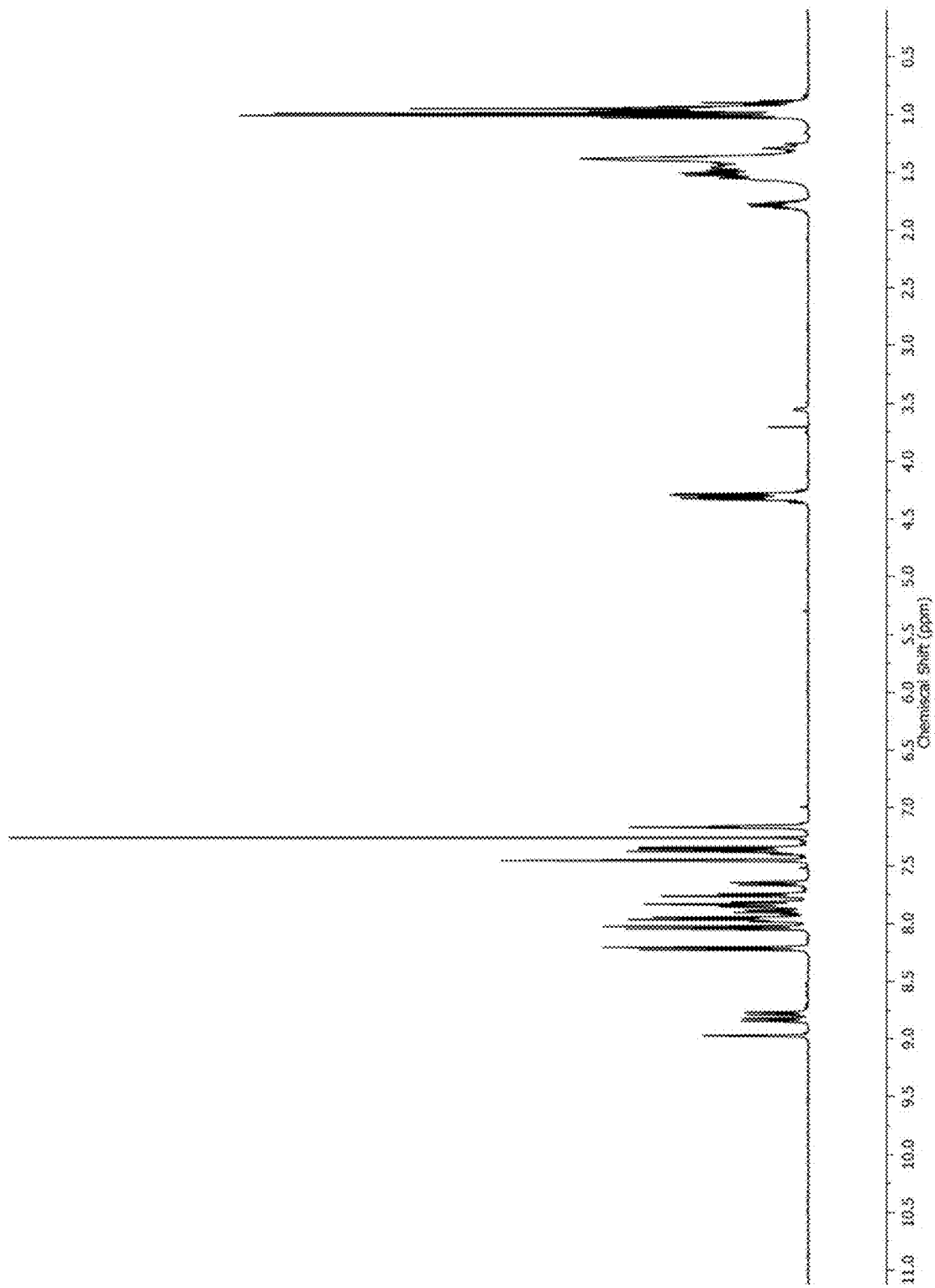
FIG. 49: is an example according to various embodiments, illustrating a characteristic $^1$HNMR (400 MHz, CDCl$_3$, 20° C.) spectra of compound S13 synthesized in the disclosed examples.

FIG. 49 shows ¹HNMR (400 MHz, CDCl₃, 25° C.) δ (ppm) 8.79 (d, J=2.0 Hz, 1H), 8.63 (d, J=9.0 Hz, 1H), 8.56 (d, J=8.9 Hz, 1H), 8.15 (d, J=8.5 Hz, 2H), 7.98 (d, J=8.5 Hz, 2H), 7.86-7.78 (m, 4H), 7.72 (d, J=28.6 Hz, 3H), 7.59 (d, J=8.5 Hz, 3H), 7.34 (d, J=26.3 Hz, 3H), 7.26 (s, 1H), 7.24 (s, 1H), 7.19 (s, 1H), 7.06 (s, 2H), 4.34-4.26 (m, 4H), 1.79 (m, 2H), 1.36 (s, 16H), 1.05-0.97 (m, 12H) spectra of compound S13.

Figure 50:
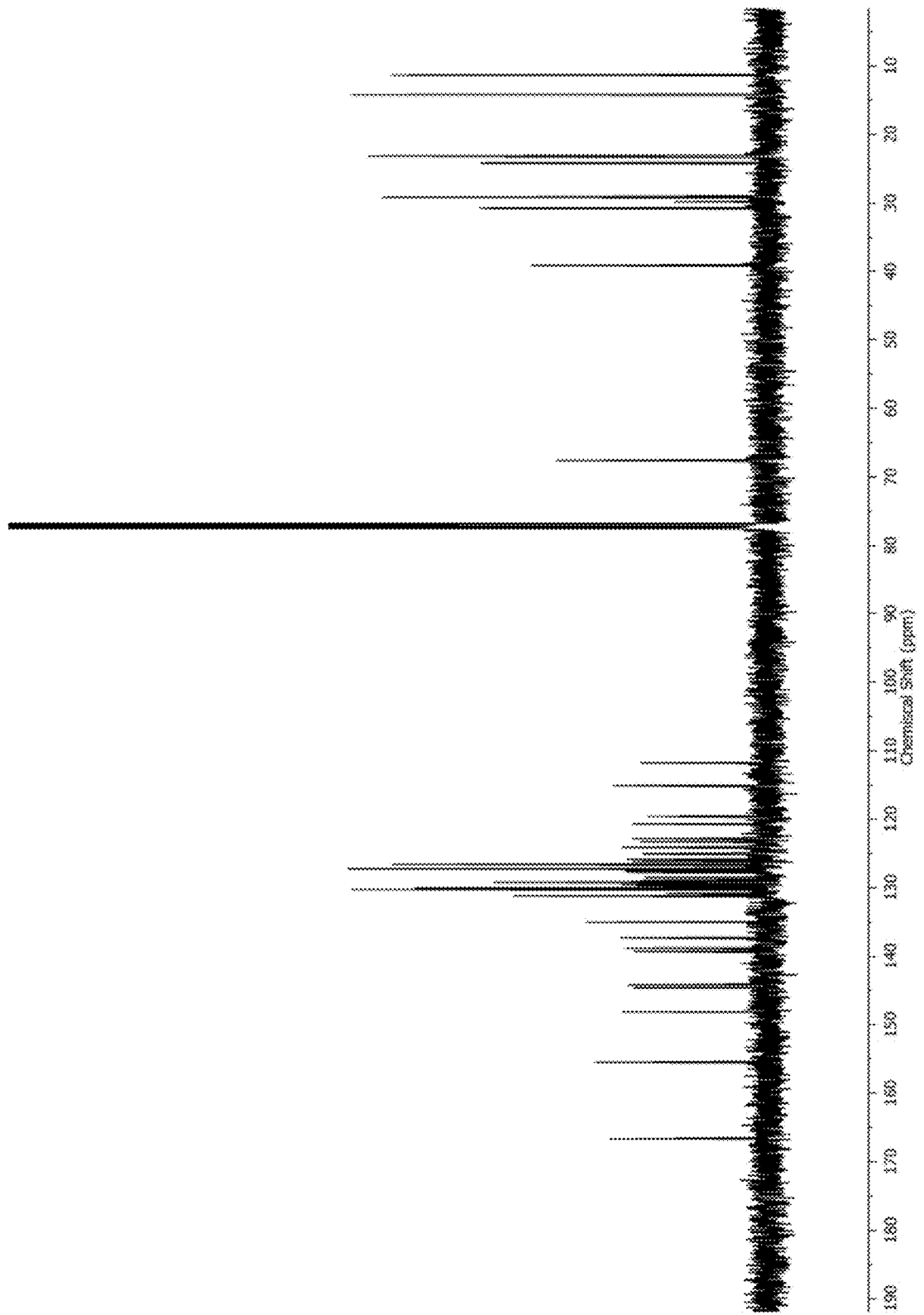
FIG. 50: is an example according to various embodiments, illustrating a characteristic $^{13}$CNMR (101 MHz, CDCl$_3$, 20° C.) spectra of compound S13 synthesized in the disclosed examples.

FIG. 50 shows $^{13}$C NMR (101 MHz, CDCl$_3$) δ (ppm) 166.69, 166.59, 155.53, 148.10, 144.59, 144.18, 139.30, 138.81, 137.30, 135.08, 135.06, 131.19, 130.82, 130.27, 130.08, 129.73, 129.58, 129.24, 128.91, 128.52, 127.78, 127.70, 127.58, 127.53, 127.25, 126.76, 126.60, 126.20, 125.87, 125.11, 125.00, 124.13, 124.10, 123.32, 122.84, 120.70, 119.62, 115.03, 111.75, 67.65, 67.57, 39.13, 39.07, 30.81, 30.75, 29.19, 29.16, 24.23, 24.17, 23.19, 23.16, 14.27, 14.24, 11.32, 11.26 spectra of compound S13.

Figure 15:
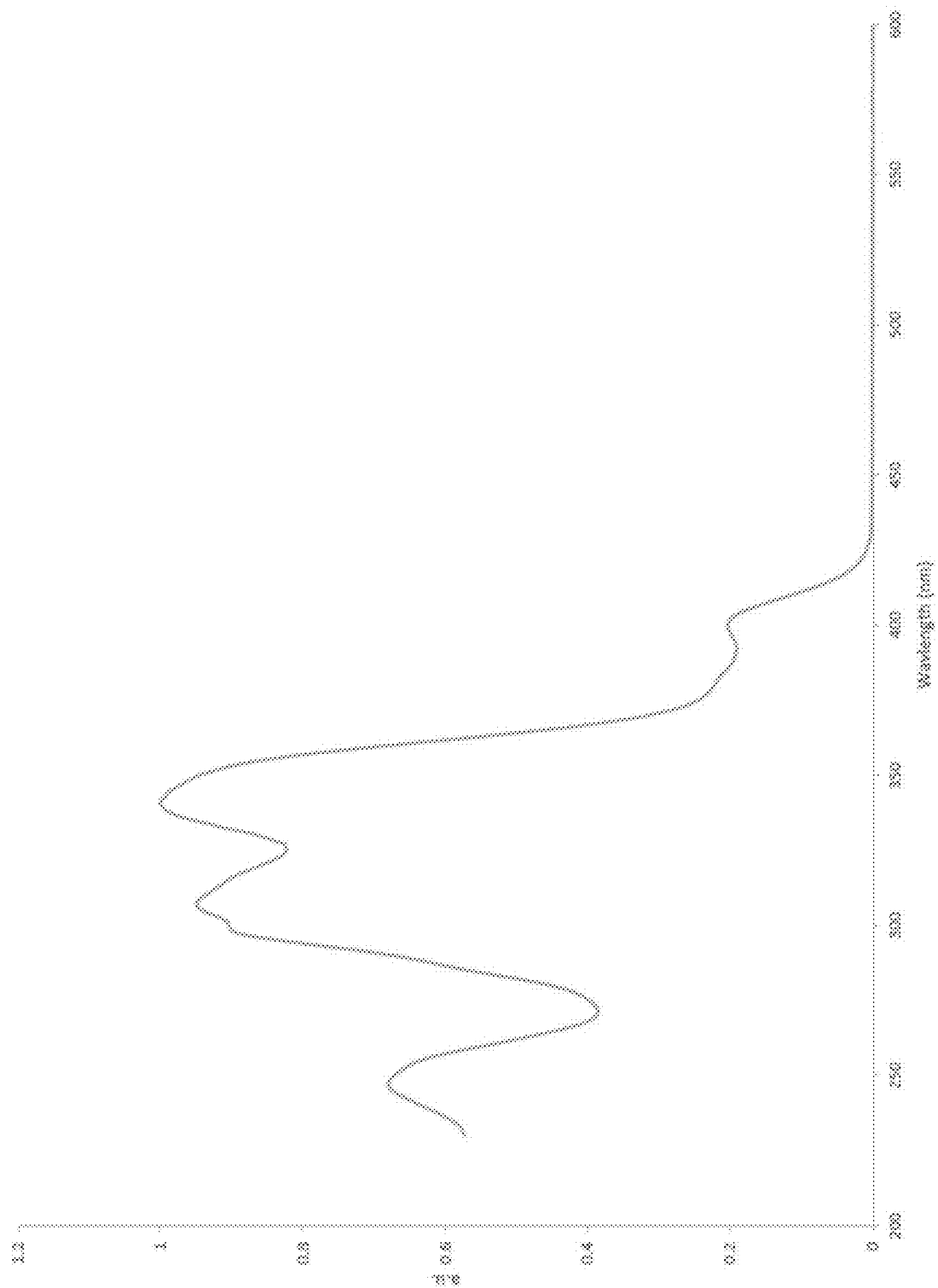
FIG. 15: is an example according to various embodiments illustrating a solid-state absorbance spectrum of compound S13 (as synthesized in the Examples) in DCE.

FIG. 15 illustrates a solid-state absorbance spectrum of compound S13 in DCE.

Figure 18:
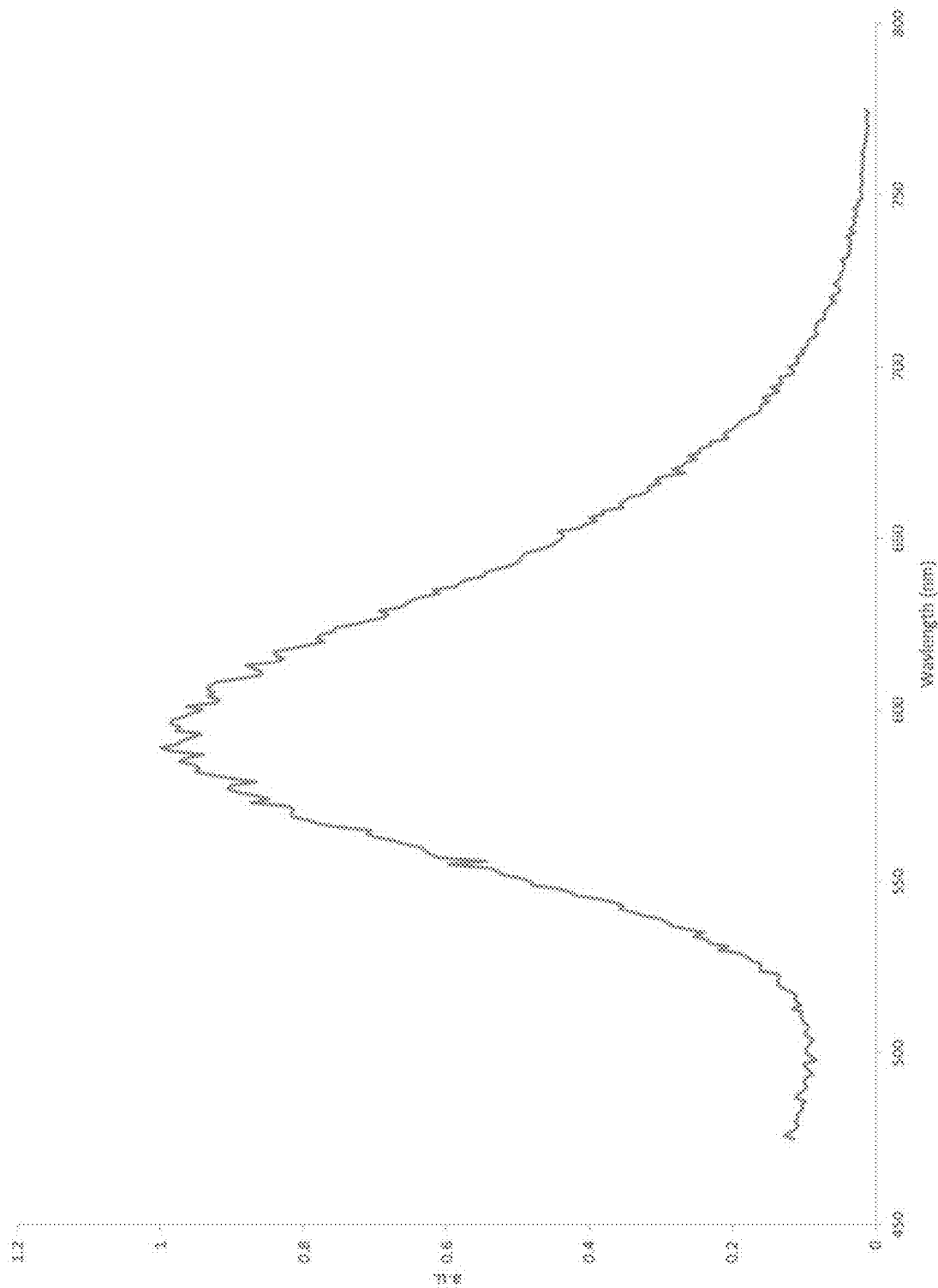
FIG. 18: is an example according to various embodiments illustrating a solid-state fluorescence spectrum of compound S13 (as synthesized in the Examples) in DCE.

FIG. 18 illustrates a solid-state fluorescence spectrum of compound S13 in DCE.

2-(5,10-bis-(4-benzoic acid)-1-phenyl-1H-phenanthro[9,10-d]imidazol-2-yl)-phenol (O linker): Dissolved S13 (1.29 g, 1.43 mmol, 1.0 eq) in THF (95.3 mL). 5M KOH in methanol (14.3 mL, 71.5 mmol, 50 eq) was added to the THF solution and then heated to reflux for 4 h. The solvent was removed in a rotary evaporator and the residue was dissolved in water. The solution was quenched using 3M H$_2$SO$_4$ and the resulting yellow solid was collected via vacuum filtration, and rinsed with water and cold methanol. Yield 0.95 g (98%).

Figure 51:
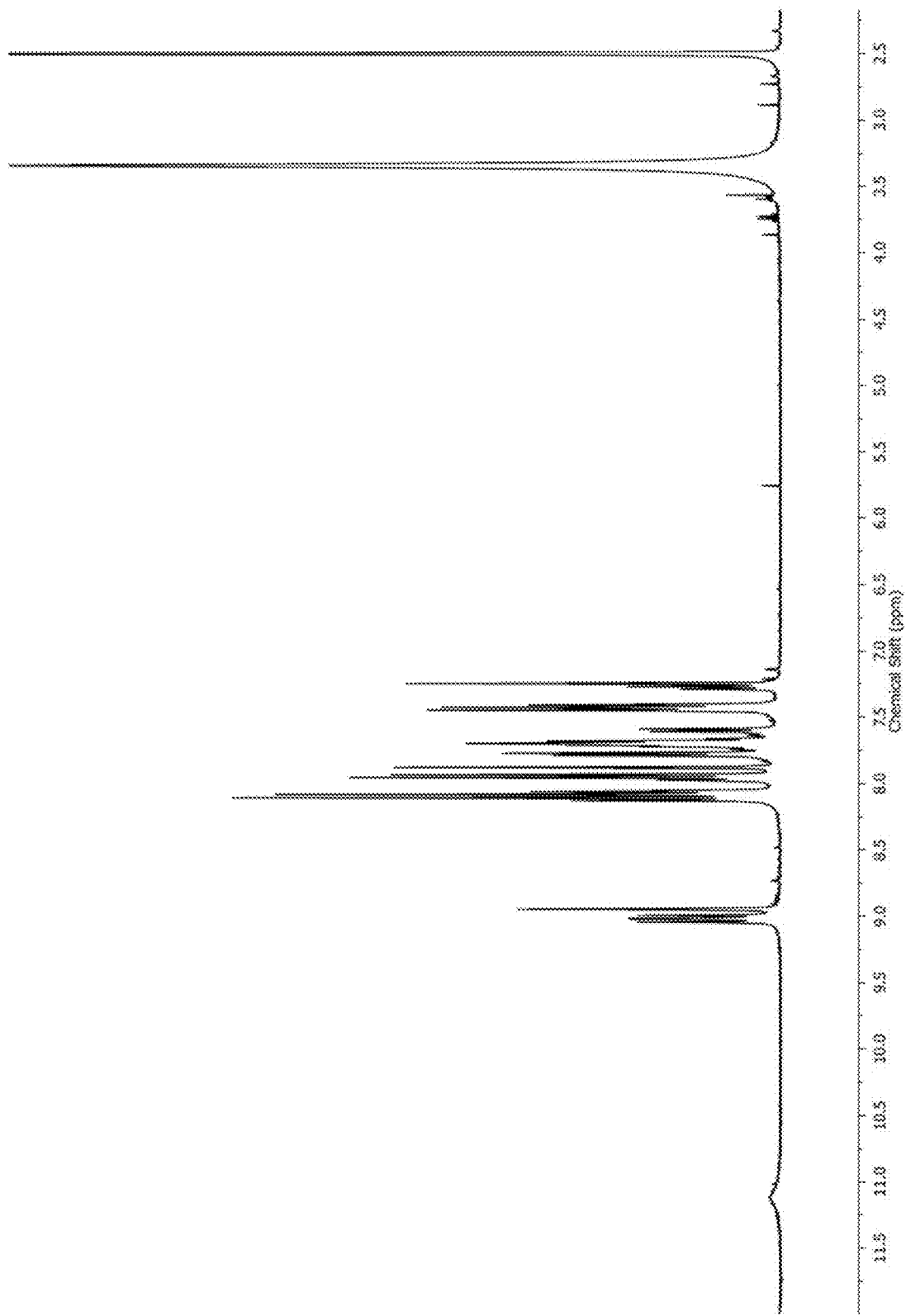
FIG. 51: is an example according to various embodiments, illustrating a characteristic $^1$HNMR (400 MHz, DMSO-d$_6$, 20° C.) spectra of an orange linker compound synthesized in the disclosed examples.

FIG. 51 shows $^1$HNMR (400 MHz, DMSO-d6) δ (ppm) 9.10 (dd, J=11.0, 8.9 Hz, 2H), 8.99 (d, J=2.1 Hz, 1H), 8.13 (m, 5H), 8.03 (dd, J=8.7, 1.9 Hz, 1H), 7.98-7.92 (m, 3H), 7.84-7.79 (m, 2H), 7.76-7.67 (m, 4H), 7.64 (d, J=8.2 Hz, 1H), 7.51-7.42 (m, 4H), 7.32-7.21 (m, 2H) spectra of the orange linker.

Figure 52:
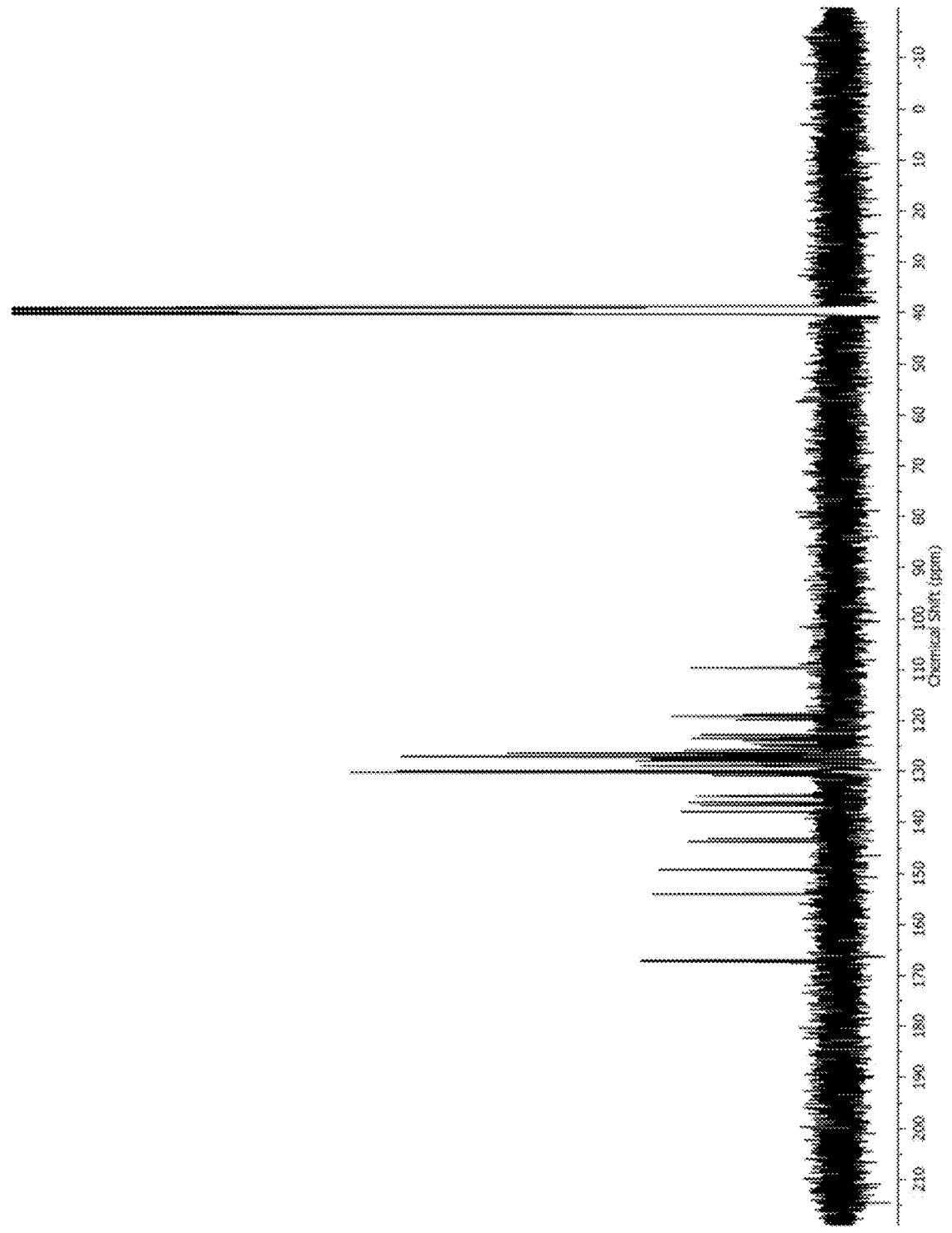
FIG. 52: is an example according to various embodiments, illustrating a characteristic $^{13}$CNMR (101 MHz, DMSO-d$_6$, 20° C.) spectra of an orange linker compound synthesized in the disclosed examples.

FIG. 52 shows $^{13}$C NMR (101 MHz, DMSO-d$_6$, 25° C.) δ (ppm) 167.15, 166.96, 154.05, 154.03, 149.27, 143.74, 143.18, 137.97, 137.92, 136.61, 136.05, 134.84, 130.83, 130.23, 130.17, 129.93, 129.88, 128.94, 127.96, 127.64, 127.33, 127.17, 127.09, 126.90, 126.61, 126.41, 125.78, 125.63, 125.06, 125.04, 124.61, 123.86, 123.42, 122.73, 119.77, 119.14, 118.74, 109.60 spectra of the orange linker.

Example 4

A purpose of this example is to illustrate a general synthetic scheme of green linker (also referenced in FIG. 2E).

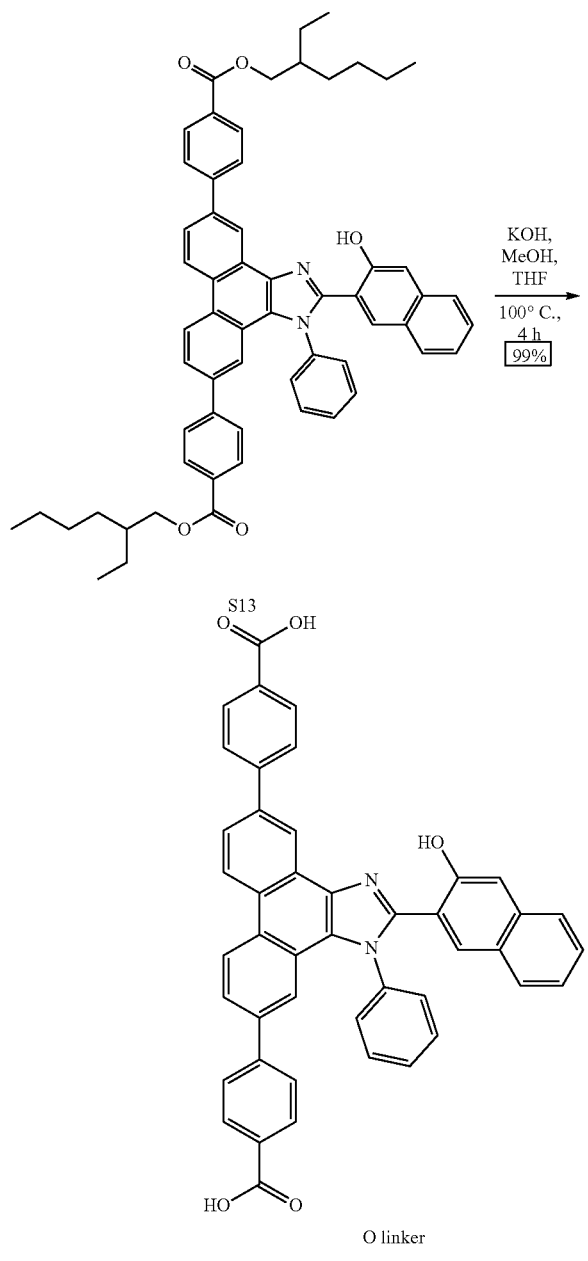

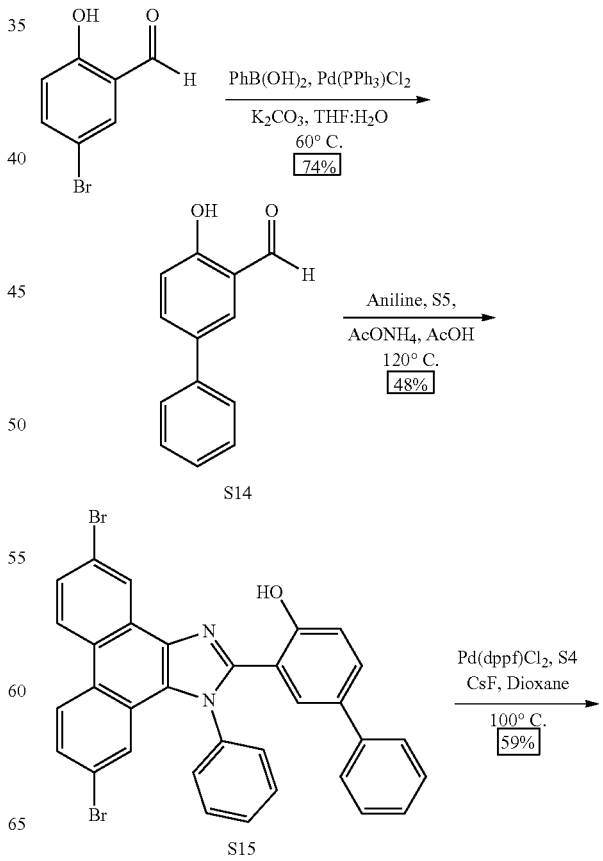

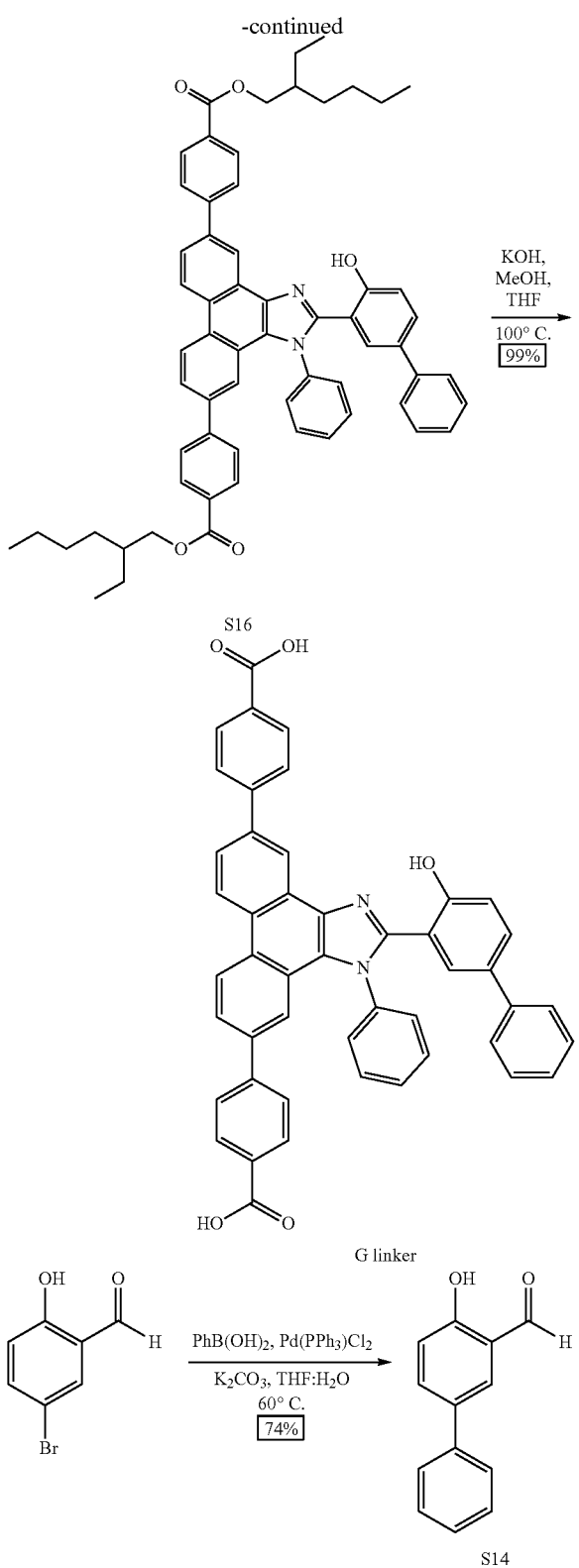

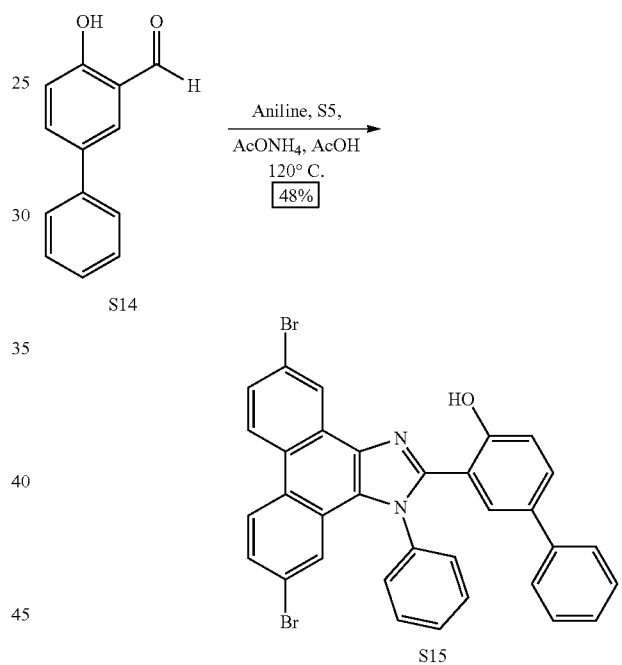

eq). The system was purged with N₂ gas three times. Meanwhile a 1:1 (v:v) mixture of water and THF was degassed by bubbling with nitrogen gas. Then THF:Water (50 mL) was added to the vessel followed. The reaction vessel was then heated to 60° C. for 12 h. The reaction was quenched with water and extracted with CH₂Cl₂. The combined organic layers were rinsed once brine and then dried over Na₂SO₄. The CH₂Cl₂ was removed using a rotary evaporator and the crude was subjected to column chromatography (SiO₂, 0-10% v/v EtOAc/hexanes) to yield a yellow solid. Yield 1.09 g (74.1%).

Figure 53:
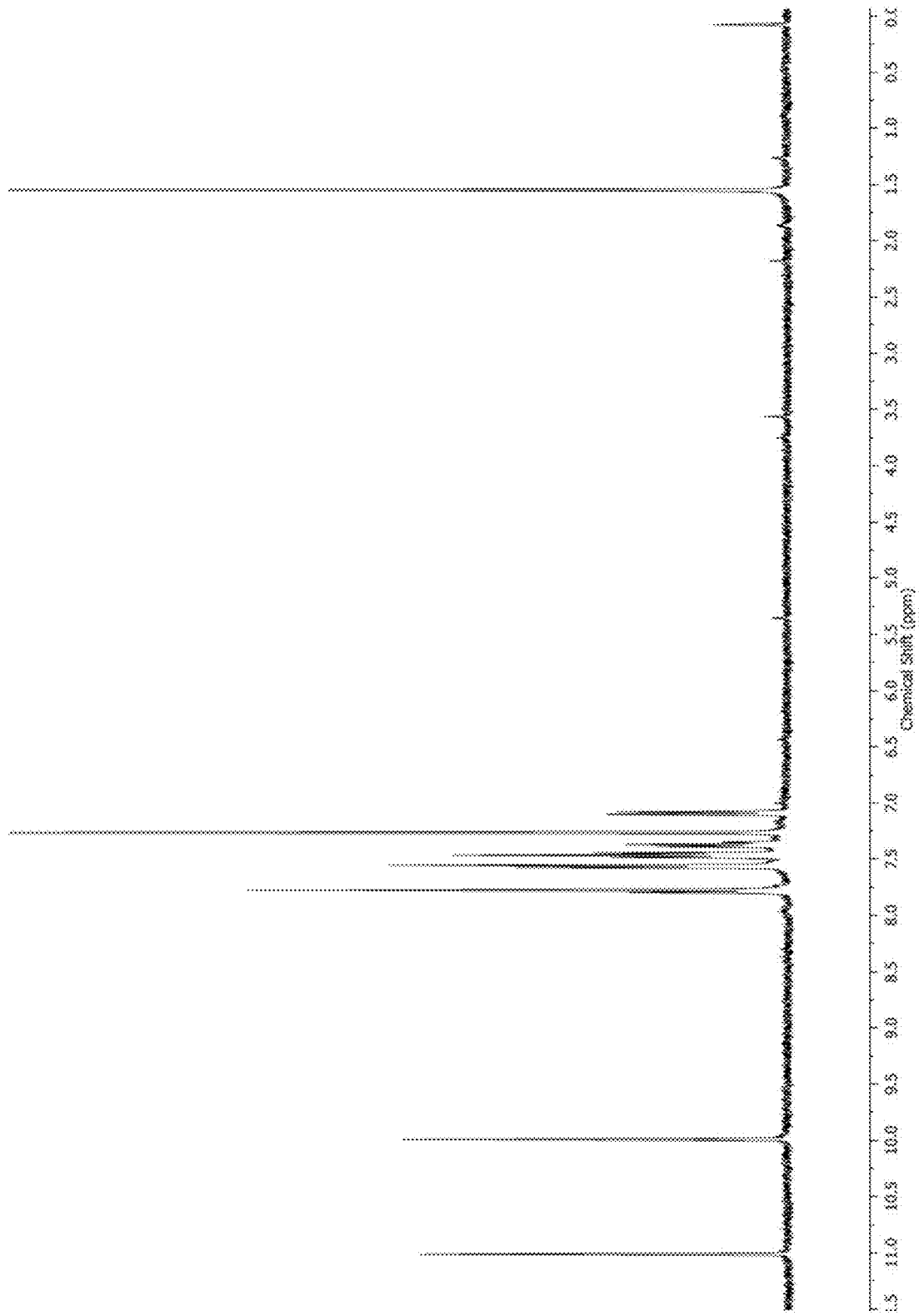
FIG. 53: is an example according to various embodiments, illustrating a characteristic $^1$HNMR (400 MHz, CDCl$_3$, 20° C.) spectra of compound S14 synthesized in the disclosed examples.

FIG. 53 shows ¹HNMR (400 MHz, CDCl₃, 25° C.) δ (ppm) 11.01 (s, 1H), 9.98 (d, J=0.6 Hz, 1H), 7.79-7.75 (m, 2H), 7.57-7.54 (m, 2H), 7.49-7.44 (m, 2H), 7.39-7.34 (m, 1H), 7.11-7.06 (m, 1H) spectra of compound S14.

Figure 54:
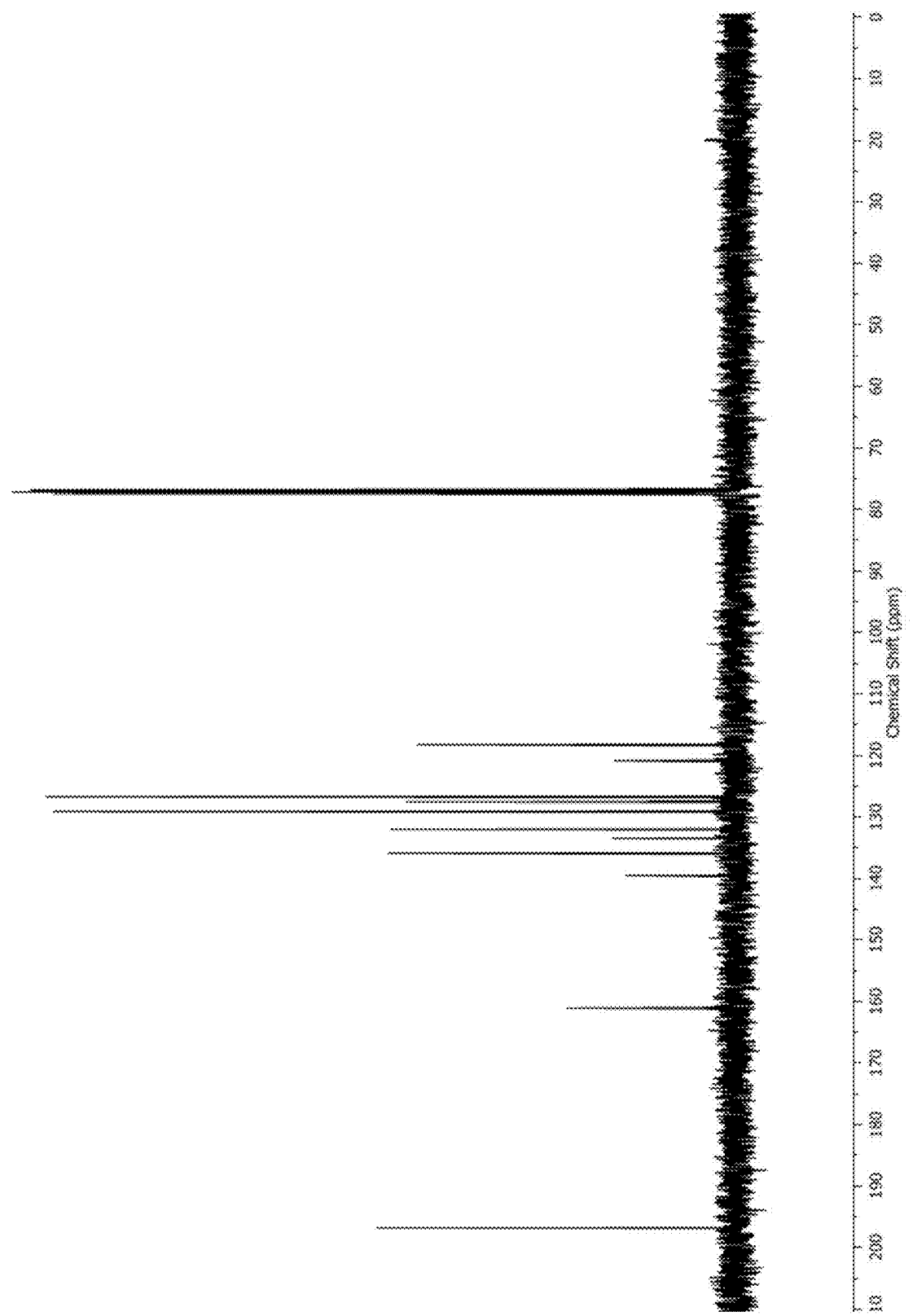
FIG. 54: is an example according to various embodiments, illustrating a characteristic $^{13}$CNMR (101 MHz, CDCl, 20° C.) spectra of compound S14 synthesized in the disclosed examples.

FIG. 54 shows ¹³C NMR (101 MHz, CDCl₃) δ (ppm) 196.79, 161.11, 139.47, 135.88, 133.46, 132.00, 129.12, 127.53, 126.73, 120.85, 118.27, 77.16 spectra of compound S14.

4-hydroxy-[1,1'-Biphenyl]-3-carboxaldehyde (S14): Adapted from [7]. 5-bromo salicylaldehyde (1.50 g, 7.46 mmol, 1.0 eq) was added to a 100 mL schlenk flask with phenyl boronic acid (1.09 g, 8.95 mmol, 1.2 eq), K₂CO₃ (3.09 g, 22.39 mmol, 3.0 eq), and Palladium (II) bis-(triphenylphosphine) dichloride (0.262 g, 0.37 mmol, 0.05

3-(1-phenyl-1H-phenanthro[9,10-d]imidazol-2-yl)-[1,1'-Biphenyl]-4-ol (S15): Adapted from [3]. S5 (1.93 g, 5.27 mmol, 1.0 eq) was added to a 100 mL 2 neck flask with S14 (1.05 g, 5.27 mmol, 1.0 eq). The system was purged with N₂ gas three times. Then acetic acid (13.7 mL) was added to the vessel followed by aniline (0.50 mL, 5.45 mmol, 2.0 eq) and ammonium acetate (2.03 g, 26.37 mmol, 5.0 eq). The reaction vessel was then heated to reflux for 12 h. Upon cooling to room temperature the reaction was quenched with water and the resulting precipitate was collected via vacuum filtration and rinsed with water. The green solid was dissolved in CH₂Cl₂ and rinsed once with brine, then passed through a silica plug with hot CH₂Cl₂. The CH₂Cl₂ was then removed in a rotary evaporator and the residue was triturated from acetone, with water resulting in a light yellow solid. Yield 1.57 g (48%).

Figure 55:
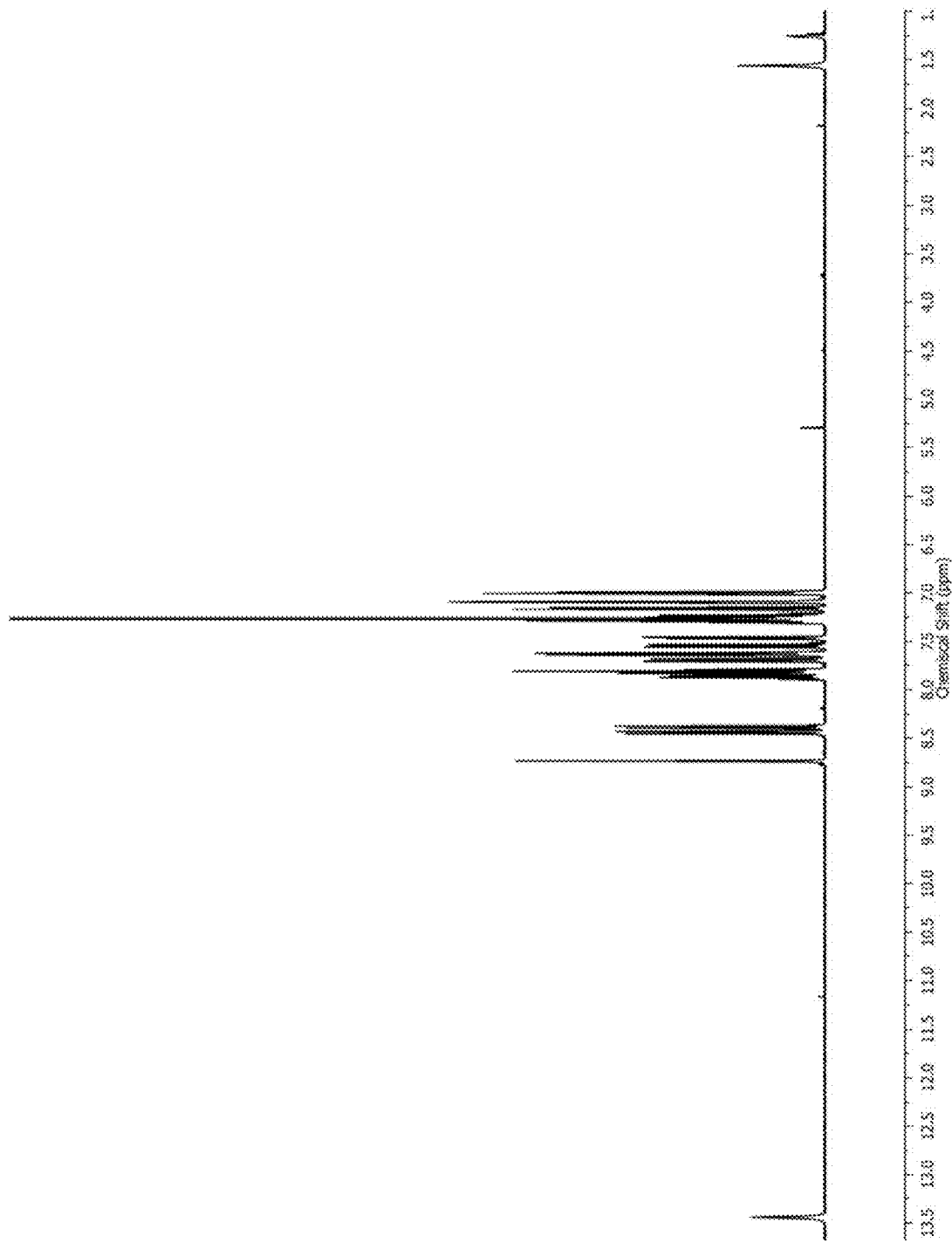
FIG. 55: is an example according to various embodiments, illustrating a characteristic $^1$HNMR (400 MHz, CDCl$_3$, 20° C.) spectra of compound S15 synthesized in the disclosed examples.

FIG. 55 shows ¹HNMR (400 MHz, CDCl₃, 25° C.) δ (ppm) 8.80 (d, J=2.1 Hz, 1H), 8.50 (d, J=9.0 Hz, 1H), 8.45 (d, J=8.9 Hz, 1H), 7.90-7.79 (m, 3H), 7.74 (dd, J=8.9, 2.2

Hz, 1H), 7.69-7.65 (m, 2H), 7.59 (dd, J=8.9, 2.0 Hz, 1H), 7.50 (dd, J=8.6, 2.3 Hz, 1H), 7.32-7.27 (m, 2H), 7.25-7.21 (m, 1H), 7.19 (dd, J=8.5, 0.4 Hz, 1H), 7.13 (ddd, J=6.2, 2.2, 0.4 Hz, 2H), 7.06-6.98 (m, 2H) spectra of compound S15.

Figure 56:
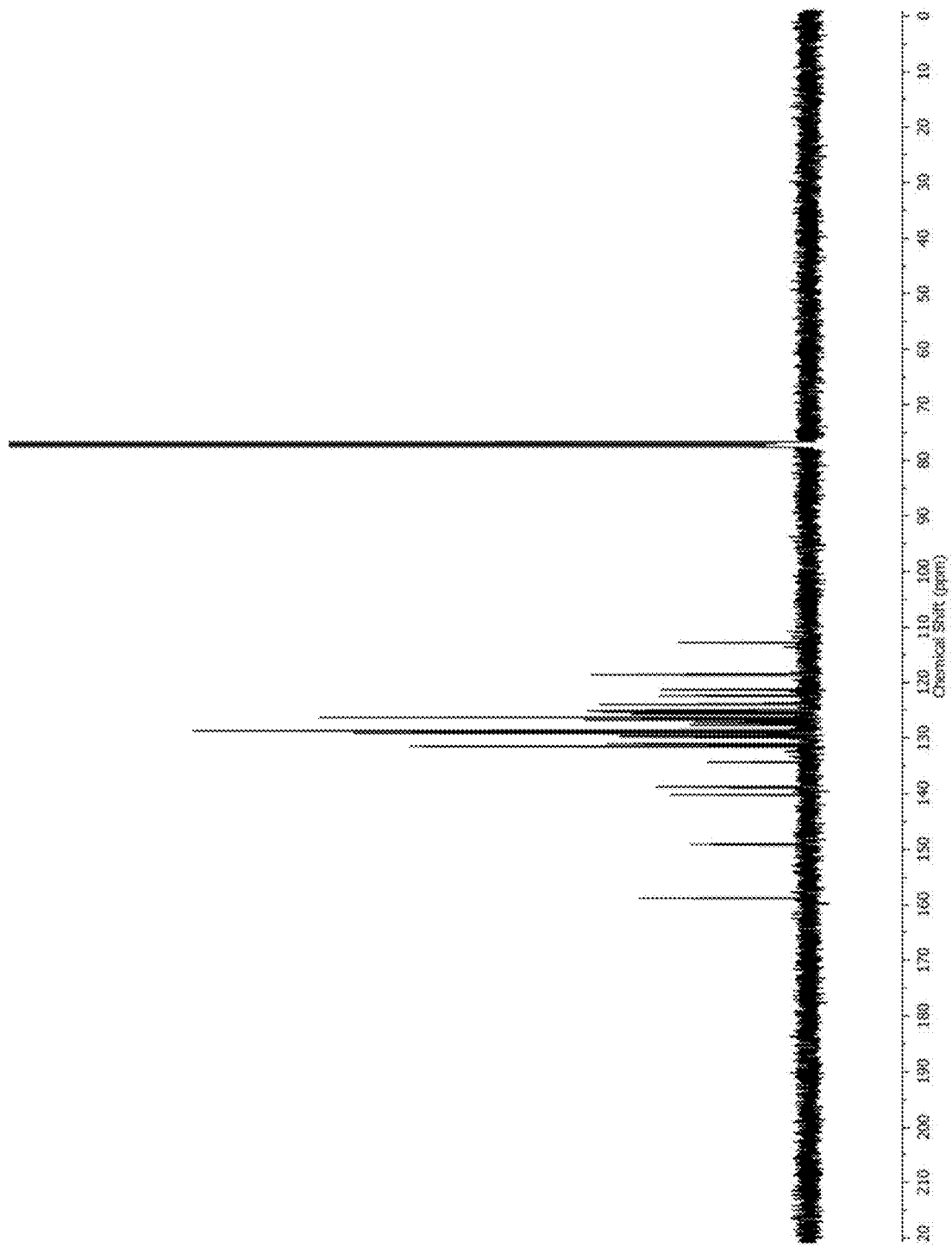
FIG. 56: is an example according to various embodiments, illustrating a characteristic $^{13}$CNMR (101 MHz, CDCl, 20° C.) spectra of compound S15 synthesized in the disclosed examples.

FIG. 56 shows $^{13}$C NMR (101 MHz, CDCl$_3$) δ (ppm) 158.83, 149.13, 140.16, 138.80, 134.32, 131.45, 131.03, 130.99, 129.76, 129.60, 129.07, 128.67, 127.65, 127.12, 126.95, 126.73, 126.71, 126.62, 126.25, 125.72, 125.36, 125.12, 124.99, 123.95, 123.78, 122.39, 121.35, 118.64, 112.81 spectra of compound S15.

3-(5,10-bis-(2-ethylhexyl-4-benzoate)-1-phenyl-1H-phenanthro[9,10-d]imidazol-2-yl)-[1,1'-Biphenyl]-4-ol (S16): S15 (0.04 g, 0.064 mmol, 1.0 eq) was added to 15 mL two neck flask followed by: S4 (0.052 g, 0.184 mmol, 2.9 eq), CsF (0.029 g, 0.193 mmol, 3.0 eq), and Pd(dppf)Cl$_2$ (0.002 g, 0.003 mmol, 0.04 eq). The vessel was purged with N$_2$ three times and anhydrous dioxane (1.29 mL) was added. The system was heated to reflux for 18 h and then cooled to room temperature. The reaction was quenched with water and extracted with CH$_2$Cl$_2$. The combined organic layers were rinsed once with water and brine, then dried over Na$_2$SO$_4$. The CH$_2$Cl$_2$ was removed using a rotary evaporator and the crude was subjected to column chromatography (SiO$_2$, 0-35% v/v CH$_2$Cl$_2$/hexanes), where the column was pretreated with 3% v/v TEA in hexanes, to yield a yellow wax. Yield 35.4 mg (59.0%).

Figure 57:
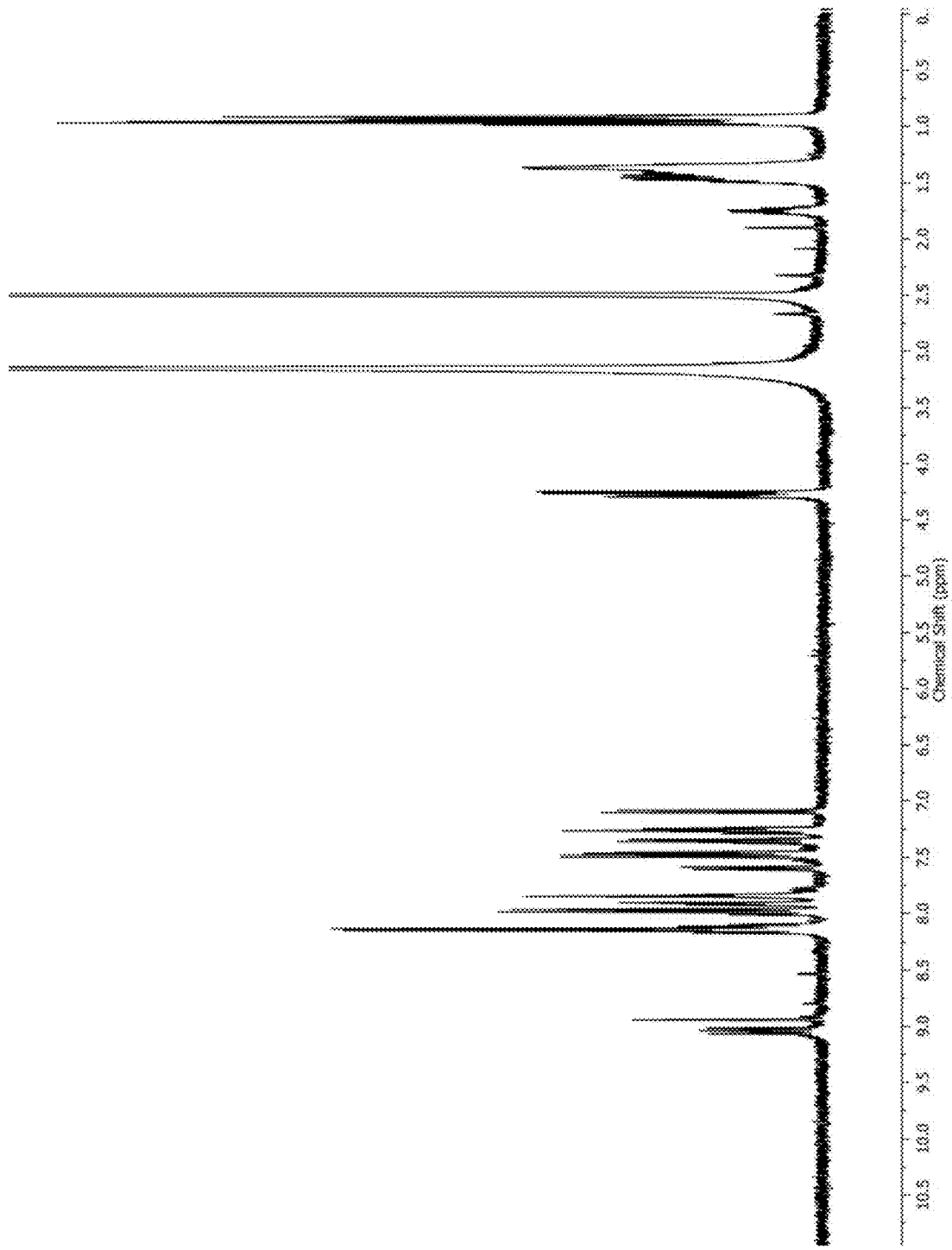
FIG. 57: is an example according to various embodiments, illustrating a characteristic $^1$HNMR (400 MHz, DMSO-d$_6$, 20° C.) spectra of compound S16 synthesized in the disclosed examples.

FIG. 57 shows $^1$HNMR (400 MHz, CDCl$_3$, 25° C.) δ (ppm) 8.97 (d, J=2.0 Hz, 1H), 8.89-8.75 (m, 2H), 8.25-8.20 (m, 2H), 8.09-7.94 (m, 5H), 7.94-7.75 (m, 6H), 7.52 (dd, J=8.5, 2.3 Hz, 1H), 7.45 (d, J=1.9 Hz, 1H), 7.37 (d, J=8.4 Hz, 2H), 7.33-7.28 (m, 2H), 7.25-7.20 (m, 2H), 7.11-7.01 (m, 2H), 4.30 (ddd, J=12.1, 5.7, 2.6 Hz, 4H), 1.83-1.73 (m, 2H), 1.53-1.31 (m, 16H), 1.05-0.91 (m, 12H) spectra of compound S16.

Figure 58:
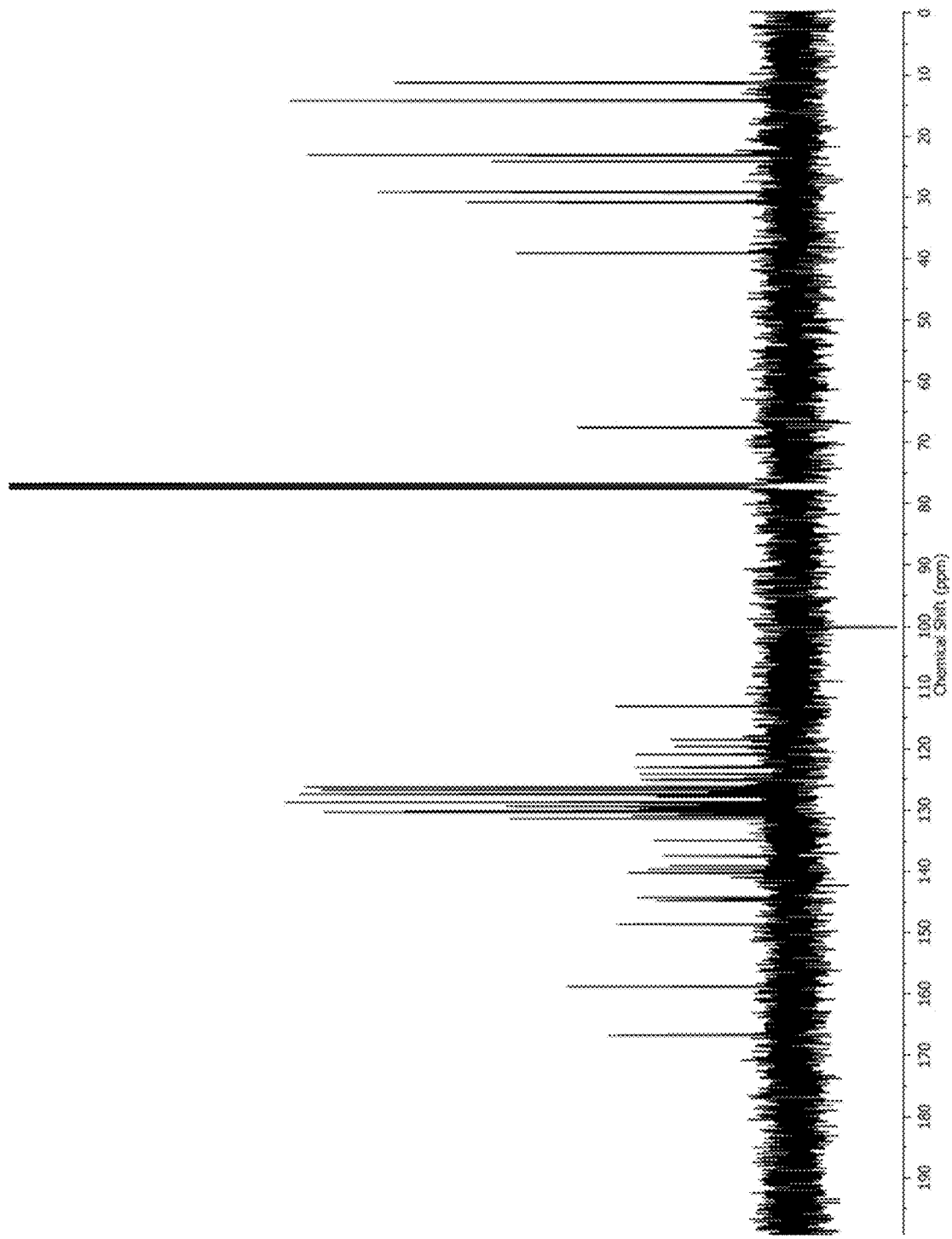
FIG. 58: is an example according to various embodiments, illustrating a characteristic $^{13}$CNMR (101 MHz, CDCl, 20° C.) spectra of compound S16 synthesized in the disclosed examples.

FIG. 58 shows $^{13}$C NMR (101 MHz, CDCl$_3$) δ (ppm) 166.74, 166.64, 158.83, 148.63, 144.79, 144.33, 140.21, 139.63, 139.04, 137.44, 134.96, 131.40, 130.92, 130.69, 130.39, 130.35, 130.13, 129.81, 129.64, 129.53, 129.35, 128.89, 128.68, 127.85, 127.54, 127.39, 126.69, 126.31, 126.22, 125.23, 125.11, 125.00, 124.26, 124.10, 123.03, 120.90, 119.64, 118.56, 113.07, 67.66, 67.59, 39.16, 39.10, 30.83, 30.77, 29.20, 29.17, 24.25, 24.19, 23.19, 23.17, 14.27, 14.24, 11.33, 11.28 spectra of compound S16.

Figure 14:
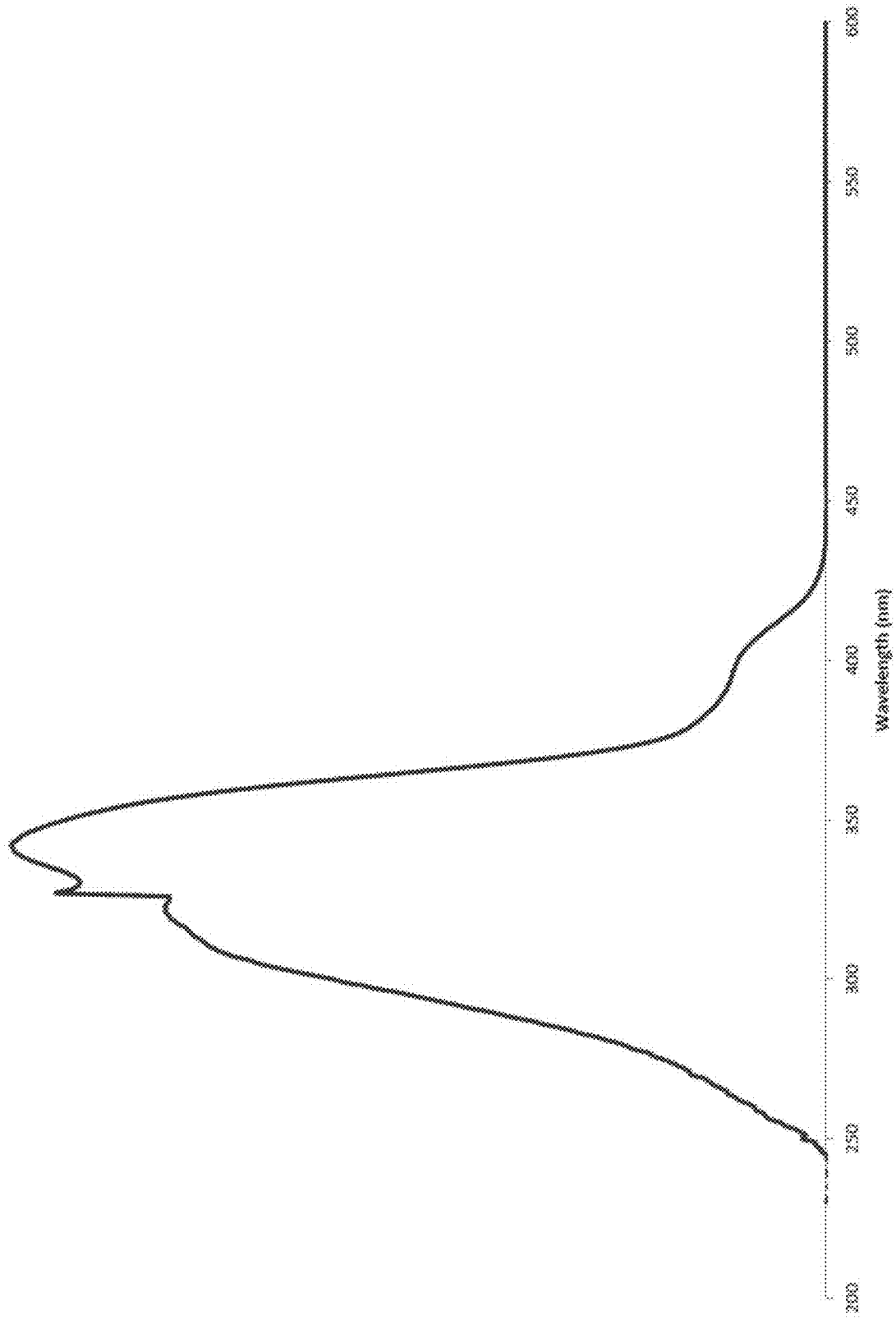
FIG. 14: is an example according to various embodiments illustrating a solid-state absorbance spectrum of compound S16 (as synthesized in the Examples) in DCE.

FIG. 14 illustrates a solid-state absorbance spectrum of compound S16 in DCE.

Figure 17:
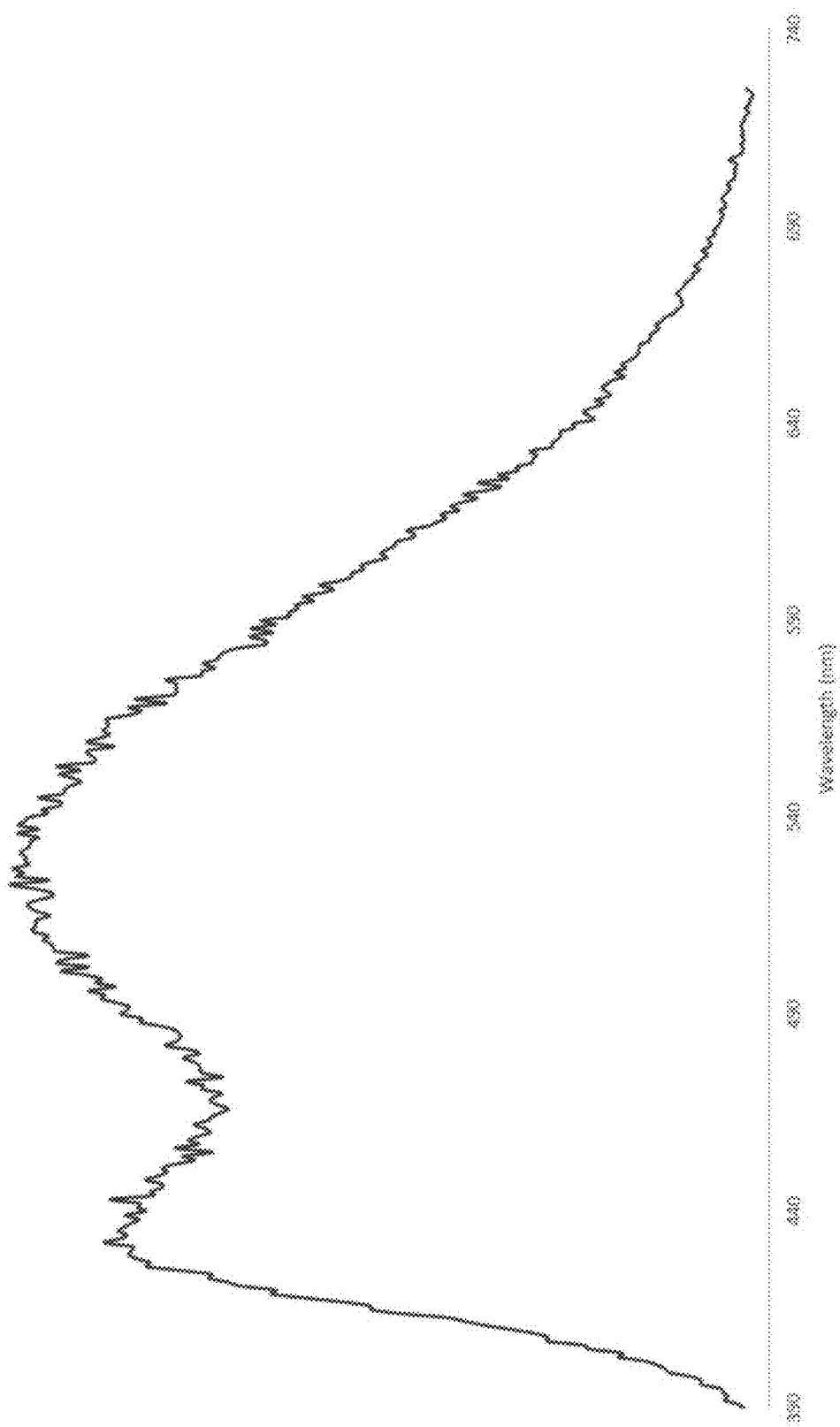
FIG. 17: is an example according to various embodiments illustrating a solid-state fluorescence spectrum of compound S16 (as synthesized in the Examples) in DCE.

FIG. 17 illustrates a solid-state fluorescence spectrum of compound S16 in

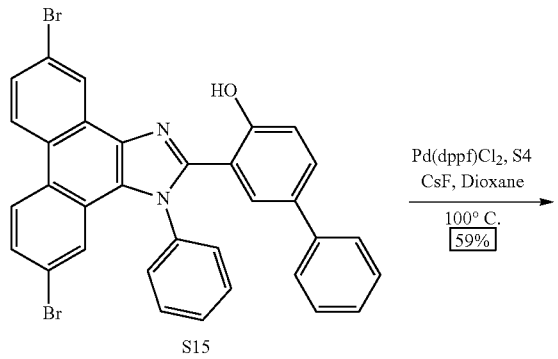

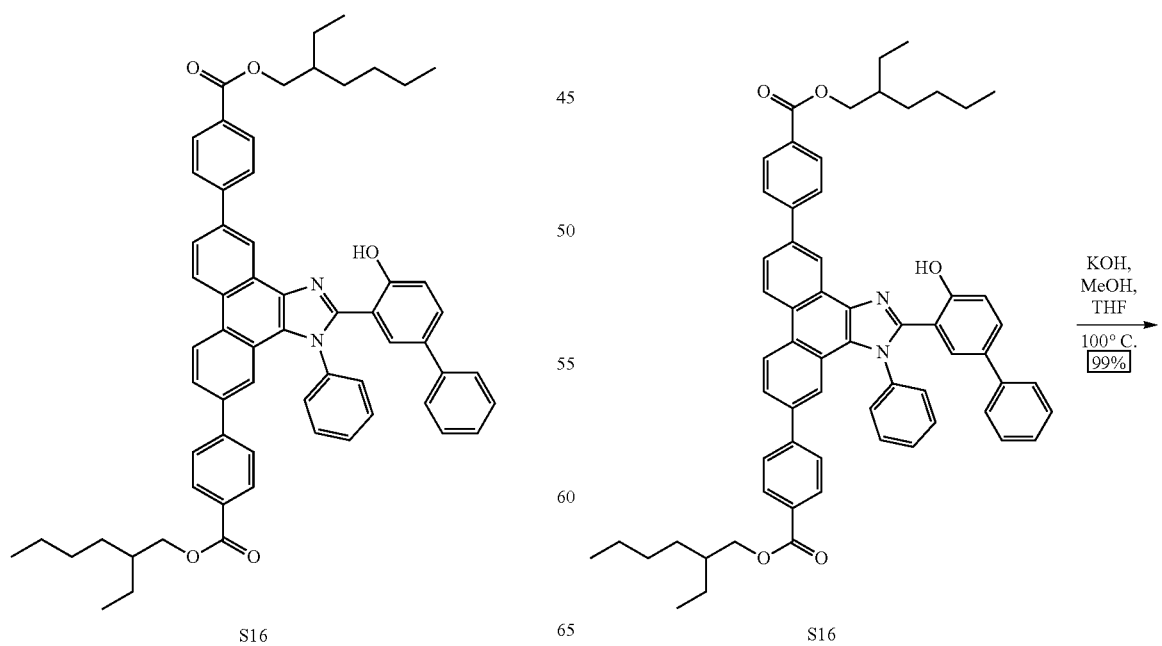

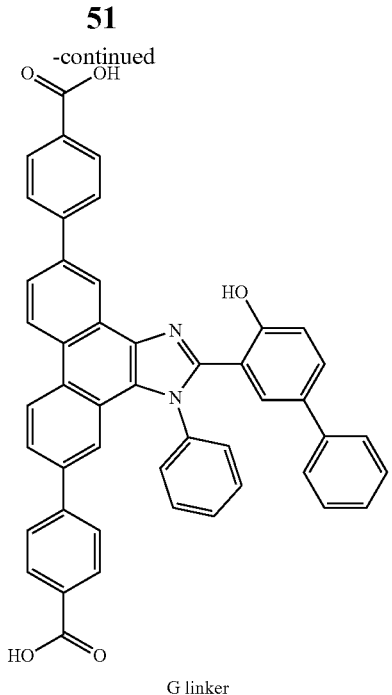

G linker 3-(5,10-bis-(4-benzoic acid)-1-phenyl-1H-phenanthro[9,10-d]imidazol-2-yl)-[1,1'-Biphenyl]-4-ol (G linker): Dissolved S16 (0.607 g, 0.655 mmol, 1.0 eq) in THF (26.2 mL). 5M KOH in methanol (6.4 mL, 32.733 mmol, 50 eq) was added to the THF solution and then heated to reflux for 4 h. The solvent was removed in a rotary evaporator and the residue was dissolved in water. The solution was quenched using 3M $H_2SO_4$ and the resulting yellow solid was collected via vacuum filtration, and rinsed with water and cold methanol. Yield 0.457 g (99%).

Figure 59:
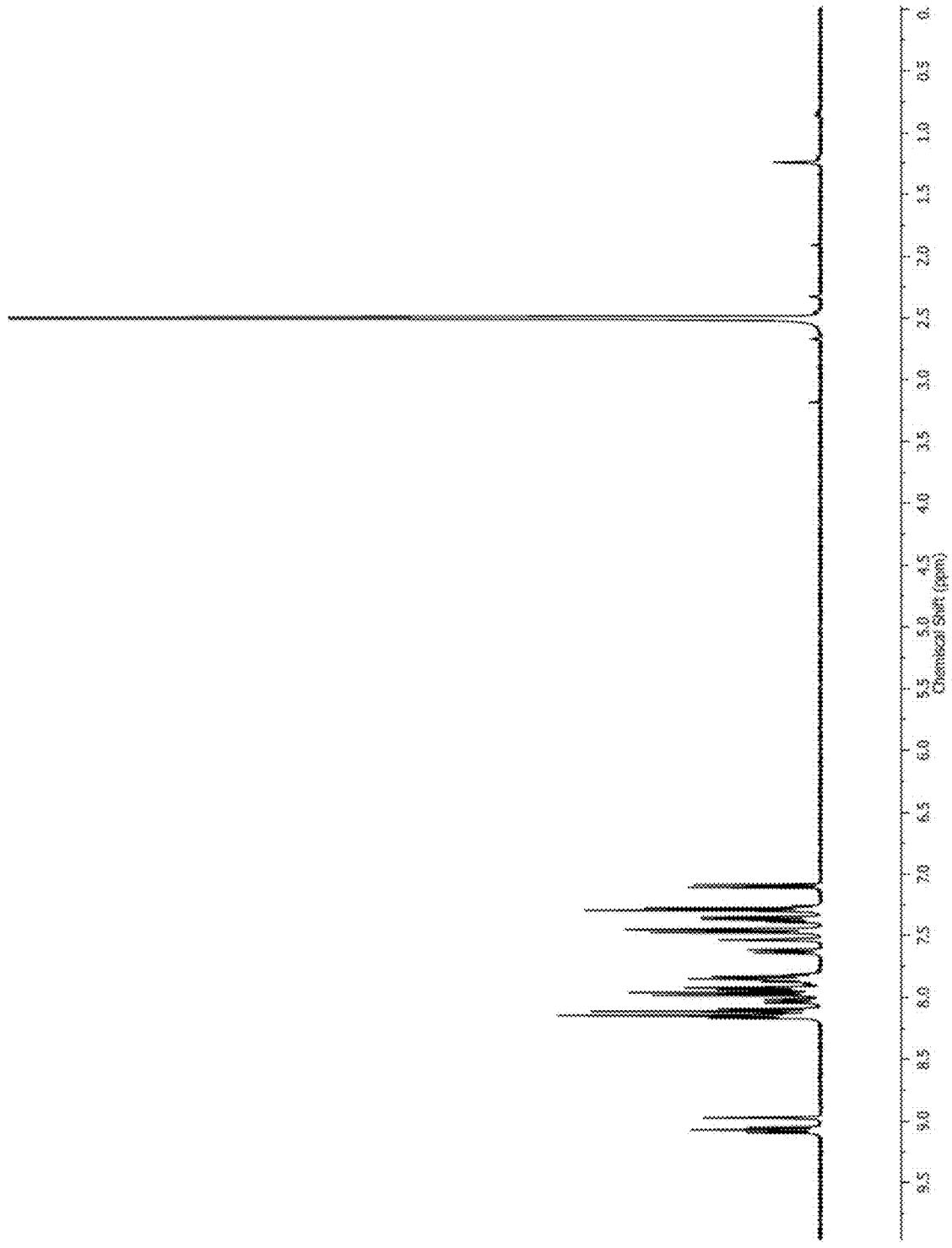
FIG. 59: is an example according to various embodiments, illustrating a characteristic $^1$HNMR (400 MHz, DMSO-d$_6$, 20° C.) spectra of a green linker compound synthesized in the disclosed examples.

FIG. 59 shows $^1$HNMR (400 MHz, DMSO-d6) δ (ppm) 9.10, 9.07, 9.05, 8.97, 8.97, 8.17, 8.14, 8.11, 8.09, 8.04, 8.04, 8.02, 8.02, 7.98, 7.96, 7.94, 7.92, 7.88, 7.81, 7.64, 7.64, 7.62, 7.62, 7.54, 7.53, 7.48, 7.45, 7.39, 7.37, 7.35, 7.30, 7.28, 7.11, 7.09, 2.50 spectra for the green linker.

Figure 60:
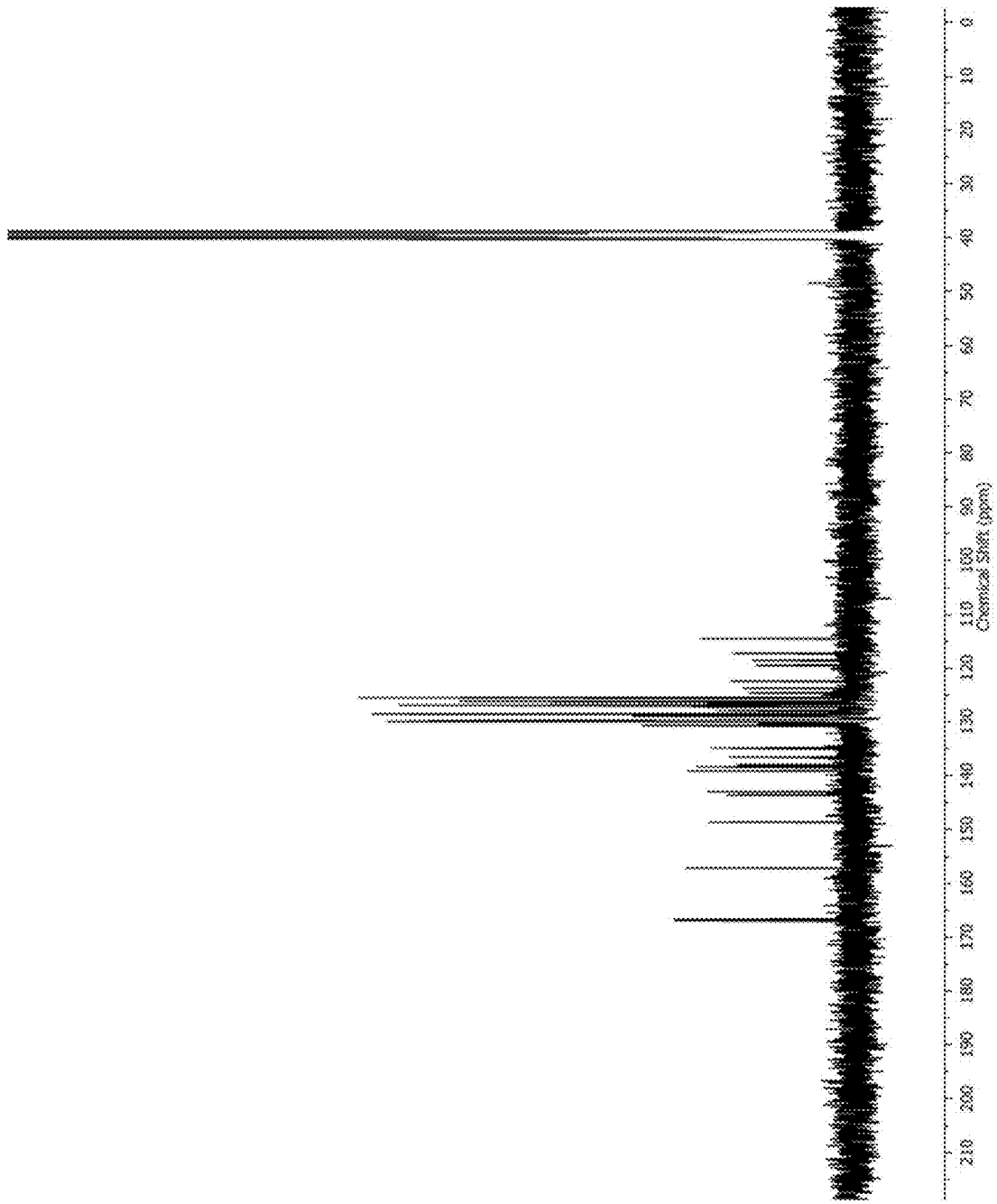
FIG. 60: is an example according to various embodiments, illustrating a characteristic $^{13}$CNMR (101 MHz, DMSO-d$_6$, 45° C.) spectra of a green linker compound synthesized in the disclosed examples.

FIG. 60 shows $^{13}$C NMR (101 MHz, DMSO-$d_6$, 45° C.) δ (ppm) 166.93, 166.74, 157.08, 148.60, 143.56, 142.93, 139.08, 138.33, 137.98, 136.51, 134.86, 130.67, 130.37, 130.03, 129.97, 129.90, 129.84, 129.72, 129.03, 128.90, 128.55, 127.92, 127.27, 127.12, 126.93, 126.55, 126.33, 126.18, 126.13, 125.55, 125.39, 124.79, 124.66, 123.76, 122.45, 119.54, 118.61, 117.31, 114.56, 39.52 spectra for the green linker.

Example 5

A purpose of this example is to illustrate a synthesis of a NF-MOF. NF linker (25 mg, 0.055 mmol, 1.0 eq) was added to a 5 mL conical vial, followed by $ZrCl_4$ (16 mg, 0.069 mmol, 1.25 eq) and anhydrous DMF (3.7 mL). The solution was lowered into an ultra-sonication bath to allow complete dissociation. Acetic acid (0.603 mL, 10.54 mmol, 190 eq) was added, and the solution was sonicated to insure homogeneity and then placed in a 120° C. oven for 5 days. After which translucent single crystals could be observed at the bottom and walls of the vial. The vial was sonicated to release the crystals from the walls and the supernatant was filtered off. The crystals were rinsed with DMF and $CH_2Cl_2$. This synthetic step is an adaptation of the prior part [11].

Example 6

A purpose of this example is to illustrate a synthesis of Blue/NF MOF. Blue linker (1 mg, 1.59 μmol, 0.1 eq) and NF linker (6.5 mg, 0.014 mmol, 0.9 eq) were added to a 2.0 mL conical vial. The vial was then transferred into an argon filled glove box were $ZrCl_4$ (5 mg, 0.020 mmol, 1.25 eq) and DMF (1.6 mL) were added. The vial was tightly capped and removed from the glovebox. The vial was lowered into an ultra-sonic bath and vortex mixer till dissolution occurred. Under a stream of argon, anhydrous acetic acid (173 μL, 3.032 mmol, 190 eq) was added and the vial was tightly capped and mixed in a vortex mixer to insure homogeneity. The vial was placed in a 120° C. oven for 4 days. The vial was cooled to room temperature and the MOF was collected by vacuum filtration and washed with DMF and DCM. See FIG. 19 for a comparison of results.

Example 7

A purpose of this example is to illustrate a synthesis of Green/NF MOF. Green linker (1.1 mg, 1.59 μmol, 0.1 eq) and NF linker (6.5 mg, 0.014 mmol, 0.9 eq) were added to a 2.0 mL conical vial. The vial was then transferred into an argon filled glove box were $ZrCl_4$ (5 mg, 0.020 mmol, 1.25 eq) and DMF (1.6 mL) were added. The vial was tightly capped and removed from the glovebox. The vial was lowered into an ultra-sonic bath and vortex mixer till dissolution occurred. Under a stream of argon, anhydrous acetic acid (173 μL, 3.032 mmol, 190 eq) was added and the vial was tightly capped and mixed in a vortex mixer to insure homogeneity. The vial was placed in a 120° C. oven for 4 days. The vial was cooled to room temperature and the MOF was collected by vacuum filtration and washed with DMF and DCM.

Example 8

A purpose of this example is to illustrate a synthesis of Orange/NF MOF. Orange linker (1.1 mg, 1.59 μmol, 0.1 eq) and NF linker (6.5 mg, 0.014 mmol, 0.9 eq) were added to a 2.0 mL conical vial. The vial was then transferred into an argon filled glove box were $ZrCl_4$ (5 mg, 0.020 mmol, 1.25 eq) and DMF (1.6 mL) were added. The vial was tightly capped and removed from the glovebox. The vial was lowered into an ultra-sonic bath and vortex mixer till dissolution occurred. Under a stream of argon anhydrous acetic acid (173 μL, 3.032 mmol, 190 eq) was added and the vial was tightly capped and mixed in a vortex mixer to insure homogeneity. The vial was placed in a 120° C. oven for 4 days. The vial was cooled to room temperature and the MOF was collected by vacuum filtration and washed with DMF and DCM. See FIG. 19 for a comparison of results.

Example 9

A purpose of this example is to illustrate a synthesis of Blue/Orange/NF MOF. Varying ratios of B and O linkers were mixed with NF linker similar to previously mentioned procedures. Example 50/50 mix, Blue linker (1.6 mg, 2.5 μmol, 0.05 eq), Orange linker (1.7 mg, 1.5 μmol, 0.0.05 eq), and NF linker (6.5 mg, 0.014 mmol, 0.9 eq) were added to a 6.0 mL conical vial. The vial was then transferred into an argon filled glove box were $ZrCl_4$ (14 mg, 0.062 mmol, 1.25 eq) and DMF (4.9 mL) were added. The vial was tightly capped and removed from the glovebox. The vial was lowered into an ultra-sonic bath and vortex mixer till dissolution occurred. Under a stream of argon anhydrous acetic acid (536 μL, 9.372 mmol, 190 eq) was added and the vial was tightly capped and mixed in a vortex mixer to insure homogeneity. The vial was placed in a 120° C. oven for 4 days. The vial was cooled to room temperature and the MOF was collected by vacuum filtration and washed with DMF and DCM. Yield=15.1 mg. See FIG. 19 for a comparison of results.

REFERENCES

1. Qin, J-S., J. Mater. Chem. A, 2017, 5, 4280-4291, doi: 10.1039/C6TA10281F;
2. Davidenko, N. A. et al Theor Exp Chem., 2017, 53: 69, doi.org/10.1007/s11237-017-9503-0;
3. Butova, V V et al., Russian Chemical Reviews 2016, 85 (3):280, doi: 10.1070/RCR4554).
4. Deng, H., et al. Science, 2010, 327, 846-850
5. http://www.crystallography.net/cod/4512072.html, accessed on Nov. 2, 2017
6. Yang, X.; Liu, D.; Miao, Q Angew. Chem. Int. Ed. 2014, 53, 6786
7. Kuss-Petermann, M.; Wenger, O. J. Am. Chem. Soc., 2016, 138, 1349
8. Park, S.; Kwon, J.; Park, S. Phys. Chem. Chem. Phys., 2012, 14, 8878
9. Cornella, J.; Zarate, C.; Martin, R. Org. Synth. 2014, 91, 260
10. Wu, K. C.; et. al. Tetrahedron, 2004, 60, 11861
11. Lippke, J.; et. al. Inorg. Chem., 2017, 56, 748.

What is claimed is:

1. A method of producing a light-emitting metal-organic framework, the method comprising:

combining at least one light-emitting linker precursor, having a formula selected from the group consisting of:

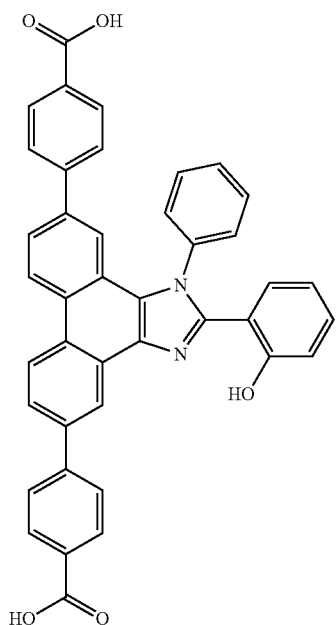

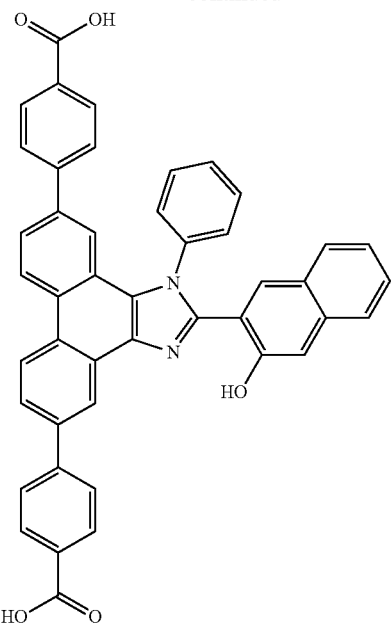

, and

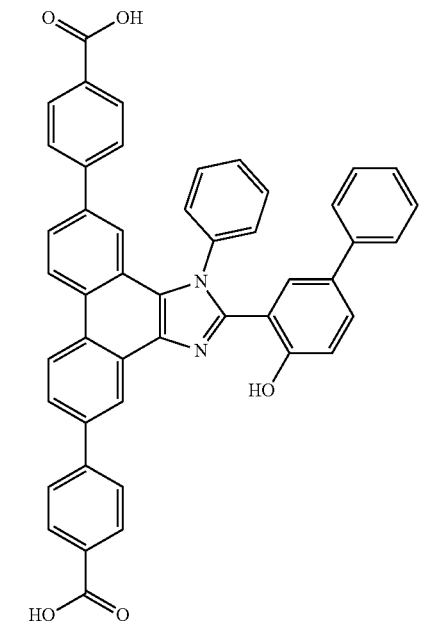

, with a non-fluorescent linker, having a formula:

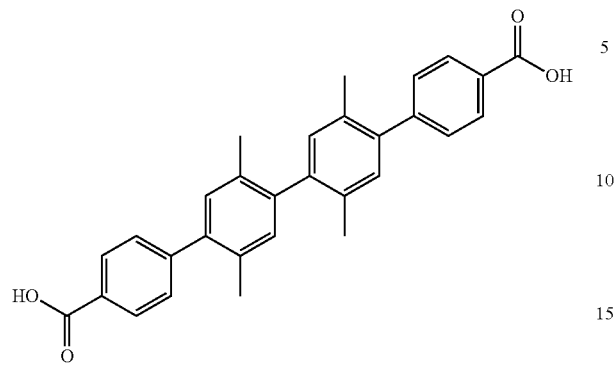

to form a first mixture;
adding an acid to the first mixture to form a second mixture; and
heating the second mixture.

2. The method of claim 1, wherein heating the second mixture comprises raising a temperature of the second mixture above 100 degrees Celsius.

3. The method of claim 2, wherein heating the second mixture is conducted for a period of at least 4 hours.

4. The method of claim 2, wherein adding the acid is conducted under a stream of argon.

5. The method of claim 2, wherein the acid is acetic acid.

* * * * *